(12) United States Patent
Silverman

(10) Patent No.: US 11,076,772 B2
(45) Date of Patent: Aug. 3, 2021

(54) METHOD AND SYSTEM ENABLING PHOTOPLETHYSMOGRAPH MEASUREMENT OF VOLUME STATUS

(71) Applicant: David G. Silverman, West Redding, CT (US)

(72) Inventor: David G. Silverman, West Redding, CT (US)

( * ) Notice: Subject to any disclaimer, the term of this patent is extended or adjusted under 35 U.S.C. 154(b) by 687 days.

(21) Appl. No.: 15/726,920

(22) Filed: Oct. 6, 2017

(65) Prior Publication Data

US 2018/0132736 A1 May 17, 2018

Related U.S. Application Data

(63) Continuation-in-part of application No. 14/511,306, filed on Oct. 10, 2014, now Pat. No. 9,782,090, which is a continuation-in-part of application No. 14/460,082, filed on Aug. 14, 2014, now abandoned, and a continuation-in-part of application No. 12/059,383, filed on Mar. 31, 2008, now Pat. No. 8,961,932.

(60) Provisional application No. 61/865,746, filed on Aug. 14, 2013, provisional application No. 61/889,780, filed on Oct. 11, 2013, provisional application No. 61/927,668, filed on Jan. 15, 2014, provisional application No. 60/920,823, filed on Mar. 30, 2007.

(51) Int. Cl.

| A61B 5/0295 | (2006.01) |
| A61B 5/02 | (2006.01) |
| A61B 5/029 | (2006.01) |
| A61B 5/026 | (2006.01) |
| A61B 5/00 | (2006.01) |

(52) U.S. Cl.
CPC ........ *A61B 5/0295* (2013.01); *A61B 5/02007* (2013.01); *A61B 5/029* (2013.01); *A61B 5/0261* (2013.01); *A61B 5/725* (2013.01); *A61B 5/6815* (2013.01); *A61B 5/7253* (2013.01); *A61B 5/7282* (2013.01)

(58) Field of Classification Search
None
See application file for complete search history.

(56) References Cited

U.S. PATENT DOCUMENTS

| 5,466,465 | A | 11/1995 | Royds et al. |
| 6,417,205 | B1 | 7/2002 | Cooke et al. |
| 6,485,431 | B1 | 11/2002 | Campbell |
| 6,656,147 | B1 | 12/2003 | Gertsek et al. |
| 6,741,895 | B1 | 5/2004 | Gafni et al. |
| 7,001,337 | B2* | 2/2006 | Dekker ................ A61B 5/0205 600/483 |
| 7,794,406 | B2* | 9/2010 | Reisfeld ............... A61B 5/1135 600/500 |
| 2005/0249774 | A1 | 11/2005 | Pauletti et al. |
| 2008/0241199 | A1 | 10/2008 | Silverman |

OTHER PUBLICATIONS

Jeong (Yonsei Med J 51(3): 345-353, 2010).*
Anderson, T.J., et al., "Close Relation of Endothelial Function in the Human Coronary and Peripheral Circulations", JACC, 1995, 26(5): 1235-1241.
Anderson, T.J., et al., "A Comparative Study of Four Anti-Hypertensive Agents on Endothelial Function in Patients with Coronary Disease", J Am Coll Cardiol 1998, 31:327A, Abst.
Anderson, T.J., et al., "Systemic Nature of Endothelial Dysfunction in Atherosclerosis", Am J Cardiol, 1995, 75:71B.
Anderson, T.J., et al., "The Effect of Cholesterol-Lowering and Antioxidant Therapy on Endothelium-Dependent Coronary Vasomotion". N Engl J Med 1995, 332:488.
Benjamin, "Hypertension", 1995; 25: 918-923.
Bjarnason, et al., "Contact Dermatitis" Sep. 1998; 39(3):112-8.
Bossaller, C., et al., "Impaired Muscarinic Endothelium-Dependent Relaxation and Cyclic Guanosine 5'-Monophosphate . . . ", Journal of Clinical Investigation, 1987, 79:170-4.
Braverman, I.M, et al., "Topographic Mapping of the Cutaneous Microcirculation Using Two Outputs of Laser-Doppler Flowmetry . . . " Microvascular Research, Jul. 1992, 44(1):33-48.
Christen, S, et al., "Dose-Dependent Vasodilatory Effects of Acetylcholine and Local Warming on Skin Microcirculation", Journal of Cardiovascular Pharmacology, 2004, 44:659-64.
"Demise of a Blockbuster Drug Complicates Pfizer's Revamp", Wall Street Journal, Dec. 4, 2006.
Drexler, H., Zeiher, A.M., Progression of Coronary Endothelial Dysfunction in man and its Potential Clinical Significance, Basic Research in Cardiology. 1991, 2:223-32.
Droog, E.J., Sjoberg, F., "Nonspecific Vasodilatation During Transdermal Iontophoresis—the Effect of Voltage Over the Skin", Microvascular Research, 2003, 65:172-8.
Ferrell, W.R., et al., "Elimination of Electrically Induced Iontophoretic Artefacts: Implications for Non-Invasive . . . ", Journal of Vascular Research, 2002, 39:447-55.
Furchgott, R.F., Zawadzki, J.V., "The Obligatory Role of Endothelial Cells in the Relaxation of Arterial Smooth Muscle by Acetylcholine", Nature, 1980, 288: 373-6.
Holowatz, L.A., et al., "Mechanisms of Acetylcholine-Mediated Vasodilatation in Young and Aged Human Skin", Journal of Physiology, 2005, 563:965-73.
Kaski, "Circulation", 74, No. 6, 1255-1265, 1986.
Khan, F., et al., "Influence of Vehicle Resistance on Transdermal Iontophoretic Delivery of Acetylcholine and Sodium . . . ", Journal of Applied Physiology, 2004, 97:883-7.

(Continued)

*Primary Examiner* — Tigabu Kassa
(74) *Attorney, Agent, or Firm* — Welsh Flaxman & Gitler LLC

(57) ABSTRACT

A method enables photoplethysmograph measurement of volume status. The method includes the steps of converting photoplethysmograph voltages to volume measurements and characterizing a local microcirculation as a microcosm in a manner allowing a photoplethysmograph to facilitate non-invasive monitoring of systemic status.

22 Claims, 51 Drawing Sheets

(56) References Cited

OTHER PUBLICATIONS

Ledger, P., "Skin Biological Issues in Electrically Enhanced Transdermal Delivery", Advanced Drug Delivery Reviews. 1991, 9:289-307.
Mo, C., Stout, R.G., Shelley, K.H., Tantawy, H., Silverman, D.G., Acute Microcirculatory Effects of Nicotine in Non-Smoking Volunteers, Anesthesiology 2004, 101:A246.
Morris, S.J., Shore, A.C., Tooke, J.E., "Responses of the Skin Microcirculation to Acetylcholine and Sodium Nitroprusside in Patients with NIDDM", Diabetologia, 1337:38-44.
Nissen, A., et al., "Consistency of Laser Doppler Assessments of Vasoreactivity", American Society of Anesthesiologists, 2006, 2A244.
Nissen, A.F., et al., "Sensitivity of Acetylcholine and Nitroglycerin-Induced Vasodilation to Endothelial Impairment", Anesthesiology, 2007, 107:A291.
Noon, J.P., et al., "Studies with Iontophoretic Administration of Drugs to Human Dermal Vessels in Vivo: Cholinergic . . . ", Br J Clin Pharmacol, 1998, 45:545-50.
Opazo Saez, A.M., et al., "Laser Doppler Imager (LDI) Scanner and Intradermal Injection for InVivo . . . ", British Journal of Clinical Pharmacology, May 2005, 59(5):511-519.
Peters, E.J., et al., "The Benefit of Electrical Stimulation to Enhance Perfusion in Persons with Diabetes Mellitus", Journal of Foot & Ankle Surgery, 1998, 37:396-400.
Saez, et al., "Br J Clin Pharmacol", 2005, 59)5): 511-19.
Scheindlin, "Molecular Interventions", Dec. 2004; 4(6): 308-312.
Schonberger, R.B., et al., "Topical Non-Iontophoretic Application of Acetylcholine and Nitroglycerin . . . ", Yale J Biol Med, 2006, 78:229-235.
Silverman, D.G., et al., "Detection and Characterization of Cholinergic Oscillatory Control in the Forehead Microvasculature . . . ", Microvasc Res, 2001, 61:144-7.
Silverman, D.G., et al., "Distinction Between Aropine-Sensitive Control of Microvascular and Cardiac Oscillatory Activity", Microvasc Res, 2002, 63:196-208.
Suzuki, "Stroke", 1993; 24: 1049-1053.
Thanyasiri, P, et al., "Endothelial Dysfunction Occurs in Peripheral Circulation of Patients with . . . ", American Journal of Physiology Heart & Circulatory Physiology, 2005, 289.
Wang, S., Omar, W., Awad, A., Scannell, M., Silverman, D.G., "Direct and Reflexive Autonomic Effects of Acupuncture in Healthy Subjects", Int Anesth Res Soc, 2002, S-215.
Wardell, K., et al., "Spatial Heterogeneity in Normal Skin Perfusion Recorded with Laser Doppler Imaging and Flowmetry", Microvascular Research, Jul. 1994, 48(1):26-38.
Wilkin, J.K., "Poiseuille, Periodicity, and Perfusion: Rhythmic Oscillatory Vasomotion in the Skin", The Journal of Investigative Dermatology, Aug. 1989, 93(2): 113S-118S.
Yoshida, M., et al.,"Impaired Forearm Vasodilatation by Acetylcholine in Patients with Hypertension", Heart & Vessels, 1991, 6:218-23.
Kraitl (J. Opt. A: Pure Appl. Opt. 7 (2005) S318-S324).
McGrath (Anesth Analg. Feb. 2011; 112(2): 368-74).

\* cited by examiner

| | |
|---|---|
| PRIMARY OBJECTIVE: INTRODUCE $AC_{rest}$MULTIPLES to eliminate impacts of attenuation and interdevice differences within and among subjects | |
| If AC is isolated by high pass (eg, >0.5 Hz) filtering, a preferred embodiment entails establishing $AC_{rest}$VOLTAGE as = mean AC height of a selected section of filtered tracing @rest | If $\Delta$AC is determined as peak-to-trough difference of individual pulses, a preferred embodiment entails establishing $AC_{rest}VOLTAGE_i$ = height of single beat or mean height of multiple beats @rest |
| CONVERT ANY & ALL PPG VOLTAGES TO # of $AC_{rest}$MULTS, WHERE: # OF $AC_{rest}$MULTS = GIVEN PPG VOLTAGE x '1 $AC_{rest}$MULT/$AC_{rest}$VOLTAGE', WHICH MAY BE EXPRESSED AS: "=GIVEN PPG VOLTAGE x '1 $AC_{rest}$MULT/$AC_{rest}$VOLTAGE'"  or as  "= GIVEN PPG VOLTAGE/$AC_{rest}$VOLTAGE" | |
| CONVERT ANY & ALL AC VOLTAGES TO # of $AC_{rest}$MULTS: = 'GIVEN AC VOLTAGE' x '1 $AC_{rest}$MULT/$AC_{rest}$VOLTAGE' Note: if calibrating measurement not attainable @rest, then can be achieved if one knows the status of the systemic stroke volume (SV) (e.g., by echocardiographic measurement)— see text. | Determine magnitude of DC component of PPG tracing in accordance with prior art methods such as measuring: mean of the raw signal; mean of signal filtered to eliminate AC component (e.g., low=pass, <0.5 Hz); and trough between individual beats generated by peak analysis. CONVERT ANY & ALL DC VOLTAGES TO # of $AC_{rest}$MULTS: = 'GIVEN DC VOLTAGE' x '1 $AC_{rest}$MULT/$AC_{rest}$VOLTAGE' |
| QUANTIFY CHANGE IN AC ($\Delta$AC) as # of $AC_{rest}$MULTS: ='#$AC_{rest}$MULTS for $AC_{NEW}$' – '#$AC_{rest}$MULTS for $AC_{PRE}$'; or ='$\Delta$AC VOLTAGE' x '1 $AC_{rest}$MULT/$AC_{rest}$VOLTAGE' | QUANTIFY CHANGE IN DC ($\Delta$DC) as # of $AC_{rest}$MULTS: = '#$AC_{rest}$MULTS for $DC_{NEW}$' – '#$AC_{rest}$MULTS for $DC_{PRE}$'; or ='$\Delta$DC VOLTAGE' x '1 $AC_{rest}$MULT/$AC_{rest}$VOLTAGE' |
| Ratio of new or $\Delta$AC in $AC_{rest}$MULTS to $AC_{PRE}$ in $AC_{rest}$MULTS (i.e., relative change of AC): =#$AC_{rest}$MULTS of $AC_{NEW}$ or $\Delta$AC/#$AC_{rest}$MULTS of $AC_{PRE}$ | Isolation of DCblood from DCbackground is required to assess relative changes of DC – see text and Figures 4 and 6. |

Figure 2

| AN OBJECTIVE OF PRESENT INVENTION: INTRODUCTION OF PHOTOPLETHYSMOGAPHIC COMPLIANCE ASSESSMENT IN $AC_{rest}$ MULTIPLES/mmHg | | | |
|---|---|---|---|
| As per Figure 2 | As per Figure 2 | | |
| | As per Figure 2 | As per Figure 2 | |
| CONVERT AC in $AC_{REST}$ MULTS to ACcompliance in $AC_{REST}$ MULTS/mmHg ='#$AC_{rest}$ MULTS for given AC time point or $\Delta AC'$/65mmHg | | CONVERT DC in $AC_{REST}$ MULT TO DCcompliance in $AC_{REST}$ MULTS/mmHg ='#$AC_{REST}$ MULTS for given DC time point or $\Delta DC'$/17.5mmHg | |
| Can determine ratio of new or $\Delta AC$ compliance to ACcompliance$_{rest\ or\ pre}$ (all in $AC_{rest}$ Mult/mmHg) or to $AC_{pre}$ or $AC_{rest}$ | | If an embodiment to distinguish DCblood has been implemented (see text and Figures 4 and 6), then one can determine ratio of new or $\Delta$ DCcompliance to pre intervention DC ($DC_{pre}$) and/or DCcompliance (DCcompliance$_{pre}$) | |

Figure 3

| AN OBJECTIVE OF PRESENT INVENTION: ALLOW FOR ELIMINATION OF BACKGROUND FROM DC DETERMINATIONS | | | |
|---|---|---|---|
| As per Figure 2 | As per Figure 2 | As per Figure 2 | As per Figure 2 |
| As per Figure 2 | | | Ratio of $DCblood_{NEW}$ or $\Delta DC$ in $AC_{rest}MULTS$ to $DCblood_{PRE}$ in $AC_{rest}MULTS$ (i.e., relative change of DCblood independent of DCbackgound): <br> $= \#AC_{rest}MULTS$ of $DCblood_{NEW} / \#AC_{rest}MULTS$ of $DCblood_{PRE}$ or <br> $= \Delta DC / \#AC_{rest}MULTS$ of $DCblood_{PRE}$ <br> Note: because it is independent of background, $\Delta DC = \Delta DCblood$ |

Figure 6

| AN OBJECTIVE OF PRESENT INVENTION: INTRODUCTION OF PHTOPLETHYMOGRAPHIC MEASURES OF ARTERIAL AND VENOUS VOLUME: | |
|---|---|
| As per Figure 2: If AC is isolated by high pass (eg. >0.5 Hz) filtering, a preferred embodiment entails establishing $AC_{rest}$VOLTAGE as = mean AC height of a selected section of filtered tracing @rest | As per Figure 2: If AC is determined as peak-to-trough difference of individual pulses, a preferred embodiment entails establishing $AC_{rest}$VOLTAGE = height of single beat or mean height of multiple beats @rest |
| Apply Plethysmographic Signal to Volume (in mlppg) CONVERSION FACTOR (CF) | |
| For Data already converted to $AC_{rest}$Mults:<br>• PPG signal (in $AC_{rest}$Mults) to volume (in $ml_{PPG}$) CF is $SV_{rest}$Volume/1$AC_{rest}$Mult<br>• Volume (in $ml_{PPG}$) for a given AC or DCblood measurement:<br>= current # of $AC_{rest}$Mults x CF<br>=current # of $AC_{rest}$Mults x '$SV_{rest}$ in ml/1$AC_{rest}$Mult'<br>• If $SV_{rest}$ is known, e.g. 125 ml, then<br>= current # of $AC_{rest}$Mults x '125 ml/1$AC_{rest}$Mult' | For Data in Volts:<br>• PPG signal (in volts) to volume (in $ml_{PPG}$) CF is $SV_{rest}$Volume/$AC_{rest}$Voltage<br>• Volume (in $ml_{PPG}$) for a given AC or DCblood measurement:<br>= current Voltage x CF<br>=current Voltage x '$SV_{rest}$ in ml/$AC_{rest}$Voltage<br>• If $SV_{rest}$ is known, e.g. 125 ml, then<br>= current Voltage x '125 ml/$AC_{rest}$Voltage' |

Figure 12

SAMPLE CONVERSION OF VOLTAGE TO VOLUME ($ml_{PPG}$)
when $AC_{rest}$ Voltage is the AC Calibration Voltage Sample Values:

$SV_{rest}$ = 125 ml (by echocardiography for given subject),
$AC_{rest}$ = 0.2 volts;
$\Delta AC$ = 0.04 volts = 0.2 $AC_{rest}$Mults;
$\Delta DC$ = 1.2 volts = 6 $AC_{rest}$Mults a) Using voltages: :
  $SV_{rest}/AC_{rest}$ conversion factor = 125 ml/0.2 volts;
  $\Delta SV$ calculation: '0.04 volts' x '125 ml/0.2 volts' = 25 $ml_{ppg}$;
  $\Delta$Venous volume calculation: '1.2 volts' x '125 ml/0.2 volts' = 750 $ml_{PPG}$.

or b) Using $AC_{rest}$Mults:
  $SV_{rest}/AC_{rest}$ conversion factor = 125 ml/1$AC_{rest}$Mult;
  $\Delta SV$ calculation: '0.2 $AC_{rest}$Mults' x '125 ml/1 $AC_{rest}$Mult' = 25 $ml_{ppg}$;
  $\Delta$Venous volume calculation: '6 $AC_{rest}$Mults' x125 ml/1 $AC_{rest}$Mult = 750 $ml_{PPG}$ If $AC_{rest}$ is not the Calibrating Voltage, then additional steps are required to calibrate the photoplethysmographic signal before it can be utilized for the conversion factor (explained in text)

Figure 13

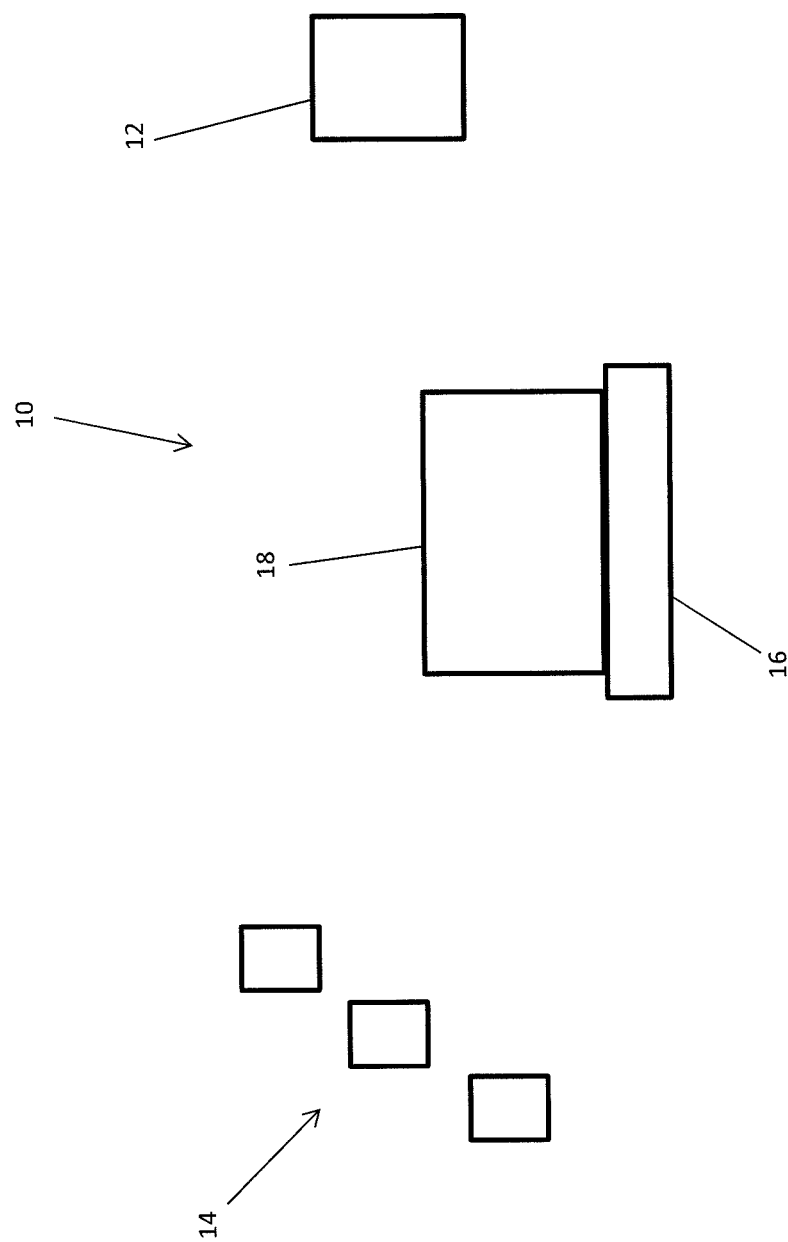

|  | Millivolts | $AC_{rest}\ Mults^a$ | PPG-derived Blood Volume (in $ml_{PPG}$) during pre and at light-headedness:<br>= Voltage x '120 ml/$AC_{rest}$ Voltage', or<br>= '# of $_{rest}$ Mults' x '120ml/1 $AC_{rest}$ Mult' |
|---|---|---|---|
| LBNP PHASE | | | |
| ACpreLBNP (equivalent to AC@rest) | 20 | 1 | 120 |
| AC@light-headedness | 8 | 0.4 | 48 |
| ΔAC | -12 | -0.6 | -72 |
| DCblood$_{pre}$ | 680 | 34 | 4080 |
| DCblood@light-headedness | 460 | 23 | 2760 |
| ΔDC | -220 | -11 | -1320 |
| RESTORATION PHASE | | | |
| AC@start of restoration (not equivalent to $AC_{rest}$) | 8 | 0.4 | 48 |
| $AC_{rest}$ (as per preLBNP) | 20 | 1 | 120 |
| AC@end of restoration | 24 | 1.2 | 144 |
| Δ AC | 16 | 0.8 | 96 |
| DC@start of restoration | 460 | 23 | 2760 |
| DC@end of restoration | 760 | 38 | 4560 |
| ΔDC | 300 | 15 | 1800 |

Figure 15

Decline in volume based upon
$SV_{rest}$ Volume/1 $AC_{rest}$ Mult conversion factor Decline in volume based upon
$SV_{rest}$Volume/$AC_{rest}$Voltage conversion factor Subject undergoing lower body negative pressure. Upper panel is raw signal; Lower panel isolates AC component.

Restoration of AC and DC in five subjects

Differences from LBNP-induced nadir in $AC_{rest}$Mults during return of sequestered blood ΔAC/ΔDC during restoration of sequestered blood Delineation of Frank-Starling relationships based upon AC and DC measurements in accordance with described embodiments Subject who developed light-headedness during blood restoration at 1822 sec.

Subject who developed hypotension during early phase of blood restoration.

| | | | CHANGES IN PPG AT FINGER AND EAR DURING LOWER BODY NEGATIVE PRESSURE | | | | |
|---|---|---|---|---|---|---|---|
| Subject # | Finger Height: relative change | Ear Height: relative change | Finger Height relative change/ Ear Height relative change | Finger DC change (in $AC_{rest}$ Mults) | Ear DC change (in $AC_{rest}$ Mults) | Finger DC change / Ear DC change (in $AC_{rest}$ Mults) | Finger DC change (in $AC_{rest}$ Mults)/ Ear DC change (in $AC_{rest}$ Mults) |
| 1 | 0.73 | 0.48 | 1.53 | 7.77 | 3.30 | 4.47 | 2.35 |
| 2 | 0.90 | 0.65 | 1.38 | 4.15 | 2.88 | 1.28 | 1.44 |
| 3 | 0.44 | 0.46 | 0.95 | 3.13 | 1.91 | 1.22 | 1.64 |
| 4 | 0.59 | 0.25 | 2.32 | 7.27 | 1.78 | 5.49 | 4.08 |
| 5 | 0.5 | 0.48 | 1.12 | 22.67 | 3.48 | 19.19 | 6.51 |
| 6 | 0.32 | 0.15 | 2.16 | 6.23 | 0.89 | 5.36 | 7.02 |
| 7 | 0.46 | 0.45 | 1.01 | 2.28 | 3.64 | -1.36 | 0.63 |
| 8 | 0.46 | 0.71 | 0.65 | 17.92 | 1.42 | 16.51 | 12.63 |
| 9 | 0.42 | 0.39 | 1.08 | 5.72 | 1.82 | 3.90 | 3.15 |
| 10 | 0.62 | 0.50 | 1.24 | 6.70 | 2.35 | 4.35 | 2.86 |
| 11 | 0.69 | 0.33 | 2.07 | 4.42 | 3.57 | 0.85 | 1.24 |
| Mean | 0.56 | 0.44 | 1.41 | 8.03 | 2.46 | 5.57 | 3.96 |
| SD | 0.17 | 0.16 | 0.54 | 6.39 | 0.96 | 6.47 | 3.55 |
| Median | 0.53 | 0.46 | 1.24 | 6.26 | 2.35 | 4.35 | 2.86 |

Figure 28

METHOD AND SYSTEM ENABLING PHOTOPLETHYSMOGRAPH MEASUREMENT OF VOLUME STATUS

CROSS REFERENCE TO RELATED APPLICATIONS

This application is a continuation in part of U.S. patent application Ser. No. 14/511,306, filed Oct. 10, 2014, entitled "METHOD AND SYSTEM ENABLING PHOTOPLETHYSMOGRAPH MEASUREMENT OF VOLUME STATUS," which is a continuation-in-part of U.S. patent application Ser. No. 14/460,082, filed Aug. 14, 2014, entitled "METHOD AND SYSTEM ENABLING PHOTOPLETHYSMOGRAPH MEASUREMENT OF VOLUME STATUS," which is now abandoned, which claims the benefit of U.S. Provisional Application Ser. No. 61/865,746, filed Aug. 14, 2013, entitled "CONVERTING PHOTOPLETHYSMOGRAPHIC VOLTAGE TO A VOLUME MEASUREMENT: UNIQUE APPLICATION OF THE AC COMPONENT TO NORMALIZE FOR SIGNAL ATTENUATION WITHIN AND AMONG SUBJECTS," U.S. Provisional Application Ser. No. 61/889,780, filed Oct. 11, 2013, entitled "CONVERTING PHOTOPLETHYSMOGRAPHIC (PPG) VOLTAGE TO A VOLUME MEASUREMENT: UNIQUE APPLICATION OF THE AC COMPONENT TO NORMALIZE FOR SIGNAL ATTENUATION, ESTABLISH A VOLTAGE TO VOLUME CONVERSION FACTOR AND ELIMINATE IMPACT OF BACKGROUND," and U.S. Provisional Application Ser. No. 61/927,668, filed Jan. 15, 2014, entitled "CONVERTING PHOTOPLETHYSMOGRAPHIC (PPG) VOLTAGE TO A VOLUME SIGNAL: ADDITIONAL MODIFICATIONS TO IMPROVE UTILITY IN CLINICAL AND INVESTIGATIVE SETTINGS, this application is also a continuation in part of U.S. patent application Ser. No. 14/511,306, entitled "METHOD AND SYSTEM ENABLING PHOTOPLETHYSMOGRAPH MEASUREMENT OF VOLUME STATUS," which is a continuation-in-part of U.S. patent application Ser. No. 12/059,383, entitled "'MICROPATCH'" FOR ASSESSMENT OF THE LOCAL MICROVASCULATURE AND MICROCIRCULATORY VASOREACTIVITY," filed Mar. 31, 2008, which issued as U.S. Pat. No. 8,961,932 on Feb. 24, 2015, which claims the benefit of U.S. Provisional Patent Application Ser. No. 60/920,823, filed Mar. 30, 2007, entitled "'MICRO-PATCH' FOR ASSESSMENT OF THE LOCAL MICROVASCULATURE AND MICROCIRCULATORY VASOREACTIVITY," and this application is also a continuation in part of U.S. patent application Ser. No. 14/511,306, entitled "METHOD AND SYSTEM ENABLING PHOTOPLETHYSMOGRAPH MEASUREMENT OF VOLUME STATUS," which claims the benefit of U.S. Provisional Application Ser. No. 61/889,780, filed Oct. 11, 2013, entitled "CONVERTING PHOTOPLETHYSMOGRAPHIC (PPG) VOLTAGE TO A VOLUME MEASUREMENT: UNIQUE APPLICATION OF THE AC COMPONENT TO NORMALIZE FOR SIGNAL ATTENUATION, ESTABLISH A VOLTAGE TO VOLUME CONVERSION FACTOR AND ELIMINATE IMPACT OF BACKGROUND," and U.S. Provisional Application Ser. No. 61/927,668, filed Jan. 15, 2014, entitled "CONVERTING PHOTOPLETHYSMOGRAPHIC (PPG) VOLTAGE TO A VOLUME SIGNAL: ADDITIONAL MODIFICATIONS TO IMPROVE UTILITY IN CLINICAL AND INVESTIGATIVE SETTINGS, all of which are incorporated herein by reference.

BACKGROUND OF THE INVENTION

1. Field of the Invention

The invention relates to a method and system enabling photoplethysmograph measurement of volume status.

2. Description of the Related Art

Assessments of impact on blood volume by challenges ranging from local application of a vasoactive agent to systemic blood loss share a common problem—how to effectively monitor the impacts noninvasively. Moreover, they may share a common solution—a heretofore unreported use of the photoplethysmograph (PPG, also referred to as photoplethymogram) to delineate local as well as systemic changes in pulsatile volume ("AC" which represents portion of the stroke volume (SV) delivered to the given site) and nonpulsatile volume ("DC," which represents the venous volume+arterial volume at given site, except for the portion of arterial volume that changes with each stroke volume, i.e., except for the AC).

Monitoring of local volume and flow has been thwarted by limitations. Thermometry is nonspecific; radionuclide and substrate sampling are invasive; laser Doppler flowmetry has high spatial heterogeneity (due to varying numbers of arterioles and capillaries in its 1 $mm^3$ sampling area); measurement of flow-mediated vasodilation measures changes in larger vessels in limited locations; strain gauge plethysmography is nonspecific and limited as to site of application; and, in the absence of methods and systems disclosed in accordance with the present invention, photoplethysmograph is confounded by attenuation (based on extinction coefficient of the media transversed by the transmitted light) and background (non-blood tissues).

Moreover, none of the noninvasive techniques distinguishes arterial and venous volume; thus, they cannot fully characterize local physiologic impact and its relationship to arterial and venous components of the systemic circulation.

Monitoring of systemic volume likewise has been challenging, prompting a search for alternatives to invasive (and not consistently reliable) central venous and pulmonary artery pressure monitoring. When available, echocardiography often provides the gold standard, but preload measurements have been inconsistent and stroke volume measurements during lower body negative pressure (LBNP), a model of simulated blood loss, are disturbed by vacuum-induced changes in chest alignment; likewise for measures of thoracic impedance. Monitoring contour and magnitude of arterial pressure and photoplethysmograph waveforms are impacted by changes in local vascular tone; thus far, neither has quantified changes in venous volume. Although increases in ventilation-induced variations in intra-arterial and intra-venous waveforms can identify hypovolemia, they do not quantify volume status and the effectiveness of such monitoring is limited in the absence of positive pressure ventilation.

The monitoring limitations in the aforementioned settings have prompted investigations into mechanisms for improving interpretation of changes in the signal generated by the photoplethysmograph. The conventional wisdom has been that, although AC height trends with stroke volume, most potentially meaningful volume information within photoplethysmograph voltages is obscured by background, attenuation, inconsistencies among devices and regional vasomotor activity. Hence, analysis of individual photoplethysmograph beats typically entails voltage clamping and complex contour analysis. On a local level, investigators and clinicians have evaluated changes in pulse height attributable to ischemia, autonomic activity, and regional anesthetics. However, changes in arterial and venous volume have not been effectively distinguished and compared. Recent efforts to assess systemic volume have focused on ventilation induced variations of the photoplethysmograph waveform, such as plethysmographic variability index (PVI) and spectral-domain analysis of oscillatory activity at the respiratory frequency. However, and as noted above, these only provide relative assessments (i.e., they neither measure nor estimate actual volume), and they are confounded by rate, depth and pattern of respiration.

A major limitation to the use of the photoplethysmograph for these purposes is that commercial devices (e.g., for clinical monitoring) have autocentering and/or dynamic recalibrating algorithms that minimize changes in voltages caused by what I believe to be important physiologic changes. This is because the commercial photoplethysmograms are components of pulse oximeters, designed to identify the time of arterial pulsation so as to determine arterial oxygen saturation; changes in the photoplethysmographic tracing have been considered "distracting." I believe that what others have considered noise is actually music, hence, unless otherwise specified, all photoplethysmographic data shown herein are obtained using noncommercial devices without the aforementioned algorithms and the embodiments included herein are derived from said data.

SUMMARY OF THE INVENTION

It is, therefore, an object of the present invention to provide a method enabling photoplethysmograph measurement of volume status despite current limitations including those imposed by attenuation and background. The method includes the steps of converting photoplethysmograph voltages to multiples of a calibrating voltage and to voltage-derived volume measurements, thereby enabling characterization of a local microcirculation as a microcosm in a manner allowing a photoplethysmograph to facilitate noninvasive monitoring of systemic as well as local status.

It is also an object of the present invention to provide a method wherein the step of converting includes introducing an AC Calibration Voltage, defined herein as the measured voltage generated by the small portion of a cardiac stroke volume delivered to a given photoplethysmograph at a given site in a given subject at the time of calibration.

It is another object of the present invention that the AC Calibration Voltage be obtained under undisturbed baseline conditions (i.e., $AC_{rest}$ Voltage is the basis for calibration).

It is a further object of the present invention to provide a method including the step of applying the $AC_{rest}$ Voltage (=$AC_{rest}$Equivalent) in converting AC values at any and all time points for given photoplethysmograph at given site to $AC_{rest}$Multiples ($AC_{rest}$Mults).

It is a further object of the present invention to provide a method including the step of applying the $AC_{rest}$ Voltage in comparing DC values for given photoplethysmograph at given site as $AC_{rest}$Mults.

It is a further object of the present invention to relate the $AC_{rest}$ Voltage to a resting measurement of cardiac stroke volume (SV), wherein $SV_{rest}$Volume is measured by a method such as echocardiography or estimated based on known population data.

It is an additional object of the present invention to convert AC voltages and/or changes thereof that are multiples or fractions of the $AC_{rest}$ Voltage to multiples or fractions of $SV_{rest}$Volume, as may be enabled by one of two conversion factors introduced herein:
  $SV_{rest}$Volume/1 $AC_{rest}$Mult conversion factor, if given AC reading is in $AC_{rest}$Mults; or
  $SV_{rest}$Volume/$AC_{rest}$ Voltage conversion factor, if given AC reading is in volts.

It is an additional object of the present invention to convert DC voltages and/or changes thereof that are multiples or fractions of the $AC_{rest}$ Voltage to multiples or fractions of $SV_{rest}$Volume, as may be enabled by a:
  $SV_{rest}$Volume/1 $AC_{rest}$Mult conversion factor, if given DC reading is in $AC_{rest}$Mults; or
  $SV_{rest}$Volume/$AC_{rest}$ Voltage conversion factor, if given DC reading is in volts.

It is an additional object of the present invention to enable calibration at a time point other than @rest by relating AC voltage at given time point ($AC_{GivenTimePoint}$ Voltage) to a measurement of stroke volume (or alternative parameter) at the given time point (e.g. $SV_{GivenTimePoint}$Volume). This may either:
  generate $AC_{GivenTimePoint}$Mults; and/or
  enable the $AC_{\sim rest}$ Voltage and hence $AC_{rest}$Mults to be obtained by extrapolating according to the $SV_{GivenTimePoint}/SV_{rest}$ ratio
  (where $SV_{rest}$ is either estimated or already was measured under batime pointseline conditions).

It is also an object of the present invention to provide a method wherein arterial and/or venous compliance can be determined It is also an object of the present invention to provide a method wherein the relationship between changes in DC and AC can be used to provide Frank-Starling relationships as may occur during volume loss and replacement.

It is also an object of the present invention to provide a method wherein the AC Calibration Voltage for a photoplethysmogaph placed on the Ear is determined based upon Ear measurements.

It is another object of the present invention to provide a method wherein the AC Calibration Voltage for a photoplethysmograph placed on the forehead is determined based upon Forehead measurements.

It is another object of the present invention to provide a method wherein the AC Calibration Voltage for a photoplethysmograph placed on an alternative site such as the finger of nasal ala is determined based upon respective measurements.

It is an additional object of the present invention to provide a method for noninvasive measurement of arterial and venous components of the circulation utilizing a photoplethysmograph at one or more sites for independent and comparative assessment in clinical and investigative settings.

It is addition an object of the present invention to provide a method for assessing physiologically meaningful values (i.e., $AC_{rest}$Mults and $SV_{rest}$Mults as opposed to voltages) by spectral-domain analysis.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 2 is a flow chart for establishing $AC_{rest}$Multiples ($AC_{rest}$Mults) in accordance with the present invention.

FIG. 3 is a flow chart for establishing $AC_{rest}$Mults in accordance with an alternate embodiment of the present invention that calculates arterial and venous compliance.

FIG. 6 is a flow chart for establishing $AC_{rest}$Mults in accordance with an alternate embodiment of the present invention wherein conversion of DC to DCblood enables measurement of relative as well as absolute changes.

FIG. 12 is a flow chart for converting photoplethysmographic readings to volume measurements in accordance with an alternate embodiment of the present invention.

FIG. 13 is a sample conversion of voltage to volume and $AC_{rest}$Mults to volume.

FIG. 14 is a schematic of a system in accordance with the present invention.

FIG. 15 shows a table of hypothetical measurements during hypovolemia (simulated blood loss) in accordance with the present invention.

FIG. 28 shows the data obtained during concurrent monitoring of plethysmographic signals at the Ear and Finger during lower body negative pressure.

DESCRIPTION OF THE PREFERRED EMBODIMENTS

Figure 1:
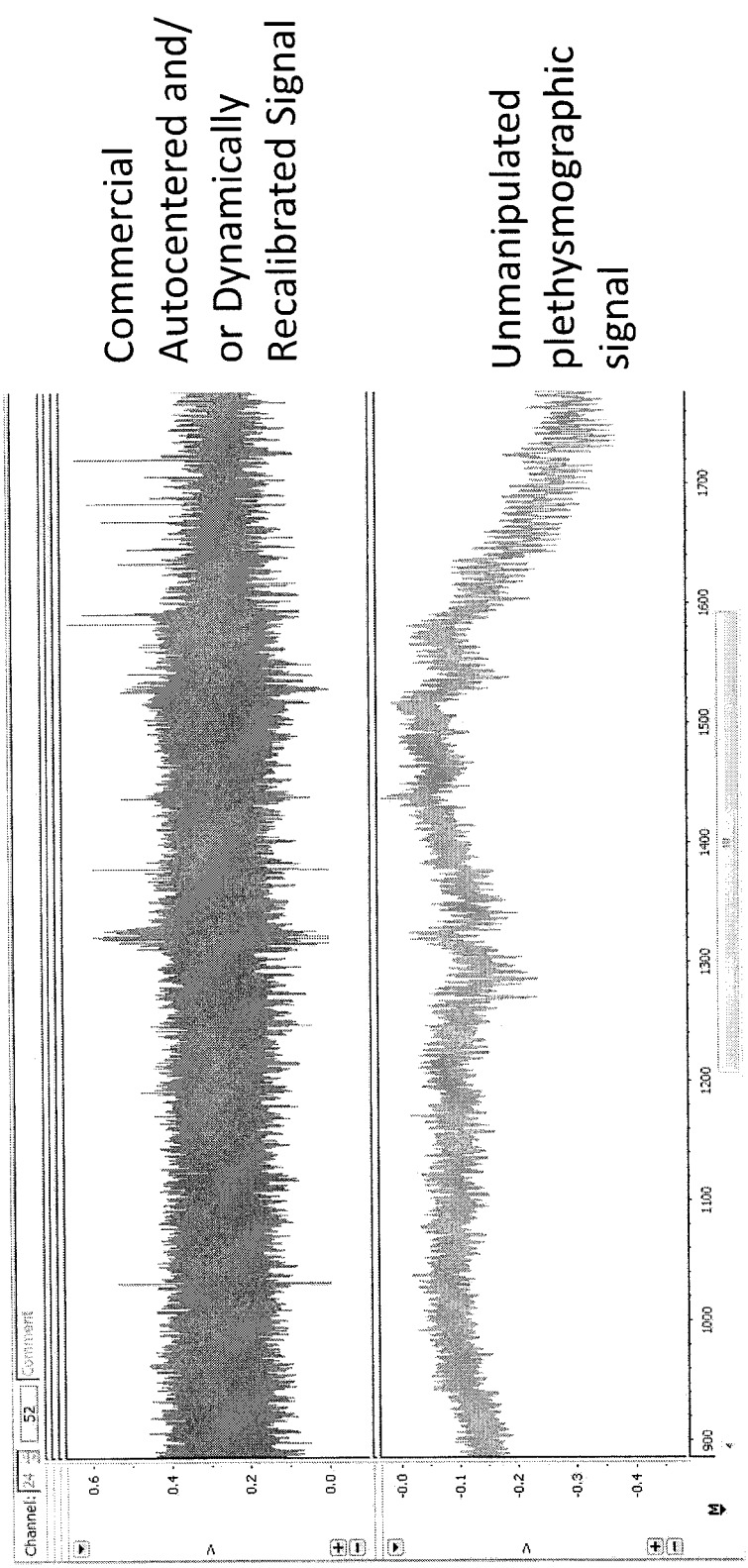
FIG. 1 shows autocentered and non-autocentered plethysmographic tracings during baseline period followed by simulated blood loss in accordance with the established model of applying lower body negative pressure utilized herein. Data encompasses interval between ~900 and ~2000 seconds, such that oscillations (predominantly at the respiratory frequency of ~0.2 Hz) but not individual beats (at 1 to 2 Hz) are discernible.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

With reference to the accompanying figures, a system and method enabling photoplethysmograph monitoring and measurement of volume status by establishing the "AC Calibration Voltage," which is the measured voltage generated by the small portion of a cardiac stroke volume delivered to a given photoplethysmograph at a given site in a given subject at the time of calibration, of a given photoplethysmograph at a given site under resting conditions so as to convert all voltages (photoplethysmographic (PPG) signal and its AC and DC components) to herein introduce "AC Multiples" of the AC Calibration Voltage, wherein the value (or number) of AC Multiples represents the ratio of the measured photoplethysmograph voltage to the resting photoplethysmographic voltage as explained below in greater detail. The present system and method further provides for the conversion of photoplethysmograph voltages to volume measurements and enables the local microcirculation to be characterized as a microcosm such that the photoplethysmograph can serve as a noninvasive window for monitoring systemic as well as local cardiovascular (vessel physiology, pharmacology and volume) status. By introducing AC MULTIPLES the impact of attenuation is eliminated. Further, a common mechanism is provided for conversion to heretofore unattainable common units for within parameter & interparameter (e.g., AC & DC), within site & intersite, and within subject & intersubject measurements and comparisons (with common units and elimination of impact of attenuation).

With the foregoing in mind, the present invention seeks to discern the music within the cacophony of photoplethysmograph variables based in part upon a foundation of known, but at times under-appreciated, features of photoplethysmograph monitoring pertaining to:
 a) signal components;
 b) nature of photoplethysmograph signal processing; and
 c) sites of monitoring.

With reference to Table 1 as presented below, it is appreciated that although both AC and DC are affected by attenuating properties of the signal path (e.g., skin color), only DC is affected by background (i.e., absorption of relevant wavelengths by tissues within bone and muscle). AC is independent of background since it is the difference between peak and trough for a given beat, both of which have the same background component.

TABLE 1

Factors Confounding AC and DC Measurements

| | AC | DC |
|---|---|---|
| Attenuation | YES* | YES |
| Background | NO | YES |

*AC represents change in voltage: Peak - Baseline, each of which has the same background component. Hence, background is subtracted out of the AC measurement.

In developing the present invention, it has been appreciated that prior failures to identify or fully appreciate the changes in the vasculature at sites of photoplethysmograph monitoring have been attributable, in part, to auto-centering and dynamic recalibration of the photoplethysmograph signal, in an attempt to provide a stable "pleasant" waveform. However, these actions may obscure the impact of relevant physiologic changes. The lower channel of FIG. 1 shows a raw: plethysmographic tracing that has not been subjected to auto-centering and dynamic recalibration. Except when otherwise started, such a device is used for plethysmographic data presented herein. It is shown on an interfaced display after sampling at 200 Hz. Time is shown on the horizontal axis. Output in volts is shown on the vertical axis. With the onset of lower body negative pressure, a model of simulated hypovolemia used in volunteers, the decline in circulating volume was reflected by a decline in plethysmographic voltage. In contrast, the auto-centering and dynamic recalibration features of the commercial photoplethysmograph (upper tracing of FIG. 1) masked this decline as if an undesirable diversion, thereby maintaining a stable tracing. Clearly, the manufacturers (and users) of such devices have not placed much credence on the potential for the photoplethysmograph to provide meaningful measurements of volume.

It has also been appreciated in the development of the present invention that while the most common monitoring site (i.e., finger) is prone to sympathetically mediated vasoconstriction, the forehead (FH), ear and other central regions (e.g., nasal ala) are relatively immune to vasoconstriction due to physiologic and pharmacologic challenges. In accordance with the aforementioned observations, recent studies by our research team show that AC monitoring at the ear (AC@Ear) and systemic stroke volume determined by voltage clamping on the arm declined similarly—by 39.3% and 41.3%, respectively—between baseline and onset of lightheadedness during lower body negative pressure. Likewise, AC monitoring at the Forehead (AC@FH) and echocardiographic measurement of stroke volume decreased by 26.5±11.8% and 26.8±9.6%, respectively (P=NS (P value non-significant)), after withdrawal of 2 units of blood from six healthy volunteers. In resting volunteers, intrasession (over the course of 30 min) and intersession (different days) consistencies of AC@FH readings were comparable to that reported for serial echocardiographic measures of stroke volume (related below).

As shown in FIG. 2, the aforementioned relationships have prompted the present introduction of the "AC Calibration Voltage." Except under rare exceptions (discussed below), "AC Calibration Voltage" is the AC voltage at the given site when the subject (and given site) is at rest ("$AC_{rest}$ Voltage"). As used herein, $AC_{rest}$ Voltage at the Forehead and Ear references the voltage change generated by the small portion of the stroke volume (which is generated by each heart beat) delivered to the given photoplethysmograph, more particular, it references voltage change generated by a small portion of a stroke volume delivered to a given noncentering, nonrecalibrating photoplethysmograph at a given site in a given subject under resting conditions. When attainable, $AC_{rest}$ Voltage serves as the "Calibration Voltage," providing a basis for comparing all subsequent AC values for given photoplethysmograph at a given site as $AC_{rest}$Multiples (also referred to herein a $AC_{rest}$Mults(s) or number of $AC_{rest}$Mults). Unless otherwise specified, the $AC_{rest}$ Voltage is used herein for calibration and hence $AC_{rest}$Mults are used as the unit for conversion of other voltages.

At any and all other time points, AC readings at the given site can be converted to $AC_{rest}$Mults, with the following equation (where # means "number of"):

of $AC_{rest}$MULTS='GIVEN AC VOLTAGE'×'1 $AC_{rest}$MULT/$AC_{rest}$VOLTAGE', wherein $AC_{rest}$ Voltage is the $AC_{rest}$Calibration Voltage as discussed above and 1 $AC_{rest}$MULT is equal to "1" for the purposes of calculation given that a single $AC_{rest}$MULT is characterized to equal the $AC_{rest}$ Voltage.

Likewise, DC voltage values also are to be expressed as $AC_{rest}$Mults:

of $AC_{rest}$MULTS='GIVEN DC VOLTAGE'×'1 $AC_{rest}$MULT/$AC_{rest}$VOLTAGE'

The number of $AC_{rest}$Mults can similarly be obtained with the following abbreviated equations:

of $AC_{rest}$MULTS=GIVEN AC VOLTAGE/$AC_{rest}$ VOLTAGE; and of $DC_{rest}$MULTS=GIVEN DC VOLTAGE/$AC_{rest}$ VOLTAGE.

The exception alluded to above occurs when the $AC_{rest}$ Voltage does not constitute the calibrating voltage. This would be case if the first measurement on a subject (e.g., patient) is obtained after a challenge (e.g., insult such as surgery or an injury causing blood loss) has occurred before any measurements have been taken. At this time, the AC Calibration Voltage is more aptly termed $AC_{GiveTimePoint}$ Voltage and the AC Multiples are $AC_{GivenTimePoint}$Mults. Additionally, and as detailed below, since the present invention will allow measurements of blood volume, one may wish to calibrate vs. a less readily available technique such as the stroke volume measurements of echocardiography (if it is available). This typically would occur at rest ($SV_{rest}$). However, it may not have been sought during rest and thus may be obtained at a different time point and the calibration voltage would not be at rest. This is explored in greater detail in the context of volume measurements as discussed below.

The difficulties pertaining to obtaining an $AC_{rest}$ measurement often may be avoidable. Healthcare providers, military personnel and others facing potential blood loss should be assured by documentation that $AC_{rest}$ has high intrasession and intersession stability. Its consistency was comparable to that reported for the echocardiography, the "gold standard." In recently obtained photoplethysmographic data obtained over multiple sessions, 2× standard error of $AC_{rest}$ Voltage averaged 8% of mean; this was less the 11% for SV that was reported using echocardiography on successive days (Ihlen H, et l Amer J Cardiol 1987; 115:59(9) 9756). Moreover, intrasession 2×SE/Mean averaged only 3%. The consistency of $AC_{rest}$ Voltage means that it can be recorded prior to the start of surgery or even days, weeks, months . . . prior to going into battle.

It is anticipated that reliability and consistency can be improved by use of artifact and movement rejection algorithms and multiple filters to enable delineation of blood vs. other tissues and ideally isolate the arterial and venous blood components. Substrate concentrations and arterial/venous differences thereof also may be assessed.

Each of the above equations facilitates AC and DC comparison and offers the added benefit of removing the impact of attenuation, since each AC and DC measurement and the calibrating $AC_{rest}$ Voltage are attenuated proportionately. The stability of $AC_{rest}$ values at the Ear and Forehead under resting conditions bolsters the foundation for the present introduction of $AC_{rest}$Mults during local and systemic challenges in two sets of healthy volunteers.

More particularly, and with reference to FIG. 2, the introduction of $AC_{rest}$Mults to eliminate impacts of attenuation and inter-device differences within and among subjects is achieved in the following manner. In accordance with the present method and system, if AC is isolated by high pass (e.g., >0.5 Hz) filtering, a preferred embodiment entails establishing $AC_{rest}$ Voltage$_{(filtered)}$ as equaling the mean AC height of a selected section of a filtered tracing at rest. If alternatively AC is determined as peak-to-trough difference of individual pulses, a preferred embodiment entails establishing $AC_{rest}$ Voltage$_{(peak\ analysis)}$ as equaling the height of single beat or mean height of multiple beats at rest; alternatively, it may be calculated as by dividing beat area by beat width. For purposes of overall consistency, it will be advisable to have universal consensus as to a consistent means of $AC_{rest}$ Voltage measurement. Since the differences are relatively small (and a consensus has not yet been reached), the methods are used interchangeably herein.

Regardless of whether AC is isolated by high pass filtering or AC is determined as peak-to-trough difference, any and all photoplethysmographic voltages are converted to the number of $AC_{rest}$Mults, as per the equations cited above.

One can also define changes in (Δ) AC or changes in (Δ) DC in terms of $AC_{rest}$Mults. For example, For AC:

$$\Delta AC = `\#AC_{rest}\text{MULTS for }AC_{NEW}` - `\#AC_{rest}\text{MULTS for }AC_{PRE}`; \text{ or}$$

$$\Delta AC = \Delta AC\ \text{VOLTAGE} \times `1\ AC_{rest}\text{MULT}/AC_{rest}\ \text{VOLTAGE}`$$

For DC $$\Delta DC = `\#AC_{rest}\text{MULTS for }DC_{NEW}` - `\#AC_{rest}\text{MULTS for }DC_{PRE}`; \text{ or}$$

$$\Delta DC = \Delta DC\ \text{VOLTAGE} \times `1\ AC_{rest}\text{MULT}/AC_{rest}\ \text{VOLTAGE}`$$

As those skilled in the art will certainly appreciate, and with reference to FIG. 14, the methodology described above is preferably implemented via a computer based system 10 linked to a conventional photoplethysmograph 12 and a variety of data source(s) 14 as may be deemed necessary, which cumulatively represent a database of information. The system 10 is further provided with output displays and input mechanisms (for example, computer stations 16 with a graphical user interface 18) as are well known in the art. It is further appreciated, the various components making up the present system may be integrated into a single station from which information is input, processed and output. Similarly, the present system may be configured in more elaborate arrangements with multiple data sources, input mechanisms and output displays, or it may be a standalone unit. Items such as demographic data may be hand-entered. Options may be available for channel selection, time and output parameters, with split screens to allow comparison among sections of data. Data may be processed for comparison within and among parameters, within and among monitoring devices.

Objectives & Hypotheses of Study Models:

With the foregoing introduction of $AC_{rest}$Mults in mind, the objective and hypotheses underlying the present invention where tested on first and second series of subjects. The local challenge ($1^{st}$ series of subjects) entailed photoplethysmograph monitoring during transdermal application of vasoactive agents [nitroglycerin (Nitro) and nicotine (NIC)] as translucent "micro-patches," an expansion of prior work where laser Doppler flowmetry confirmed that transdermal nitroglycerin and acetylcholine cause local increases in flow, but could not distinguish arterial and venous responses. The use of such micro-patches is disclosed in U.S. patent application Ser. No. 12/059,383, entitled ""MICRO-PATCH" FOR ASSESSMENT OF THE LOCAL MICROVASCULATURE AND MICROCIRCULATORY VASOREACTIVITY," filed Mar. 31, 2008, which is incorporated herein by reference. In accordance with the present invention, the hypotheses that was tested:

1a) Increases (↑) in AC and DC would differ significantly within each study agent;

1b) ↑DC/↑AC would differ significantly between the two study agents (consistent with their different pharmacologic activities); and 1c) The relationships between DC and AC at the Forehead would not differ significantly from literature reports of systemic volumes and changes thereof.

Such would suggest that the inventive embodiments can transform photoplethysmographic values at a central site such as the Forehead or Ear into a window that enables viewing the local microcirculation as a microcosm of the systemic circulation and its relative arterial and venous volumes.

The systemic challenge ($2^{nd}$ series) entailed sequestration of up to 1,500 ml blood in the lower extremities by progressive application of lower body negative pressure (LBNP), wherein it has been shown that decreases (↓) AC at a central site (Ear, Forehead) is comparable to ↓SV (measured in the periphery by voltage clamping), but assessments of venous volume and overall volume heretofore have not been achieved. It is hypothesized that:

2a) The LBNP-induced ↓DC (in $AC_{rest}$Mults) would correspond to the relative LBNP-induced "loss" of volume reported with this challenge;

2b) By linking AC to a measured (or estimated) systemic stroke volume ($SV_{rest}$Volume), we would be able, for the first time, to use the photoplethysmograph to quantify blood loss and blood replacement and, more specifically, to distinguish the arterial and venous components;

2c) Increases in AC and DC during recovery (upon release of negative pressure) would demonstrate a Frank Starling-like relationship with respect to the relationship of venous and arterial blood (as measured herein by photoplethsymography); and 2d) Comparative changes in DC and AC at finger and Ear would be consistent with homeostatic responses to blood loss (regional vasoconstriction, mobilization of blood from storage sites).

1$^{st}$ Series of Subjects: Local Interventions 10 healthy non-smoking volunteers were recruited and written informed consent was obtained. Each subject lay supine on a bed in a temperature regulated ~22° C. room. The Forehead was gently wiped with wet gauze and patted dry. Then, one of two drug "micro-patches" was prepared (based on randomized drug assignment to the first or second session (one hour apart). A nitroglycerin micro-patch was prepared by cutting a 1×1 cm section from a transparent commercial patch of standard concentration (Minitran, 3M Pharmaceuticals, Northridge, Calif.). A nicotine micro-patch was similarly prepared by cutting a 1×1 cm section from a transparent commercial patch of standard concentration (Nicoderm CQ, GlaxoSmithKline). The agents were selected because of their different modes of action (nitroglycerin being a nitric oxide donor at vascular endothelium, nicotine being a neurotransmitter at accessible pre-to-post ganglionic junctions) and their FDA-approved clinical availability as transparent transdermal patches. Each was available in a single concentration; hence equipotent doses were not sought in this initial investigation; however, comparisons of multiple doses of multiple drugs certainly could be achieved with the present invention.

In accordance with the randomized selection, the nitroglycerin or nicotine micro-patch was placed on the study site and promptly covered with an nonautocentering, nonrecalibrating reflectance photoplethysmograph interfaced via bridge amplifier to a data acquisition system (PowerLab, ADInstruments, Boulder Colo.) for sampling at 200 Hz for continuous recording with customized commercially available software (Chart 7.0, ADInstruments). A second photoplethysmograph was concurrently placed on contralateral forehead for control readings and subsequent zeroing. After a period of stabilization (~10 sec), baseline ("pre") readings were obtained. Ten minutes later (after attainment of micro-patch-induced plateau) "drug" measurements were recorded. As shown in FIG. 2, the raw signal was separated in AC and DC components by respectively applying high pass (>0.5 Hz) and low pass (<0.5 Hz) filters. (Other filters, such as band pass or notch filters, can similarly be employed so long as the same filtering window is used for all such monitoring within the given subject). The raw, AC and DC signals were exported to a spreadsheet; and $AC_{pre}$, $AC_{drug}$, $DC_{pre}$, and $DC_{drug}$ were determined from 10 second segments during "pre" and "drug" for each agent. $AC_{pre}$ and $DC_{pre}$ were recorded as the respective 10 second averages. $AC_{drug}$ and $DC_{drug}$ were recorded for 10 sec after attainment of a plateau (at approximately 10 min). In accordance with this invention, other intervals, including single beats, can be used.

To facilitate comparison between AC and DC and the relative impacts of nitroglycerin and nicotine within and among subjects, all data were converted as per the embodiment(s) of the present invention shown in FIG. 2 to $AC_{rest}$ Mults by normalizing each value to the $AC_{rest}$ Voltage (which was the same as the AC Calibration Voltage and the undisturbed $AC_{pre}$ value). For each successive reading, the # of $AC_{rest}$Mults was determined as per the description of FIG. 2 above.

$AC_{drug}$ as # of $AC_{rest}$MULTS='GIVEN $AC_{drug}$ VOLTAGE'×'1 $AC_{rest}$MULT/ $AC_{rest}$VOLTAGE'→GIVEN $AC_{drug}$VOLTAGE/ $AC_{rest}$VOLTAGE $DC_{drug}$ as # of $AC_{rest}$MULTS='GIVEN $DC_{drug}$ VOLTAGE'×'1$AC_{rest}$MULT/ $AC_{rest}$VOLTAGE'→GIVEN $DC_{drug}$VOLTAGE/ $AC_{rest}$VOLTAGE Conversion to $AC_{rest}$Mults enabled comparisons of ΔAC and ΔDC within and among drugs, within and among subjects. This was not attainable with monitors that solely focus on either the arterial (e.g. arterial blood pressure monitors) or venous (central venous pressure monitors) measurements or even with plethysmographic algorithms that perform contour analysis (since this is limited to the AC component). The inventive conversion to $AC_{rest}$Mults also enabled testing the hypothesis that ↑DC/↑AC ratio would be greater in response to nicotine than nitroglycerin. Since it is a direct nitric oxide donor, nitroglycerin would impact the vascular endothelium of all penetrable vessels beneath the micro-patch. Alternatively, the primary sites of action for nicotine would be nicotinic pre-/post-ganglionic receptors of the autonomic nervous system, of which only parasympathetic fibers synapse at the end organ; hence, nicotine should predominantly affect volume downstream of the innervated precapillary sphincter and hence spare more proximal arteries and meta-arterioles. This would constitute a vital means to assess local microcirculatory pharmacology and provide into systemic microcirculatory pharmacology in accordance with U.S. patent application Ser. No. 12/059,383, entitled "'MICRO-PATCH' FOR ASSESSMENT OF THE LOCAL MICROVASCULATURE AND MICROCIRCULATORY VASOREACTIVITY."

Drug impacts on pulsatile (~arteriolar capillary) and non-pulsatile (~venular) segments of the underlying microvasculature were further assessed by calculating changes in compliance as per the methodology outlined in FIG. 3. Respective compliance changes were determined by dividing the change in (Δ) AC and ΔDC (in $AC_{rest}$Mults) by 65 mmHg and 17.5 mmHg, consensus pressures at distal arterioles and venules (Best et al 1966, Intaglietta et al 1970). Since the numerator was a voltage-based measurement (not actual volume), the photoplethysmograph generated "ACcompliance" and "DCcompliance" values are expressed in "$AC_{rest}$Mults/mmHg" units (herein introduced).

Table 2, below, summarizes the drug-induced changes in AC in terms of raw voltage as well as $AC_{rest}$Mults (wherein $AC_{pre}$ constituted the $AC_{rest}$ reading). Without such normalization (conversion to $AC_{rest}$Mults), $AC_{pre}$ readings at the control site ranged from 0.0012 volts in our darkest to 0.0181 volts in our lightest subject—the wide range would complicate intersubject comparisons of drug effect. In accordance with the invention, the impact of attenuation on DC as well as AC was eliminated by normalizing to $AC_{rest}$. The mean raw AC values (volts) increased from $AC_{pre}$=0.0124 to $AC_{Nitro}$=0.0285 (p=0.0005) and $AC_{pre}$=0.0101 to $AC_{NIC}$=0.0291 (p=0.0001). Establishing $AC_{pre}$ as the $AC_{rest}$ Voltage=1 $AC_{rest}$Mult converted the $AC_{pre}$ and $AC_{drug}$ values to 1 and 2.55 $AC_{rest}$Mults for nitroglycerin and to 1 to 3.01 $AC_{rest}$Mults for nicotine. These amounted to relative increases (%↑) of 155% and 201%, respectively. Dividing Δ AC by 65 mmHg provided absolute increases in AC compliance of 0.0248 $AC_{rest}$Mults/mmHg and 0.031 $AC_{rest}$Mults/mmHg for the two agents.

TABLE 2

| Photoplehysmographic Values | Affected by Attenuation? | Affected by Background? | AC Nitro Mean ± SD | AC NIC Mean ± SD |
|---|---|---|---|---|
| Raw AC Values in volts: | | | | |
| $AC_{pre}$ | YES | No | 0.0124 ± 0.008 | 0.010 ± 0.01 |
| $AC_{drug}$ | YES | No | 0.0285 ± 0.016 | 0.029 ± 0.01 |
| ΔAC | YES | No | 0.0161 ± 0.011 | 0.019 ± 0.01 |
| AC Voltages Converted to $AC_{rest}$Mults (obtained by normalizing to voltage of ACpre): | | | | |
| $AC_{pre}$ (in $AC_{rest}$Mults) | No | No | 1 | 1 |
| $AC_{drug}$ (in $AC_{rest}$Mults) | No | No | 2.553 ± 0.946 | 3.01 ± 0.971 |
| ΔAC (in $AC_{rest}$Mults) | No | No | 1.558 ± 0.946 | 2.01 ± 0.97 |
| AC in $AC_{rest}$Mults Converted to ACcompliance (in $AC_{rest}$Mults/mmHg): | | | | |
| Δ$AC_{rest}$Mult compliance (in $AC_{rest}$Mults/mmHg) | No | No | 0.0239 ± 0.025 | 0.0309 ± 0.024 |

Likewise, Table 3 summarizes the drug-induced changes in DC in raw values as well as $AC_{rest}$Mults. The DC raw values (volts) increased from $DC_{pre}$=1.82 to $DC_{Nitro}$=1.93 and from $DC_{pre}$=1.41 to $DC_{NIC}$=1.68. Having established $AC_{pre}$ as the $AC_{rest}$ Voltage, the voltages converted to $DC_{pre}$ and $DC_{drug}$ values of 208.27 and 222.31 $AC_{rest}$Mults for nitroglycerin and to 175.22 and 204.77 $AC_{rest}$Mults for nicotine. Hence DC increased by 14.04±10.2 and 29.56±27.7 $AC_{rest}$Mults for nitroglycerin and nicotine respectively. This amounted to respective %↑DC of 6.42% and 23.41%, spuriously low because DC readings included background, which impacted the denominator ($DC_{pre}$) but not ΔDC (addressed below). Next, ΔCompliance was determined by dividing ΔDC by 17.5 mmHg. This provided ↑DC compliance of 0.80 $AC_{rest}$Mults/mmHg and 1.69 $AC_{rest}$Mults/mmHg for the two agents; in light of distorting impact of background on the denominator, %↑DCcompliance was not calculated.

The ΔDC/ΔAC ratios were 7.31±8.2 and 14.23±4.49 for nitroglycerin and nicotine, respectively (p=0.015 by one-tailed paired test for inter-drug differences), indicating that nicotine caused a significantly greater preponderance of DC (i.e., venous) dilation. The respective ↑DCcompliance/↑ACcompliance ratios were 33.56 and 54.57 for nitroglycerin and nicotine (p=0.046 for the greater ratio after nicotine).

TABLE 3

| Photoplethysmographic Values | Affected by Attenuation? | Affected by Background? | DC Nitro Mean ± SD | DC NIC Mean ± SD |
|---|---|---|---|---|
| $DC_{pre}$ | YES | YES | 1.824 ± 0.39 | 1.413 ± 0.54 |
| $DC_{drug}$ | YES | YES | 1.929 ± 0.35 | 1.676 ± 0.47 |
| ΔDC | YES | No | 0.11 ± 0.07 | 0.26 ± 0.14 |
| $DC_{pre}$ (in $AC_{rest}$Mults) | No | YES | 208.270 ± 128.28 | 175.22 ± 102.99 |
| $DC_{drug}$ (in $AC_{rest}$Mults) | No | YES | 222.3106 ± 138.471 | 204.77 ± 104.66 |
| ΔDC (in $AC_{rest}$Mults) | No | No | 14.0404 ± 14.87 | 29.56 ± 17.85 |
| ΔDC Compliance (in $AC_{rest}$Mults/mmHg)) | YES | No | 0.8023 ± 0.850 | 1.689 ± 1.02 |

Oft-cited reports in the literature that nitroglycerin caused a %↑ in venous compliance that was ~1.8 times the %↑increase in arterial compliance (Imhof 1980, Mackenzie 1977) provided the opportunity for testing whether photoplethysmograph monitoring of nitroglycerin micro-patch impact on the local microvasculature paralleled invasive assessments of intravascular nitroglycerin administration into systemic vessels that led to the designation of nitroglycerin as primarily a venodilator. However, to test whether the relative micro-patch induced changes were similar to the relative venous/relative arterial changes (%↑venous/%↑arterial) measured systemically, it was necessary to convert absolute measures of Δcompliance to measures of Δcompliance relative to prenitroglycerin measurements. The %↑AC and %↑ACcompliance were readily determined: the use of $AC_{rest}$Mults eliminated the impact of attenuation and AC is, in and of itself, independent of background. Conversely, the %↑DC and %↑DCcompliance were not readily determinable: the ↑$DC_{nitro}/DC_{pre}$ ratio was confounded by the predominant impact of background.

Figure 4:
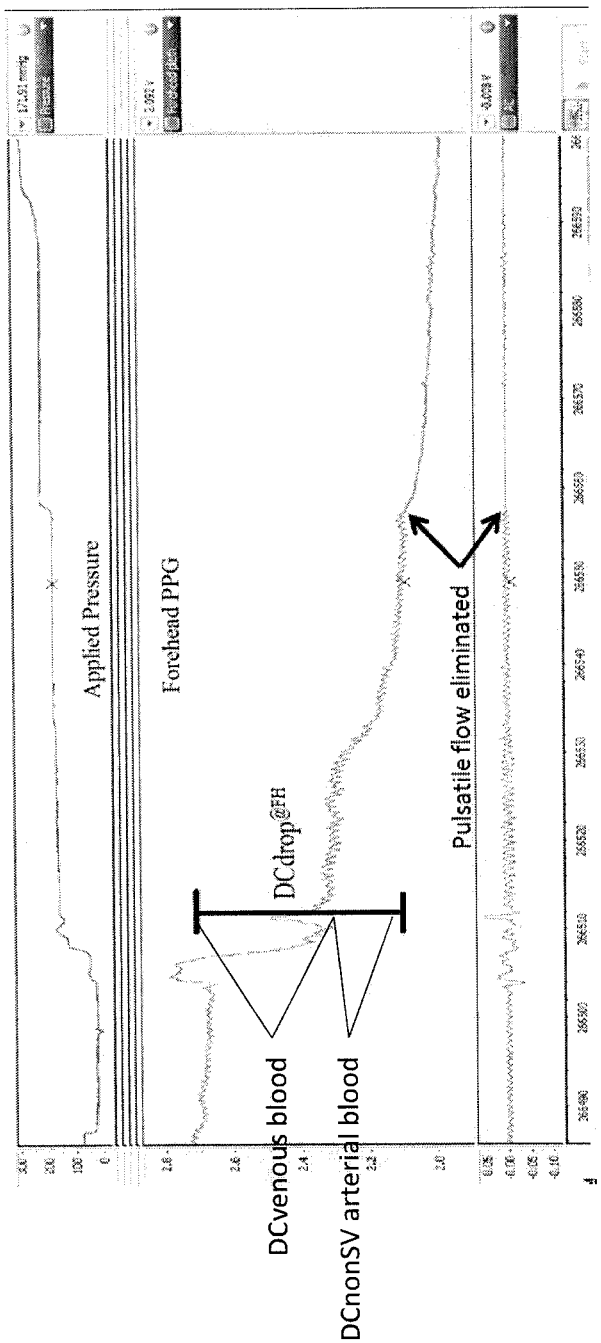
FIG. 4 is a graph of a plethysmographic signal showing means for isolation of DCblood from DCbackground and further distinguishing the former into $DCblood_{venous}$ and $DCblood_{nonSV\ arterial}$ in accordance with the present invention.

The present method and system address this with mechanisms to isolate what is herein termed "DCblood" from "DCbackground" (FIGS. 4-6); prior to the present invention, these were assumed to be inseparable components of the photoplethysmographic signal. A mechanism for isolating the DCblood component from the DCbackground component was therefore introduced. As shown in FIG. 4, in the final six subjects, increasing pressure was applied to the photoplethysmograph at the untreated control site. Application of slowly increasing pressure caused progressive displacement of capillary, venous, arteriole and arterial blood to the point that vascular volume no longer contributed to the photoplethysmograph signal.

The progressive application of pressure to eliminate blood beneath the photoplethysmograph was chronicled via a pressure transducer mounted atop the photoplethysmograph sensor (top panel of FIG. 4). Progressive decline in the plethysmograph are shown for the raw photoplethysmograph signal (middle panel) and AC component (isolated in bottom panel with a 0.5 to 3.0 Hz digital band pass filter). The drop in voltage until loss of the pulsatile signal represented the DCblood component. The remaining voltage represented background. It also can be seen in FIG. 4, the DCblood is really a composite of what I herein introduce as $DCblood_{venous}$ and $DCblood_{nonSV\ arterial}$. $DCblood_{venous}$ is the blood that is eliminated beneath photoplethysmograph by applied pressure that is not sufficient to compress arteries and arterioles (as shown by persistence of pulsatie signal in bottom channel of FIG. 4). $DCblood_{nonSV\ arterial}$ is shown by volume that is displaced between the initial displacement of venous blood and the ablation of the pulsatile signal. The last component to be ablated is generated by the pulsatile delivery of the SV (AC component of photoplethysmograph). The signal which remains is DCbackground, the contribution to the signal by nonblood tissues. These different parameters have different uses: comparison of AC and $DCblood_{venous}$ is applicable to a setting such as the present comparison of arterial and venous impacts of a vasoactive medication. Changes in systemic volume, as per the model of simulated blood loss (lower body negative pressure) described below, may best be assessed by SV and DCblood (i.e, $DCblood_{venous} + DCblood_{nonSV\ arterial}$).

Figure 5:
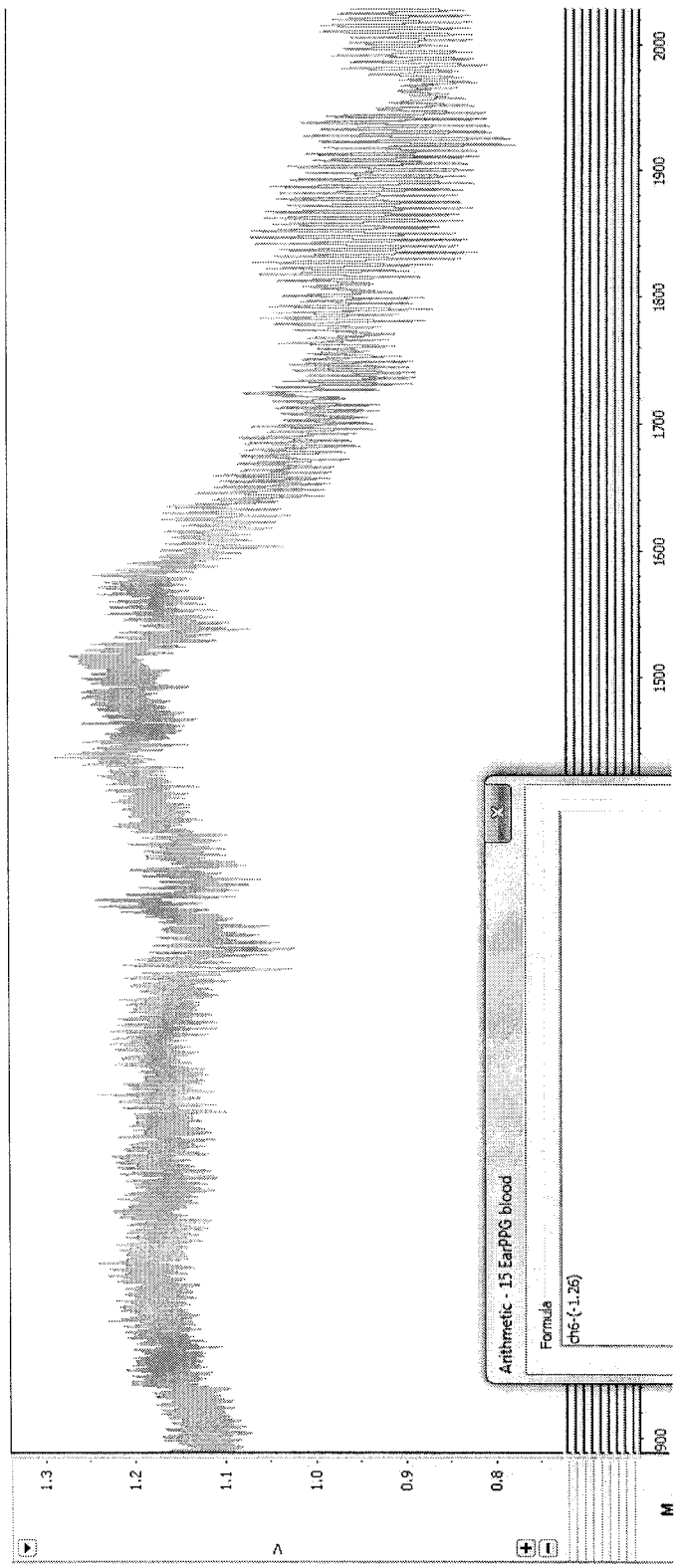
FIG. 5 shows the signal from the lower panel of FIG. 1 with the DCbackground component subtracted such that PPGblood (DCblood+SV) is graphed.

The voltage decline associated with loss of all pulsations is defined as $DCblood_{rest}$. This was quantified in $AC_{rest}$Mults, wherein $AC_{pre}$ prior to the application of pressure was the $AC_{rest}$ Voltage and $DCblood_{rest}$ is the drop caused by external pressure at an otherwise "resting" site. The remaining signal was DCbackground. In addition, as shown in FIG. 5, subtracting DCbackground from all photoplethysmograph readings enables continuous display of DCblood values (as opposed to only DCblood at the given time point (typically at rest). In essence, DC blood is equivalent to the blood component of the raw photoplethysmographic signal (PPGblood) minus the contribution of the stroke volume (i.e., minus 1 $AC_{rest}$Mult).

In the present series of subjects, based on intersite similarity among forehead sites, the $DCblood_{rest}$ value (in $AC_{rest}$Mults) determined at the control site was utilized as the $DCblood_{pre}$ value at the contralateral drug site (so as to avoid the need to press on and thereby disturb the drug site). When expressed as $AC_{rest}$Mults to facilitate intersubject comparison, $DCblood_{venous}$ averaged 25.6±18.4 $AC_{rest}$Mults. This value was independent of background (independence achieved by aforementioned zeroing) as well as attenuation (independence achieved by converting to $AC_{rest}$Mults). The remaining signal constituted DCbackground+ $DCblood_{nonSV\ arterial}$; the latter, which was not the focus of our micropatch assessments, averaged 5 $AC_{rest}$Mults.

As related in FIG. 6, the introduction of DCblood enabled measurement of relative as well as absolute measures of DC and ΔDC as well as of DCcompliance and ΔDCcompliance; this integrates determination of $DCblood_{rest}$ with the embodiment(s) of FIGS. 2 and 3. Dividing ΔACcompliance by $AC_{pre}$ in $AC_{rest}$Mults and dividing ΔDCcompliance by $DCblood_{pre}$ in $AC_{rest}$Mults identified a %↑DCcompliance/ %↑AC compliance (per $AC_{rest}$Mults) ratio that was 1.824±1.32 (p—0.009 by one-tailed paired t-test for AC vs DC difference) (Table 4). The 95% confidence interval ("CI") of 0.816 clearly encompassed the literature reports of a Δvenous/Δarterial compliance ratio=1.8.

TABLE 4

| Photoplethysmographic Values | AC | Traditional DC (=DCblood + DCbackground) | DCblood |
|---|---|---|---|
| Pre (in $AC_{rest}$Mults) | 1 | 228.036 ± 141.5 | 25.547 ± 18.37 |
| Δ Drug - Pre (in $AC_{rest}$Mults) | 1.822 ± 0.452 | 17.785 ± 6.51 | |
| Δ Drug - Pre (in $AC_{rest}$Mults/mmHg) (based on literature-derived pressures of 65 mmHg and 17.5 mmHg for AC and DC vascular beds, respectively) | 0.0248 ± 0.02 | n/a | 1.016 ± 0.94 |
| ΔCompliance/Pre | .0248 ± 0.017 | n/a | 0.048 ± 0.0494 |

It should be noted that related applications in the spirit of the present invention include utilizing the pressures required for eliminations of $DCblood_{venous}$ and $DCblood_{nonSVarterial}$ as a pressure components of measures of compliance. It also should be noted that drugs and doses are not limited to those employed above. For example, application of eutectic mixture of local anesthetic (EMLA) generated a ↑DC/↑AC ratio of 13.6. This is consistent with it being a dilator of smooth muscle and thus more likely to have a relatively larger impact on AC than nitroglycerin or nicotine.

DESCRIPTION OF ADDITIONAL EMBODIMENTS

Figure 7:
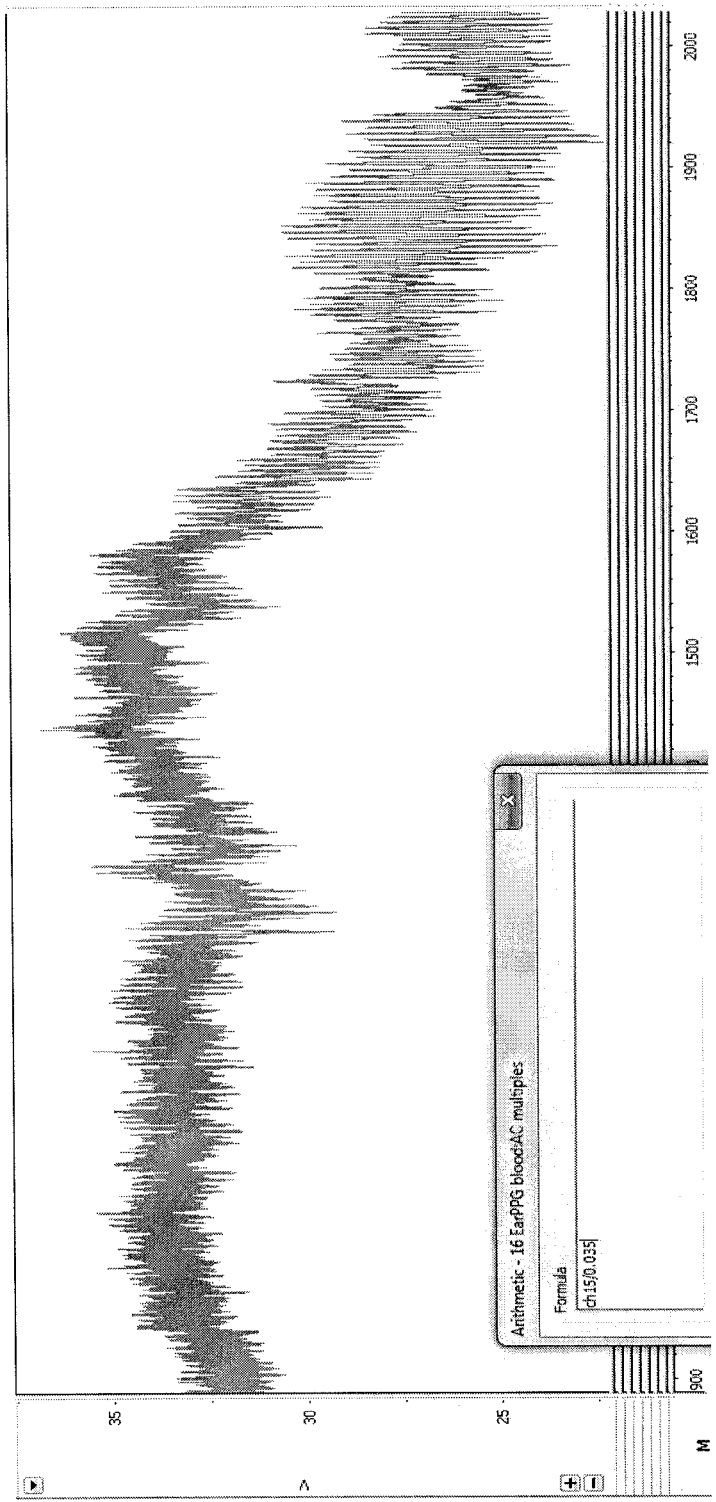
FIG. 7 shows how, using embodiments of the present invention, the continuous DCblood signal is converted from a graph of voltages to a graph of $AC_{rest}$Mults.
Figure 8:
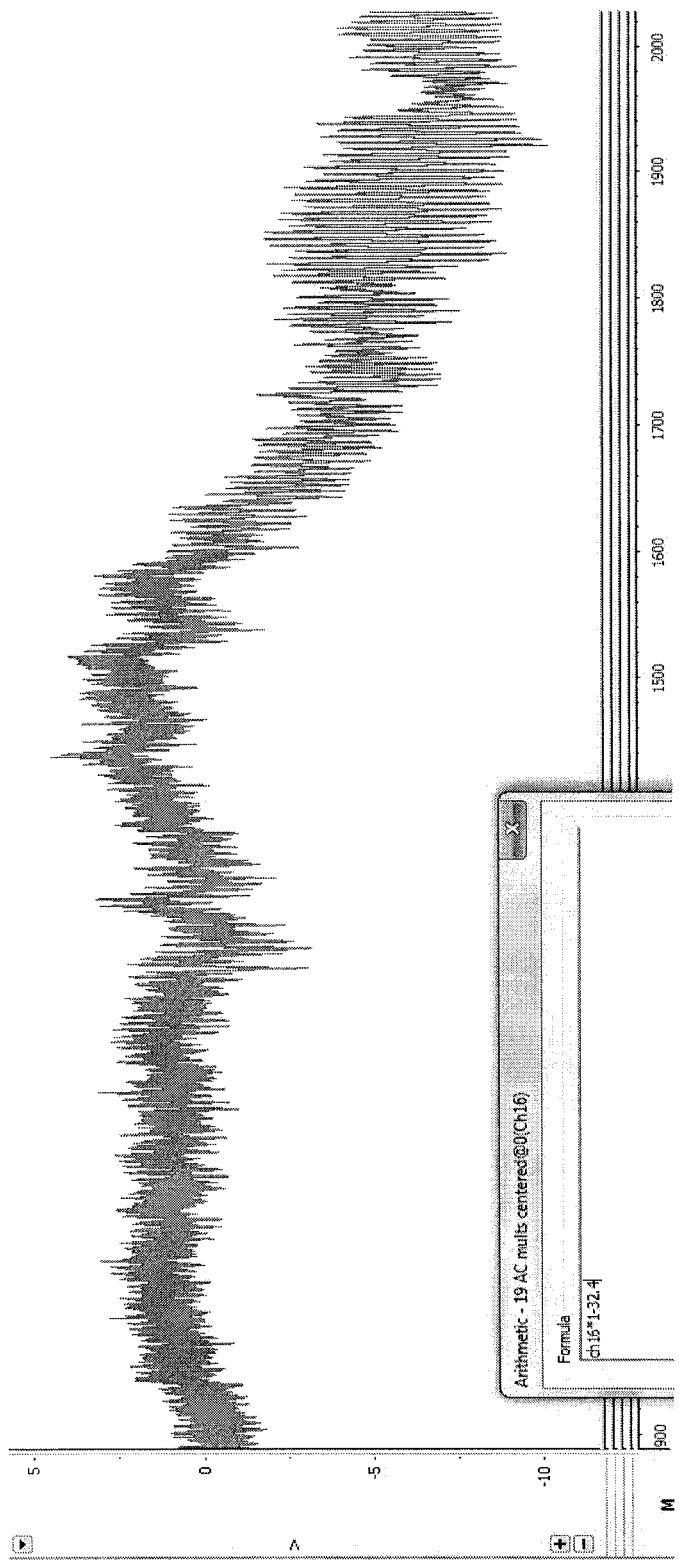
FIG. 8 shows the tracing of FIG. 7 with an offset so that baseline is centered at 0.
Figure 9:
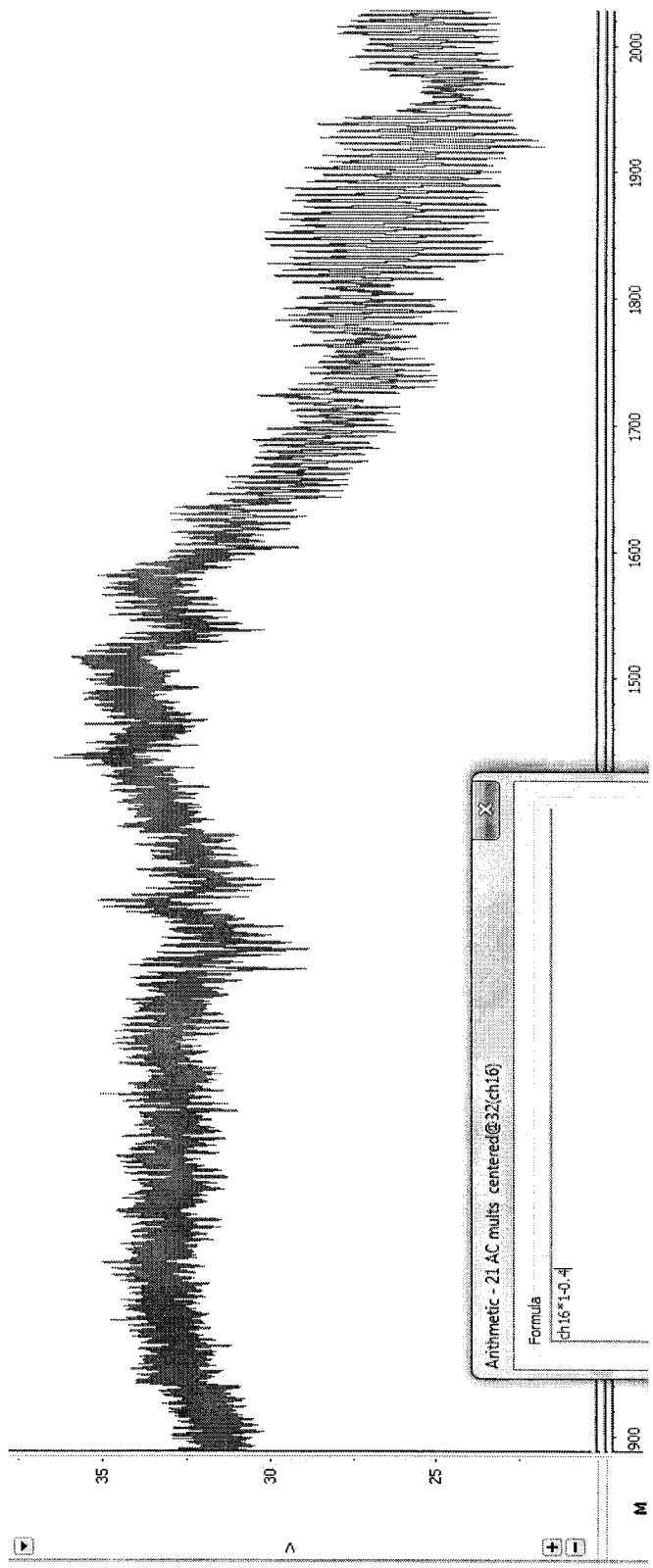
FIG. 9 shows the tracing of FIGS. 7 and 8, centered at 32 on the y-axis, a value that is amenable to consistent display among patients, since resting volume in healthy subjects is ~32 $AC_{rest}$Mults.

FIGS. 7-9 show the impact of embodiments of the present invention on photoplethysmographic waveforms and their AC and DC components. In many of such applications, the conversion is inherently obvious (i.e., simply based on conversion of voltage to $AC_{rest}$Mults). However, especially as one seeks uniform axes for display (as enabled by inventive conversion to uniform units), it is preferred to rely on an equation for determining variables and subsequent graphing. This integrates inventive embodiments as components of the equation for a straight line. For example, establishment of a means for consistent display of photoplethysmographic data within and among subjects can be achieved with an inventive conversion factor and determination of the desired value of y-axis crossing in $AC_{rest}$Mults (Table 5).

The second channel (labeled 14) has isolated the AC signal via high pass filter. As expected, the magnitude of the AC signal decreased with progressive lower body negative pressure and then rebounded upon release of the negative pressure. The third channel (labeled 15) has converted the raw voltage of first channel 6 to $AC_{rest}$Mults as may be accomplished by dividing the voltage of each data point ($AC_{GivenTimePoint}$ Voltage) by the $AC_{rest}$ Voltage. The fourth channel (labeled 16) shows the continuous $AC_{rest}$Mults after the pre-LBNP mean (in volts) has been subtracted from the signal.

Figure 10:
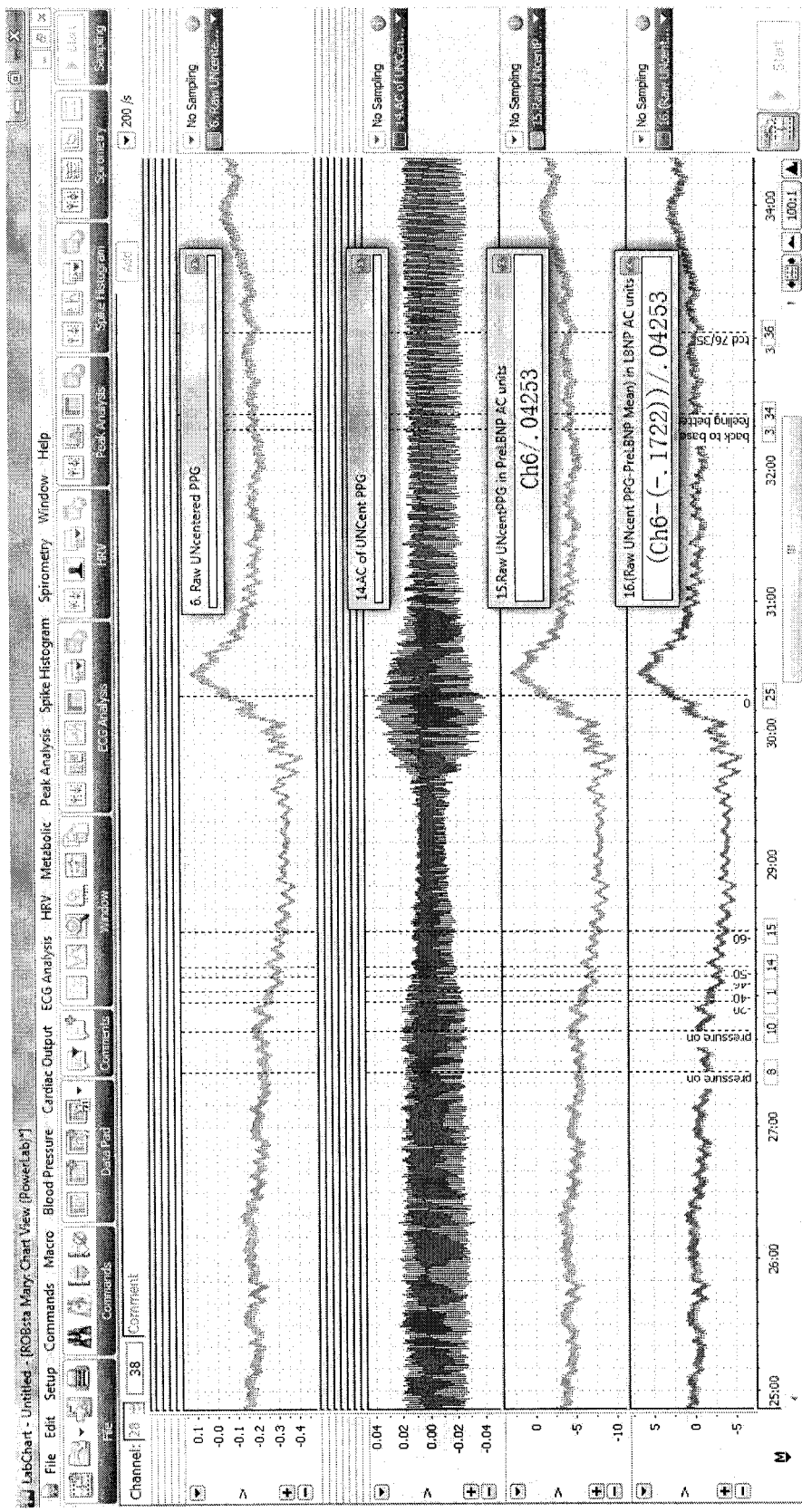
FIG. 10 is a screen shot of a multichannel data acquisition system, showing four channels that have been adapted to show multiple synchronous configurations of the same signal from an ear photoplethysmograph.
Figure 11:
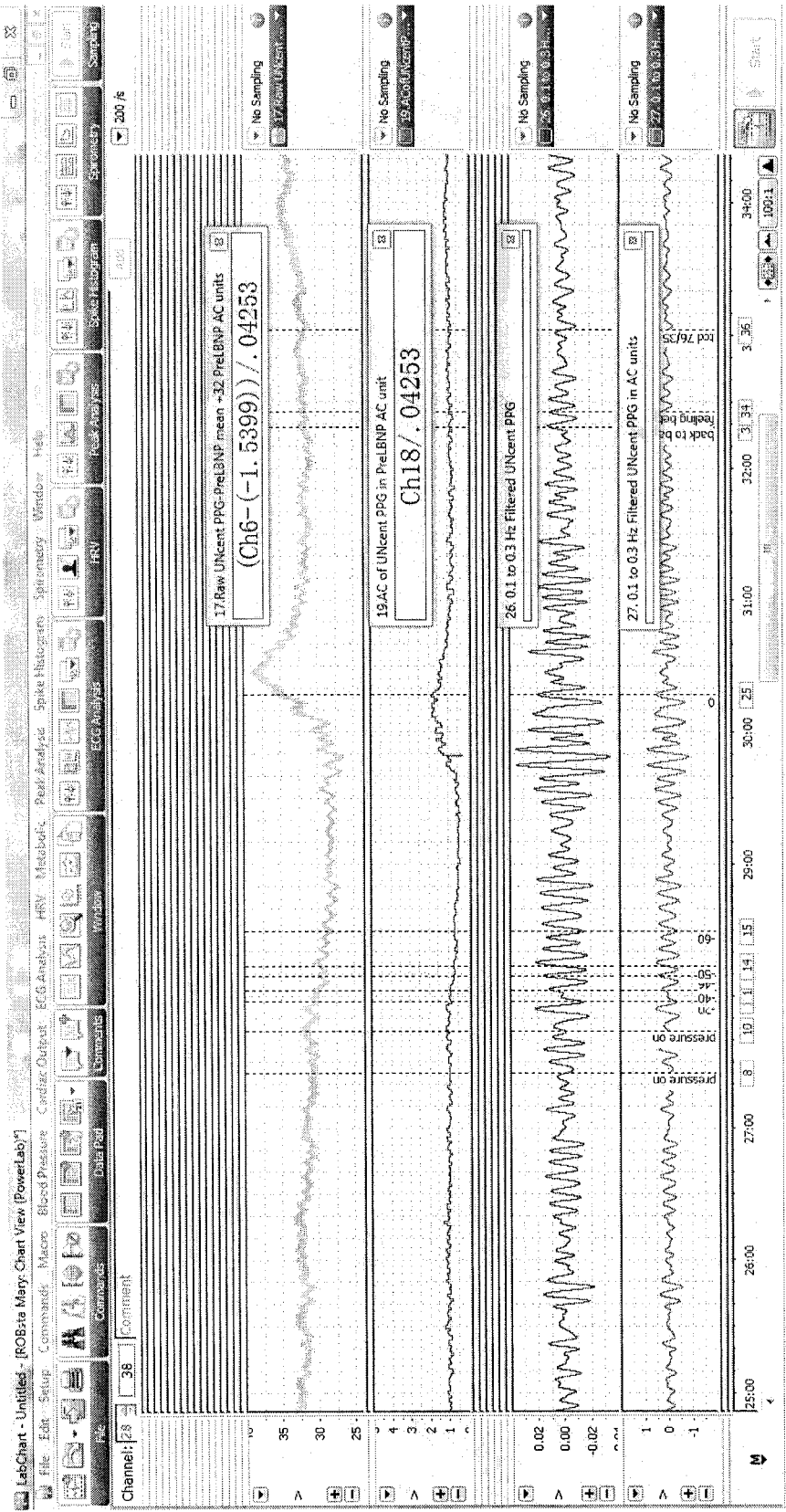
FIG. 11 shows additional manipulations of the $AC_{rest}$Mults tracing shown in FIG. 10.

FIG. 11 shows a changed Y-axis crossing, to approximately 32 $AC_{rest}$Mults, to represent starting at full volume in the given subject as detailed below, thereby providing more relevant information than the raw voltage (see first channel of FIG. 10). The second channel (labeled 19) shows data of the AC channel after conversion to $AC_{rest}$Mults. The third channel shows continuous data after filtering at 0.1-0.3 Hz so as to focus on the section of DC predominantly influenced by respiration (but not the entire DC, which would be captured by looking at <0.5 Hz). The fourth channel shows how this can be expressed in $AC_{rest}$Mults. This enables viewing AC and DC in common units for such view, as well as for calculations (e.g., of relative magnitudes and variabilities in different study phases) and for spectral domain analysis (shown below).

It should be noted that the aforementioned text and descriptions have focused on voltages, $AC_{rest}$Mults,

TABLE 5

Desired, Established, Given and Sought Values for Uniform Display of Data in $AC_{rest}$Mults

| y = desired value in $AC_{rest}$Mults of y-axis crossing | m = established conversion factor to convert data to $AC_{rest}$Mults (=1 if data already in $AC_{rest}$Mults) | x = stable baseline (@rest) value of given photoplethysmograpic output | Solving for b, which is offset in $AC_{rest}$Mults required to achieve desired y-axis crossing in $AC_{rest}$Mults |
|---|---|---|---|
| If data already in $AC_{rest}$Mults: | | | |
| 0 $AC_{rest}$Mult | 1 | Data in $AC_{rest}$Mults | =−mx |
| 32 $AC_{rest}$Mults | 1 | Data in $AC_{rest}$Mults | =−mx + 32 |
| If data in volts: | | | |
| 0 $AC_{rest}$Mult | 1 $AC_{rest}$Mult/$AC_{rest}$Voltage | Data in Volts | =−mx |
| 32 $AC_{rest}$Mults | 1 $AC_{rest}$Mult/$AC_{rest}$Voltage | Data in Volts | =−mx + 32 |

Subsequent graphing of continuous tracing would generate "y" at each time point based on established "m" multiplied by changing "x" (i.e., changing photoplethysmographic values over time) + calculated "b" (as per Table 5).

FIGS. 7-9 demonstrate some of the options for such displays.

FIGS. 10 and 11 show how multiple configurations of the same signal can be displayed in synchrony. FIG. 10 shows four channels as may be recorded simultaneously during a lower body negative pressure challenge (or subsequently created from an existing channel during post-collection processing). The initial baseline (preLBNP) section is to the left. Then, as shown by the dotted lines, lower body negative pressure was applied to as low as −60 mmHg. Then, at a little after 30 minutes, the pressure was released, and the recovery phase was entered. (The details of the lower body negative pressure challenge will be described below).

For each of the channels, the left-hand vertical axis represents the magnitude of the signal. The horizontal axis represents time (25:00 to 34:30 minutes). As can be seen by the series of horizontal lines running between the first and second channels, up to 16 channels were recorded during the study, but only four are shown herein. All represented data are from nonautocentering photoplethysmographs.

DCblood and compliance and related graphic displays. Much of the remainder of this section will focus on conversion of the photoplethysmographic signal to a measure of volume To further test whether the relationship between $DCblood_{rest}$ and $AC_{rest}$ of the photoplethysmograph measurement at the Forehead (PPG@FH) constitutes a microcosm of the relationship between capillovenous volume (CVV) and stroke volume (SV) of the systemic circulation and thereby adapt the photoplethymogram to quantify volume (in "$ml_{PPG}$"), I elected to convert photoplethysmograph readings to measurements of volume. In a preferred embodiment to achieve this heretofore unattainable measurement, $AC_{rest}$ is converted to a volume measurement based upon a measured "$SV_{rest}$" in ml (e.g., by echocardiography) or estimated $SV_{rest}$ in ml (based upon population estimates from others who have undergone echocardiographic measurements). The PPG to volume conversion factor (CF) at rest for all data points is determined as follows:

a) For data already converted to $AC_{rest}$Mults:
CF: $SV_{rest}$Volume/$1AC_{rest}$Mult
Volume (in $ml_{PPG}$) for a given AC or DC measurement:
=current # of $AC_{rest}$Mults×CF
=current # of $AC_{rest}$Mults×'$SV_{rest}$ in ml/$1AC_{rest}$Mult'
And if $SV_{rest}$ is known, e.g. 125 ml, then
=current # of $AC_{rest}$Mults×'125 ml/$1AC_{rest}$Mult'
b) One also could relate $SV_{rest}$Volume/$AC_{rest}$ Voltage, such that Volume in $ml_{PPG}$:
=current voltage×'$SV_{rest}$ in ml/$AC_{rest}$ Voltage'
And if $SV_{rest}$ is known, e.g. 125 ml, then
=current voltage×'125 ml/$AC_{rest}$ Voltage'
The conversion is summarized in FIG. 12; a sample calculation is shown in FIG. 13.

As per displaying in $AC_{rest}$Mults in Table 5, establishment of a means for consistent display of photoplethysmographic data within and among subjects in $ml_{PPG}$ can be achieved with an inventive conversion factor and determination of the desired $ml_{PPG}$ value of y-axis crossing for DCblood (consisting of $DCblood_{venous}$ and $DCblood_{nonSV\ arterial}$) in $ml_{PPG}$ (Table 6). Assume measured $SV_{rest}$=125 ml.

TABLE 6

Desired, Established, Given and Sought Values for Uniform Display of Data in mlppg

| y = desired value in $ml_{PPG}$ of y-axis crossing | m = established conversion factor to convert data to $ml_{PPG}$ (=1 if data already in $ml_{PPG}$ | x = baseline (@rest) value of given photoplethysmograpic output | Solving for b, which is offset in $ml_{PPG}$ required to achieve desired y-axis crossing in $ml_{PPG}$ |
|---|---|---|---|
| *If data already in $ml_{PPG}$:* | | | |
| 0 $ml_{PPG}$ | 1 | Data in $ml_{PPG}$ | =−mx |
| 4000 $ml_{PPG}$ | 1 | Data in $ml_{PPG}$ | =−mx + 4000 |
| *If data in $AC_{rest}$Mults:* | | | |
| 0 $ml_{PPG}$ | 125 ml/1 $AC_{rest}$Mult | Data in $AC_{rest}$Mults | =−mx |
| 4000 $ml_{PPG}$ | 125 ml/1 $AC_{rest}$Mult | Data in $AC_{rest}$Mults | =−mx + 4000 |
| *If data in volts:* | | | |
| 0 $ml_{PPG}$ | 125 ml/$AC_{rest}$Voltage | Data in Volts | =−mx |
| 4000 $ml_{PPG}$ | 125 ml/$AC_{rest}$Voltage | Data in Volts | =−mx + 4000 |

Subsequent graphing of continuous tracing would generate "y" at each time point based on established "m" mutlipled by changing "x" (i.e., changing photoplethysmographic values over time) + calculated "b" (as per Table 6).

If a calibrating measurement was not previously obtained at rest, then as previously alluded to with reference to FIG. 2, it can be derived based upon the stroke volume at the given time point based on the aforementioned relationship that $SV_{rest}$=1 $AC_{rest}$Mult. The $SV_{@GivenTimePoint}/SV_{rest}$ corresponds to $AC_{@GivenTimePoint}/AC_{rest}$ (i.e., to the number of $AC_{rest}$Mults or fractions thereof) at given time point; i.e., in the absence of local distortions, a decrease in systemic SV of 50% from $SV_{rest}$ would be accompanied by a decrease in $AC_{rest}$Mults by 50%. This relationship could be used as the basis for subsequent assessments in the absence an $AC_{rest}$ Voltage: one could record the $AC_{@GivenTimePoint}$ Voltage for the $SV_{@GivenTimePoint}$Volume, (i.e. for the SV used for calibration at the given time point). However, it would be preferable for interparameter, intersite and intersubject consistencies if $AC_{@GivenTimePoint}$ Voltage was extrapolated to the "universal" $AC_{rest}$ Voltage which then would correspond to 1 $AC_{rest}$Mult. In most cases, if the $SV_{rest}$ is not known from a prior echocardiographic measurement (e.g., in a cardiologist's office), then $SV_{rest}$ can be estimated from population values. Assuming that the value assigned to $SV_{rest}$=100 ml (as opposed to 125 in many of our robust volunteers) and that the $SV_{@GivenTimePoint}$=current SVstroke=70 ml, then the following relationship is established:

# of $AC_{@GivenTimePoint}$Mults/1 $AC_{rest}$Mult=70 ml/100 ml.

Hence, the $AC_{@GivenTimePoint}$ Voltage would correspond to 0.7 $AC_{rest}$Mults. It can then be extrapolated to $AC_{rest}$ Voltage as follows:

$$0.7/1 = AC_{@GivenTimePoint}\ Voltage/AC_{rest}\ Voltage,$$

where the $AC_{@GivenTimePoint}$ Voltage is the current AC voltage.

Figure 36:
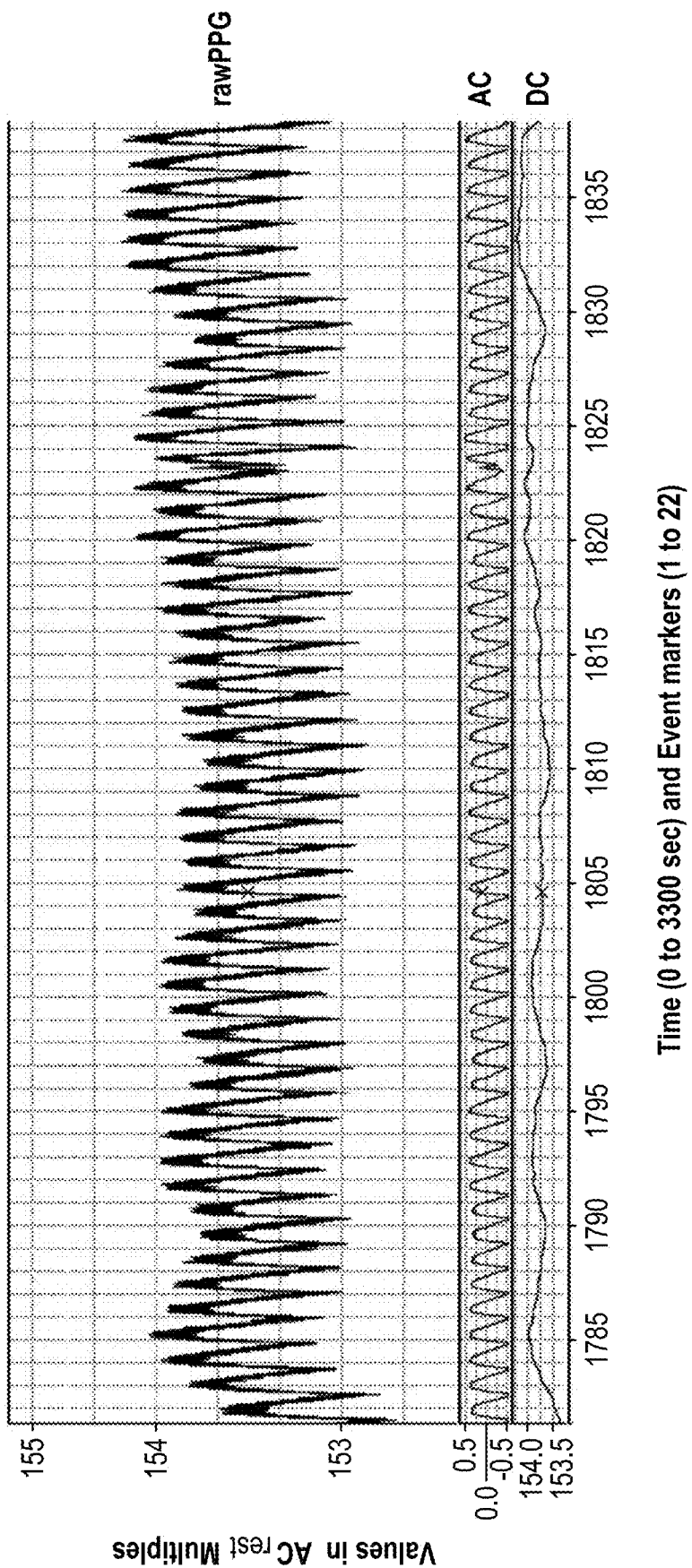
FIG. 36 is a screen shot showing 60 seconds selected for analysis during Flat for rawPPG in $AC_{rest}$Mults, AC in $AC_{rest}$Mults and DC in $AC_{rest}$Mults.

Next, using an estimated $SV_{rest}$ of 125 ml (based upon measurements in young healthy subjects and other young, healthy subjects or the literature), inventive conversion is herein used to determine the $AC_{@rest}$ and DCblood $ml_{PPG}$ values for the six subjects in whom DCblood (in voltage and converted to $AC_{rest}$Mults) was determined by application of external pressure (as shown in FIG. 4). Since $AC_{rest}$ was established as equivalent to $SV_{rest}$, then 1 $AC_{rest}$Mult represents 125 $ml_{ppg}$. DCblood conversion to volume was accomplished by two equivalent methods described above:

1) Conversion of DCblood voltage to # $AC_{rest}$Mults, with subsequent multiplication of # of $AC_{rest}$Mults by the aforementioned conversion factor ($SV_{rest}$/1 $AC_{rest}$Mult); or
2) Dividing $DCblood_{rest}$ voltage/$AC_{rest}$ Voltage, with subsequent multiplication by $SV_{rest}$ Based on the aforementioned documentation that $DCblood_{venous}$=25.6±18.4 $AC_{rest}$Mults (according to the method shown in FIG. 4), this indicates that, if $SV_{rest}$=125 ml, then DCblood=~3200 $ml_{PPG}$. [As will be utilized in the context of lower body negative pressure, one also can calculate that the mean resting nonpulatile volume, which is virtually the entire systemic volume as =~125×32=~4000 $ml_{PPG}$] The reasonableness of this approach for assessing venous volume is supported by the literature: a classic text relates that the cumulative volume in systemic venous circulation is ~3250 ml, as distributed among capillaries (300 ml), venules (350), veins (2100), vena cavae (350) and right atrium (150) [Best C H and Taylor N B, *The Physiologic Basis of Medical Practice*, 8$^{th}$ ed, The Williams and Wilkins Co., Baltimore 1966; FIG. 36.1 A and 36.1 B.] To minimize bias, the literature was accessed after my determination based on the photoplethysmographic-derived volumes in accordance with the embodiments introduced herein.

Further suggestion that the present embodiments enable the forehead microvasculature to be viewed as a microcosm of the systemic circulation is the observation that the 'DCblood)/AC' ratio of 25.6/1 under resting conditions at the Forehead (i.e., DC in $AC_{rest}$Mults) is comparable to to the systemic 'capillovenous ml/SV ml' ratio (3,250/125) =26). This was well within the 95% confidence limits (11.63) of the forehead ratio of 25.6±18.4.

Once the DC/AC relationship (e.g. ~25.6/1) has been established in a large number of healthy subjects, with potential adjustment for less robust individuals, then one could approximate relative as well as absolute changes in volume simply based on change in $AC_{rest}$Mults (i.e., changes in voltage relative to the $AC_{rest}$ Voltage). Conversion to volume can be achieved by the inclusion of a measured or estimated stroke volume (as shown below in a model of simulated blood loss).

In a preliminary assessment of the universality of the $DCblood_{rest}/AC_{rest}$ relationship, the DCdecline in $AC_{rest}$Mults was also measured while applying pressure to the photoplethysmograph measurement at the Ear (PPG@Ear). This was more difficult to achieve than at the Forehead primarily as a consequence of movement artifact (which likely may be excluded through bioengineering such as inclusion of additional filters to identify specific tissues and substrates and by including means of artifact rejection). Zeroing at the Ear was accomplished by squeezing the photoplethysmograph and underlying lobe between two fingers (after covering the contralateral surface with black tape so as not to include the investigator's finger in the measurement field). Attempts to similarly displace blood from the finger were complicated by the thickness of the potential light path, thereby necessitating pronounced squeezing of the tissues and consequent reorientation of the photoplethysmograph during the zeroing process. An alternative method was therefore relied upon—with the arm held elevated at 90° for 30 seconds, I compressed the brachial artery until pulsations were no longer apparent; the DC decline amounted to DCblood. The DCblood/AC ratios were determined at the respective sites.

The likelihood of similar relationships throughout the body was suggested by the finding that DCblood/AC ratios based upon zeroing at the Ear and finger averaged ~24 $AC_{rest}$Mults and 22 $AC_{rest}$Mults, respectively (encouraging, especially since the finger is subject to greater autonomic impact).

Thus, the present invention has identified the means to and value of distinguishing AC and DC components of the photoplethysmograph and of limiting the impact of attenuation and background. Moreover, it also has provided means to achieve these aims with basic technologies. However, it should be appreciated by those experienced in this field that, now that the value of this has been shown, it would be of value to improve present means and develop additional means to implement the invention(s). The former may include improved filtering and artifact rejection and related means to improve the zeroing process; many such features are available in commercial devices (which could be modified to enable inactivation of autocentering and dynamic recalibrating algorithms). The latter may include other means that can be modified for separation of the AC and DCblood components introduced herein. Such isolation can be aided by, as well as enable, determination of the concentrations of substrates and metabolic products in the arterial and venous compartments. For example, the importance of distinguishing arterial and venous oxygen saturation has previously been emphasized; this would be facilitated by quantitative separation of AC and DCblood as described herein. Similarly, one could assess amounts of glucose and carbon dioxide. Conversely, if one knows amounts and concentrations in both vascular beds, s/he can determine relative volumes. Alternative means of separation include concurrent assessment of cell velocity (as by including principles of laser Doppler flowmetry). Additionally, one could refine study models to deliberately eliminate the arterial or venous component by focused component extinction.

$2^{nd}$ Series of Subjects: Simulated Systemic Hypovolemia with Lower Body Negative Pressure:

Documentation of the similarity between $DC_{rest}/AC_{rest}$ @Forehead (or Ear) and $CVV_{rest}/SV_{rest}$ of the systemic circulation led to postulation that, by converting photoplethysmograph voltage at a central site to $ml_{PPG}$, systemic blood loss during progressive hypovolemia (as opposed to simply locally induced changes) could be quantified. A progressive lower body negative pressure (LBNP) protocol was utilized because it enables progressive hypovolemia (typically commensurate to loss of 500 to 1500 ml) to be simulated in a noninvasive, readily reversible manner. In addition, in the absence of an established gold standard for directly quantifying blood loss (other than weighing buckets and sponges), the established correlation of degree of negative pressure with measured blood loss enabled testing photoplethysmographic determinations at specified degrees of lower body negative pressure (with established amounts of simulated loss and restoration thereof).

Twelve healthy volunteers ranging in age from 23 to 30 underwent a lower body negative pressure protocol which consisted of lying supine with the pelvis and hips in an airtight chamber. Monitoring included:
continuous EKG and continuous noninvasive finger arterial blood pressure;
three photoplethysmographs: noncentering, noncalibrating photoplethysmographs as described above.

The Ear was selected for central photoplethysmograph monitoring because it is a common site of pulse oximetry. After baseline measurements were obtained, negative pressure was progressively applied via the lower extremity chamber until one or more of the following safety endpoints:
light-headedness or other evidence of altered mental state;
decrease in blood pressure mean by >20%;
change in heart rate of >50%; or.
subject discomfort Photoplethysmographic readings were recorded (and AC and DC components distinguished) at the Finger and Ear prior to the onset of ("pre") and during the challenge. Prior to analysis, AC@rest was recorded at each site and all voltages were subsequently converted to $AC_{rest}$Mults based upon the AC@rest at the given site in accordance with the present invention.

The rate of subsequent release of lower body negative pressure ("recovery") was titrated to improvement of signs and symptoms, while seeking to avoid precipitous rises in blood pressure and reflexive decline in heart rate.

In light of concerns that rapidly changing volume status and the impact of lower body negative pressure on breathing patterns, it was chosen not to rely on distinguishing AC and DC by the composite filtering used for the earlier micropatch investigation. Instead, as described in FIG. 2, a peak analysis module (LabChart 7.0, ADInstruments, Boulder Co.) was utilized to identify each beat and then isolate the peak and trough, with DC being taken as the trough and AC calculated as the "peak minus trough" difference for each identifiable beat. For purposes of this investigation, the minor difference between the DC determinations in the two series of subjects were disregarded.

Figure 16:
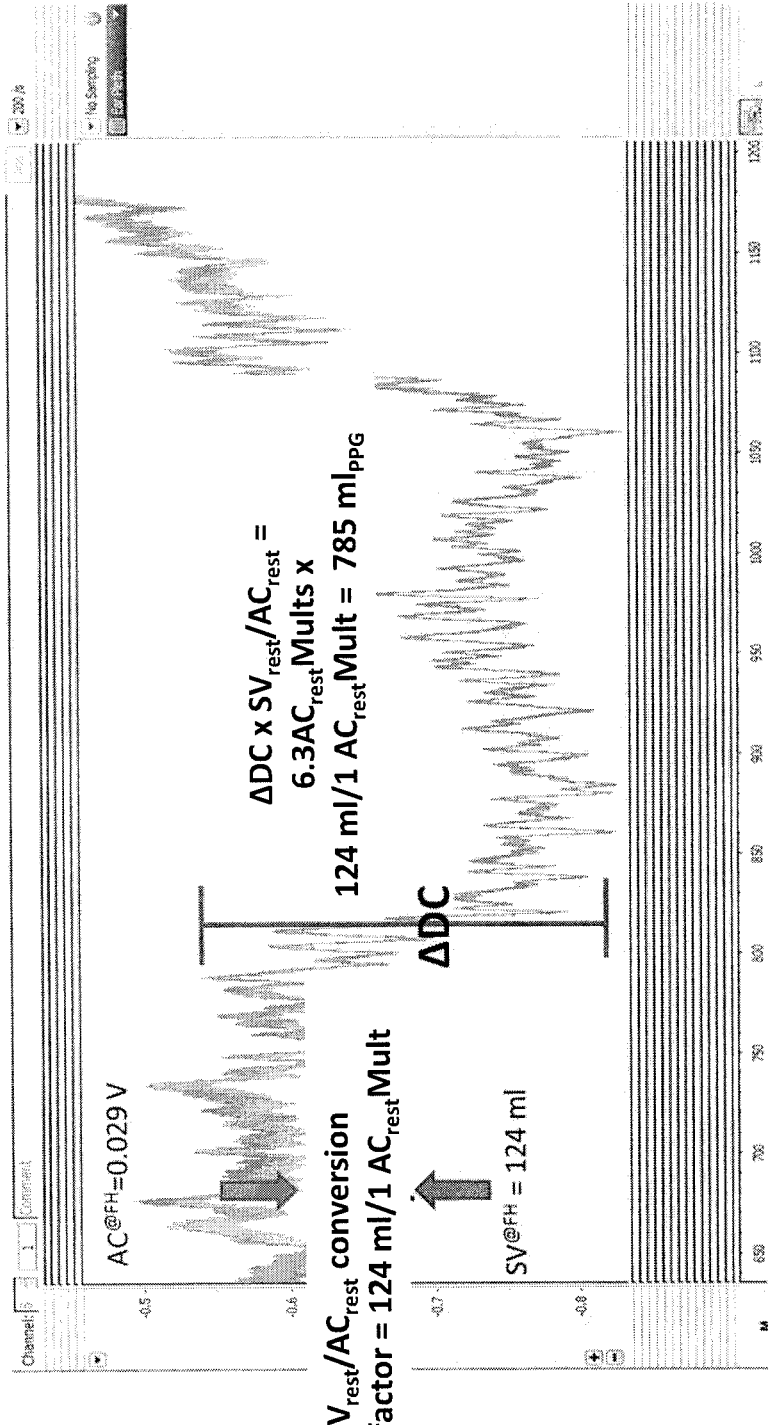
FIG. 16 is a graph of a photoplethysmograph on a subject undergoing lower body negative pressure which illustrates conversion of a decline in $AC_{rest}$Mults to a decline in volume based upon $SV_{rest}$Volume/1 $AC_{rest}$Mult conversion factor.
Figure 17:
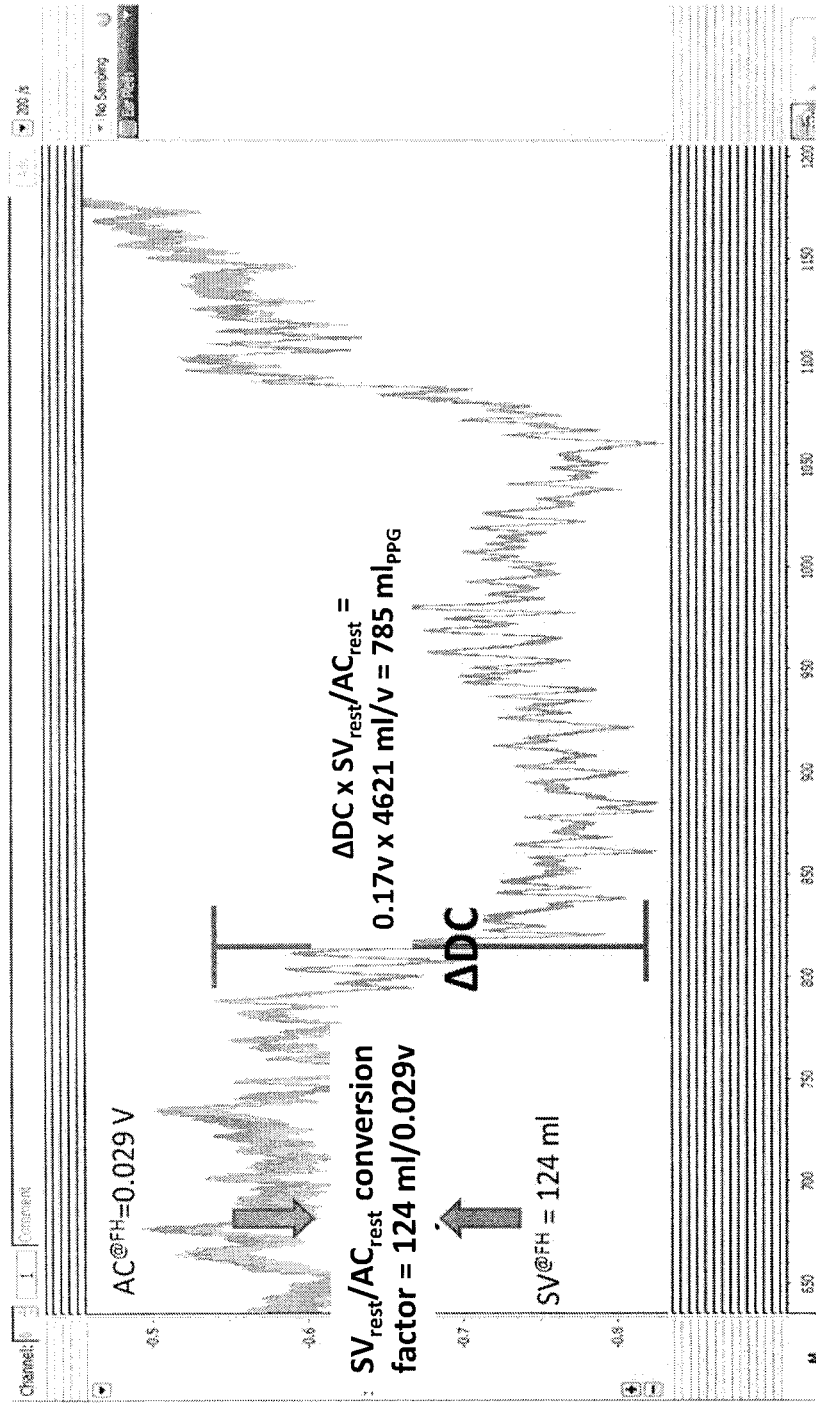
FIG. 17 is a graph of a photoplethysmograph on same subject undergoing lower body negative pressure which illustrates conversion of a decline in voltage to a decline in volume based upon $SV_{rest}$Volume/$AC_{rest}$Voltage conversion factor.

For each photoplethysmograph at a given site in a given subject, the voltage corresponding to the $AC_{rest}$ Voltage was determined and each photoplethysmograph measurement was converted to $AC_{rest}$Mults and AC-derived volumes (in $ml_{ppg}$) as per aforementioned texts and figures. The $AC_{rest}$Mults values for AC and DC for the Ear photoplethysmograph and corresponding volumes were graphed continuously as new channels on the original time axis. (PPG@Finger was collected concurrently for subsequent assessment, discussed below). Examples of graphic display of the Ear photoplethysmographic in a single subject are shown in FIGS. 7-11 (described above). The methodology for conversion to volume is described above, with attention to FIGS. 12 and 13. Measurements during lower body negative pressure are determined per sample table shown in FIG. 15 and graphic displays of voltage to volume conversion for measurement of the amount of simulated blood loss (in $ml_{ppg}$) based upon $AC_{rest}$Mults and the $AC_{rest}$ Voltage conversion factors are shown in FIGS. 16 and 17, respectively. In six of the subjects, $SV_{rest}$ was determined by echocardiography during the baseline phase. In the remaining subjects, the population mean of 125 ml was said to = $SV_{rest}$.

In addition to assessment of the overall photoplethysmographic signal, changes in AC and DCblood can be assessed separately in accordance with present invention. The mean±SD declines in AC $ml_{PPG}$ and DC $ml_{PPG}$ were compared to the LBNP-induced declines in stroke volume and overall systemic volume reported in the literature [Cooke W H, Ryan K L and Convertino V A. Lower body negative pressure as a model to study progression to acute hemorrhagic shock in humans. J Appl Physiol. 2004; 96:1249-61].

The decline in AC between baseline and the onset of light-headedness was determined and compared to baseline in $AC_{rest}$Mults as well as $ml_{ppg}$:

'↓AC in $AC_{rest}$Mults'/'$AC_{pre}$ in $AC_{rest}$Mults'=%↓AC; or

'↓AC converted to $ml_{PPG}$'/'$AC_{pre}$ converted to $ml_{PPG}$'

The relative decline was compared to the relative decline in stroke volume obtained during prior investigations when measurements of stroke volume were obtained (with difficulty) by echocardiography during lower body negative pressure.

The decline in DC (in $AC_{rest}$Mults and converted to $ml_{PPG}$) likewise was determined between baseline and light-headedness. However, determination of relative ↓DC/$DC_{pre}$ required additional steps akin to those described in relation to FIG. 6 to eliminate the impact of background and thereby avoid a spuriously high denominator as a consequence of DCbackground. Based on Series #1 findings in accordance with the method of FIGS. 4 and 6, $DCblood_{pre}$ was assigned a value of 32 $AC_{rest}$Mults (to incorporate the entire systemic circulation). This value was based on the added ~6 $AC_{rest}$Mults decline associated with elimination of the arterial signal as per the method of FIG. 4, which was consistent with adding volumes within aorta (100 ml), arteries (300), arterioles (50) and heart (300), totaling ~750 ml to the 3250 ml cited above within capillaries, venules, veins, vena cavae and right atrium. Per the aforementioned conversion factor, the value of 32 $AC_{rest}$Mults estimated for $DCblood_{rest}$ (which also was $DCblood_{pre}$) was multiplied by the measured (or estimated) $SV_{rest}$Volume to generate baseline DC volume. (Although not elected for the series of subjects so as to avoid disturbance of the sensors, $DCblood_{pre}$ can be measured, as opposed to simply estimated, as for the methods used for and/or described in reference to Series #1 and shown in FIG. 4).

The decline in DC between baseline and the onset of light-headedness was determined and compared to baseline in $AC_{rest}$Mults as well as $ml_{ppg}$:

'↓DC in $AC_{rest}$Mults'/'$DCblood_{pre}$ in $AC_{rest}$Mults'=%↓DC; or

'↓DC converted to $ml_{PPG}$'/'$DCblood_{pre}$ converted to $ml_{PPG}$'

Hence, in addition to estimating overall loss, the data permit comparison of relative venous and arterial decline. The photoplethysmograph based calculations were close to the simulated loss reported in the literature.

As noted in Table 7 below, the $\Delta AC/AC_{pre}$ was ~0.56±0.30 (mean±SD). This 56% decline, which was the same as a decrease of 0.56 $AC_{rest}$Mults, was close to the reported 65% ↓ in measured SV reported in the literature for similar degrees of lower body negative pressure. Conversion to volume indicated a decline in stroke volume of 70.0±37.5 $ml_{PPG}$.

The decline in DC averaged ~7.73±3.65 $AC_{rest}$Mults. The $\Delta DC/DCblood_{pre}$ constituted a 24% reduction from the ~32 $AC_{rest}$Mults corresponding to nonpulsatile systemic blood prior to lower body negative pressure. The mean decline in DC was 14× greater than the decline in AC (=7.73/0.56). Conversion to volume indicated a decline in systemic volume of 966.3±456.39 $ml_{ppg}$. This is within the 500 to 1500 ml range of simulated loss reported in the literature for comparable degrees of lower body negative pressure. As discussed with respect to subjects during the recovery phase, intersubject variability may be attributable to different physiologic responses to the challenge.

TABLE 7

Declines in AC and DC and related volume conversions during lower body negative pressure

| Subjects | ΔBaseline | ΔAC | ΔAC/pre AC | ΔBaseline/ Pre AC | ΔBaseline/ ΔAC | Estimated Blood Withdrawal | Pre Stroke Volume |
|---|---|---|---|---|---|---|---|
| 1 | −0.181 | −0.022 | −0.758 | −6.334 | 8.359 | −791.740 | 124.0 |
| 2 | −0.440 | −0.020 | −0.541 | −11.938 | 22.050 | −1492.254 | |
| 3 | −0.185 | −0.033 | −0.736 | −4.150 | 5.638 | −518.700 | |
| 4 | −0.054 | −0.005 | −0.581 | −6.183 | 10.651 | −772.898 | 109.0 |
| 5 | −0.488 | −0.034 | −0.957 | −13.876 | 14.496 | −1734.519 | 103.0 |
| 6 | −0.154 | −0.003 | −0.113 | −5.917 | 52.431 | −739.682 | 164.0 |
| 7 | −0.031 | −0.001 | −0.236 | −5.716 | 24.222 | −714.532 | 126.0 |

TABLE 7-continued

Declines in AC and DC and related volume conversions during lower body negative pressure

| Subjects | ΔBaseline | ΔAC | ΔAC/pre AC | ΔBaseline/ Pre AC | ΔBaseline/ ΔAC | Estimated Blood Withdrawal | Pre Stroke Volume |
|---|---|---|---|---|---|---|---|
| MEAN | −0.219 | −0.017 | −0.560 | −7.73 | 19.69 | −966.332 | 125.2 |
| STD | 0.18 | 0.01 | 0.30 | 3.65 | 15.98 | 456.39 | 23.78 |

Comment: $SV_{rest}$ for subjects 2 and 3 estimated to be the mean value of 125 ml.

Figure 18:
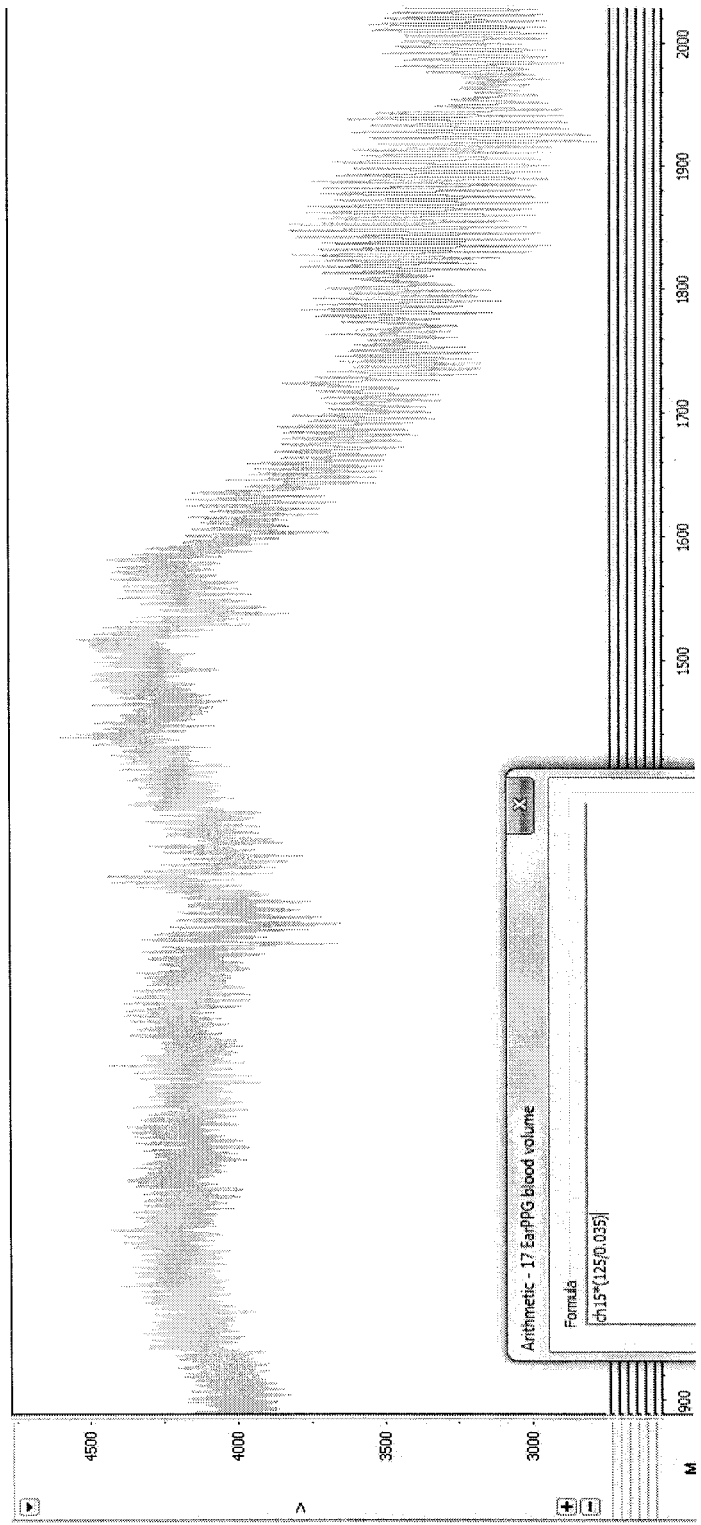
FIG. 18 shows graph of volume (in $ml_{PPG}$) generated by an ear photoplethysmograph during lower body negative pressure based upon converting voltage to $ml_{ppg}$ using inventive voltage to volume conversion factor and/or $AC_{rest}$Mult to volume conversion factor.
Figure 19:
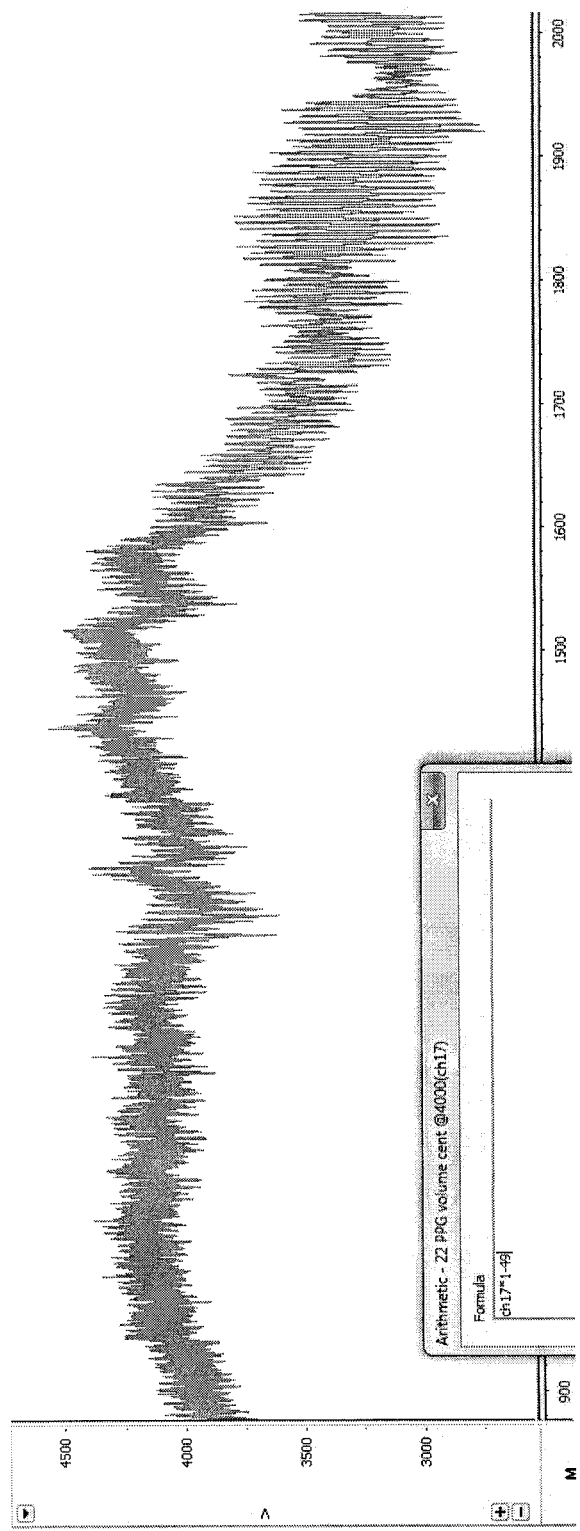
FIG. 19 shows that, if one wishes to standardize crossing point of y-axis for preLBNP volume (i.e., volume @rest) to 4000 $ml_{ppg}$ (based upon data shown herein) for the subject shown in FIG. 8, the offset for the present subject would be −49 $ml_{PPG}$.
Figure 20:
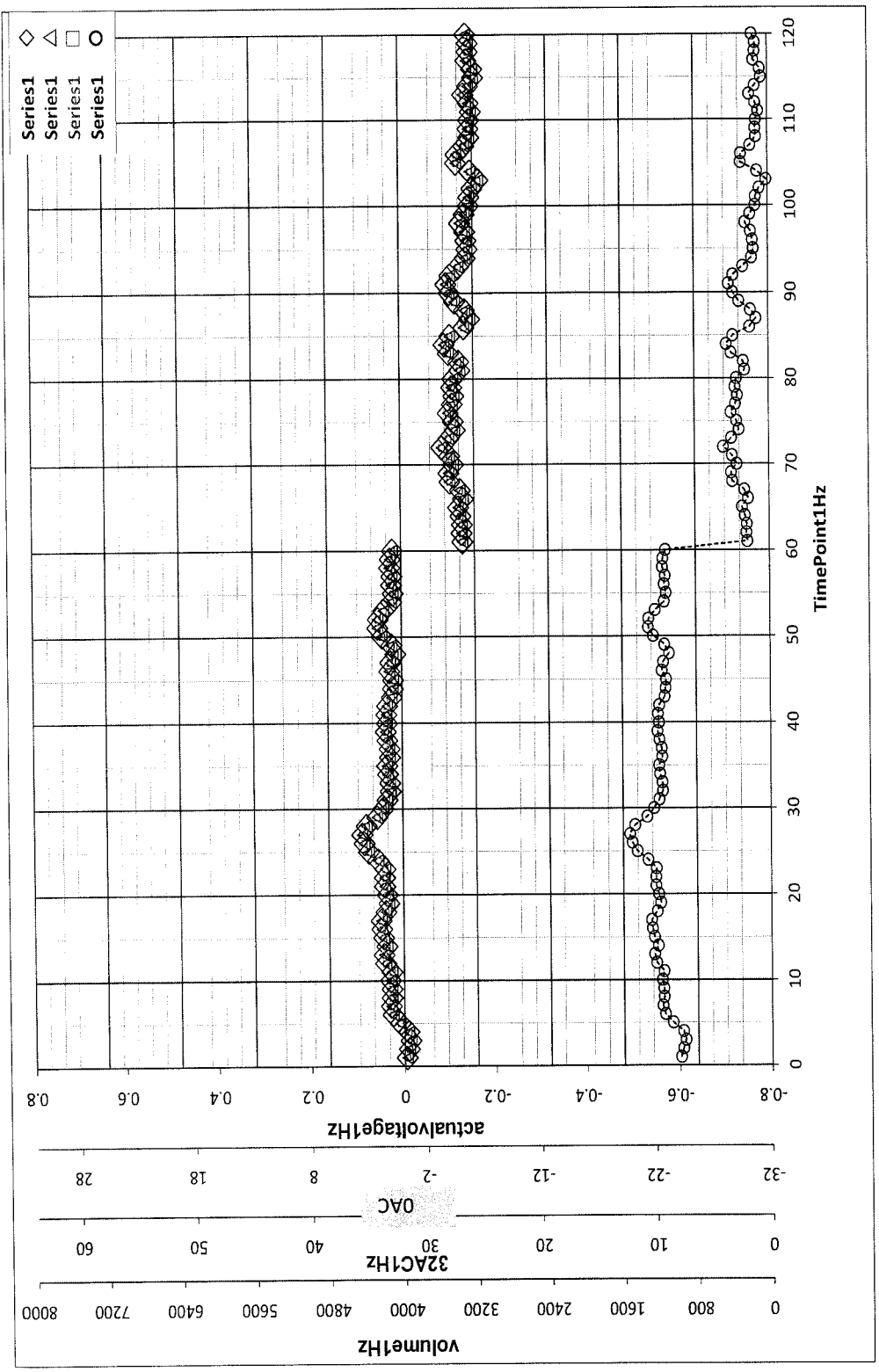
FIG. 20 shows multiple tracings graphed on multidimensional vertical axis.
Figure 21:
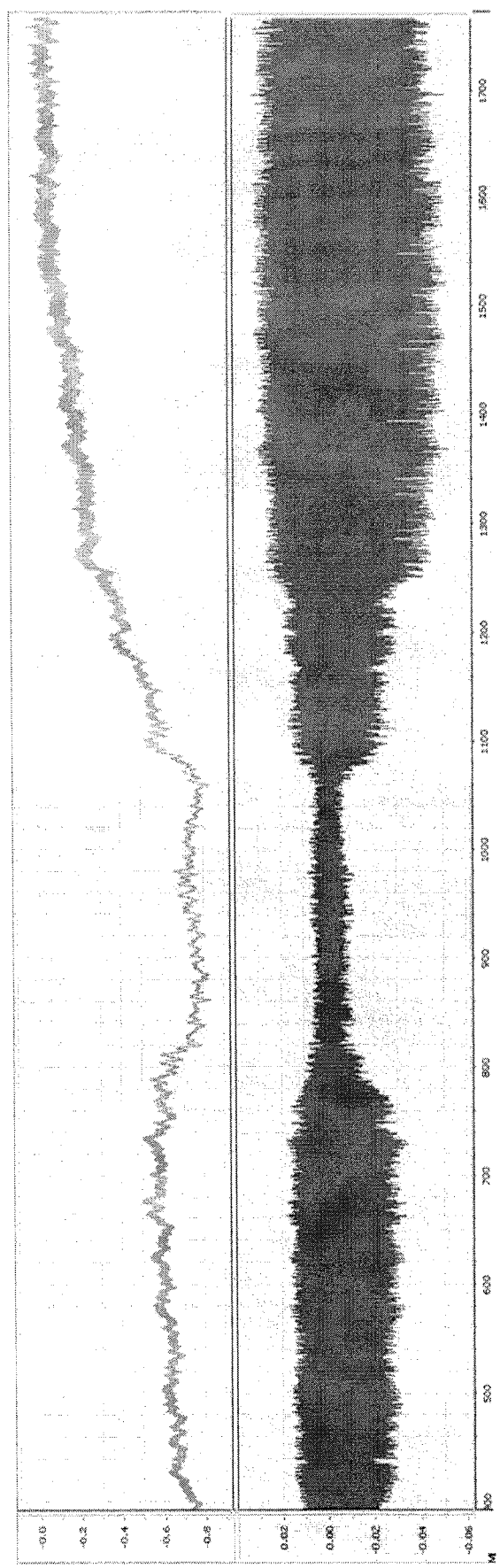
FIG. 21 shows the plethysmographic tracing at the Ear of a subject during baseline, application of negative pressure and recovery during a lower body negative pressure protocol.

FIGS. 18 and 19 show the changes in volume in a single subject. FIG. 20 integrates means of data display for a single subject on a single graph.

Recovery from Lower Body Negative Pressure:

The ability to distinguish AC and DC was during recovery upon release of lower body negative pressure would be vital to the management of patients with hypovolemia. These patients commonly first receive medical attention after significant blood loss already has occurred (e.g., trauma) and it is difficult to assess current status with respect to volume, vascular tone and cardiac function. This has prompted reliance on response studies, wherein the response to fluid administration is assessed (albeit with difficulty because of current inadequacies of monitoring). Restoration of systemic volume by release of lower body negative pressure (akin to volume infusion) provided a means to assess the utility of embodiments of the current invention.

During the recovery phase, the release segment (from lower body negative pressure off to maximum plethysmographic reading) was divided into 4-8 successive phases (based on duration of recovery and available window of suitable data). The AC and DC of each phase were determined by averaging 10-12 beats. Then ΔAC and ΔDC from baseline were calculated for each phase.

$$\Delta AC = (AC_{@GivenTimePoints} - AC_{rest})$$

$$\Delta DC = (DC_{@GivenTimePoints} - DC_{rest})$$

The values were expressed in $AC_{rest}$Mults and converted to $ml_{PPG}$ in accordance with aforementioned descriptions.

Figure 22:
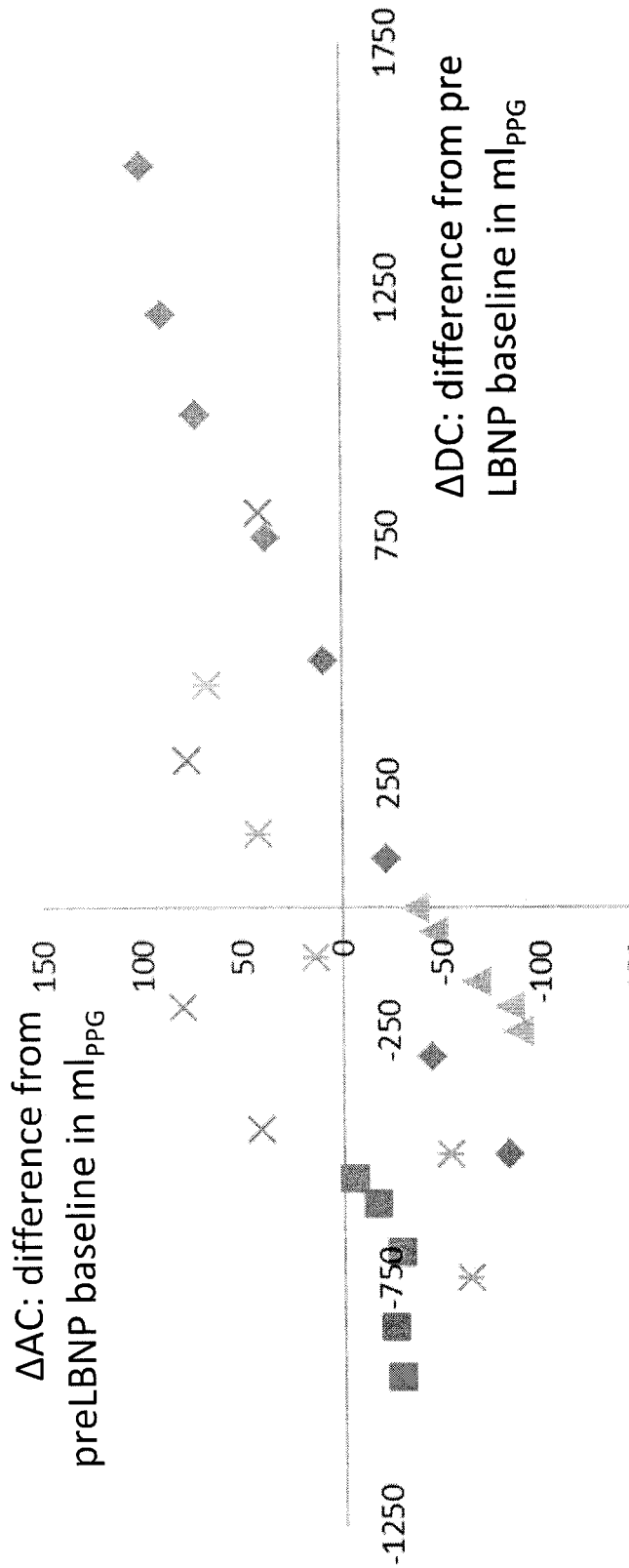
FIG. 22 shows the responses of AC and DC to release of negative pressure of FIG. 21 in five subjects.

FIGS. 22-27 show the application of, and potential utility of, independent and comparative assessment of AC and DC in $AC_{rest}$Mults and $ml_{ppg}$ in accordance with the present invention. In each of the five subjects for which segments of recovery are shown in FIG. 22, DC and AC increased upon progressive release of negative pressure. At the onset and early stages of recovery, all subjects were in the left lower quadrant, indicating that both DC (horizontal axis) and AC (vertical axis) were below preLBNP baseline values (consistent with hypovolemia). The rate and magnitude of recovery varied among subjects and between signal components. Intersubject variability was attributable to different degrees of negative pressure, different times of onset and different rates of release of negative pressure. Differences between AC and DC responses commonly revealed the bases for changes detected by other monitors and/or clinical signs; i.e., in addition to the hypovolemia of lower body negative pressure, the pattern of AC and DC responses may help distinguish cardiac factors (decreased cardiac function) and peripheral factors (altered vasomotor tone, local injury). Overshoot of restored volume return could be due to a number of factors, which would be identified by the relationship between AC and DC (e.g., hyperdynamic heart, local reflex hyperemia, injury induced hyperperfusion, hypervolemia). Patterns may be characterized by quadrant location (FIG. 22): upper right quadrant suggests that combination of fluid return and homeostatic mobilization from stores to mitigate the hypovolemic phase led to hypervolemia and augmented stroke volume (Rx, if any, might be a diuretic or vasodilator); upper left quadrant suggests increased contractility such that SV is greater than baseline even if systemic volume has not returned to normal (Rx may include judicious volume replacement, alteration of vasomotor tone or, if heart is undesirably hyperdynamic, use of an agent such as a beta-adrenergic blocker); lower right quadrant suggests compromise of cardiac contractility and/or intense arterial constriction such that AC is reduced despite replenishment of systemic volume (Rx may include increasing cardiac contractility).

Figure 23:
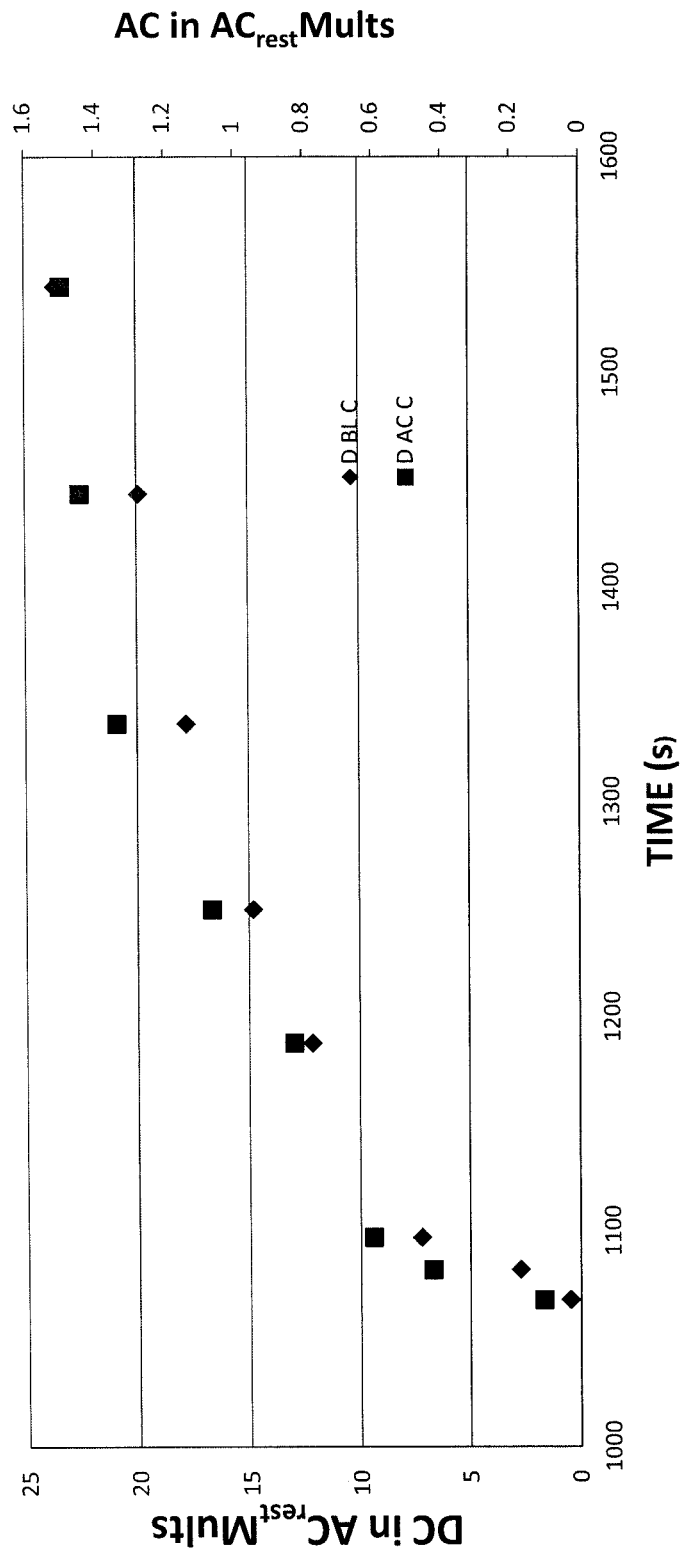
FIG. 23 shows the responses of AC and DC of a single subject in $AC_{rest}$Mults.
Figure 24:
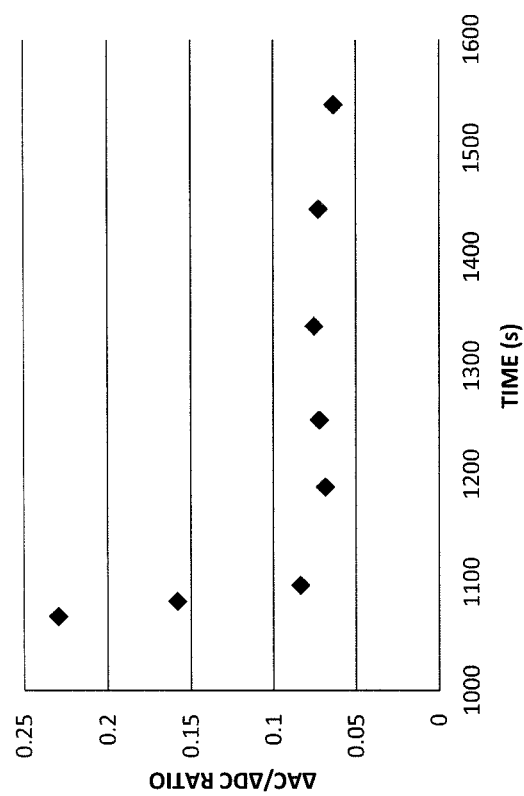
FIG. 24 shows ratio of ΔAC/ΔDC for data in FIG. 23.
Figure 25:
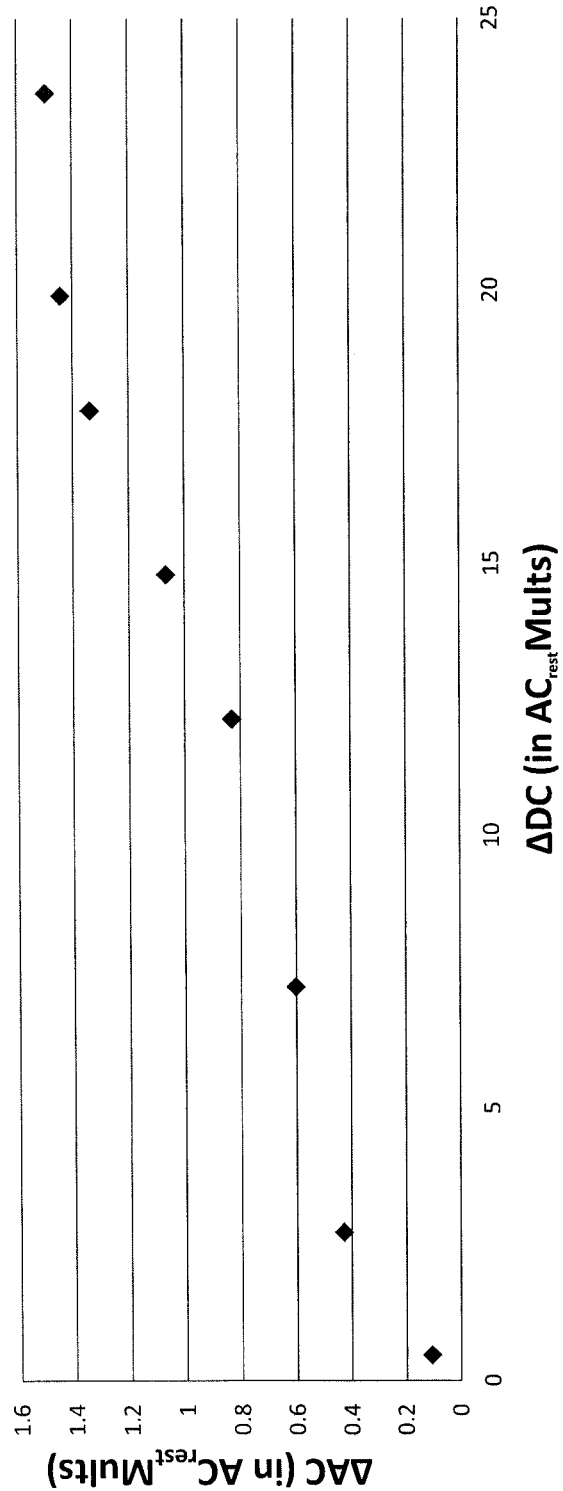
FIG. 25 shows how we can display relationship of AC and DC in a manner comparable to the Frank-Starling relationship for stroke volume and end diastolic volume.

The relationships between AC and DC (in $AC_{rest}$Mults) are shown for a single subject in FIGS. 23-25. Values represent increase from LBNP-induced nadir, which is assigned a value of 0. In FIG. 23, it is seen that the relative rate of rise in AC compared to DC is greatest upon initial return of sequestrated volume, indicating that the body is preferentially restoring stroke volume. The difference led to a return of AC to greater than baseline (as which time, $AC_{rest}$ was, by definition, 1 $AC_{rest}$Mult). FIG. 24 further depicts the changing relationship between AC and DC during recovery, with the initial ΔAC/ΔDC ratio of 0.23 reducing to 0.06 at the end of restoration. Of potentially greatest clinical significance, FIG. 25 shows a Frank-Starling relationship: during recovery, the subject is on the steep part of the curve with exaggerated ΔAC/ΔDC, consistent with the steep part of the Frank Starling curve where there is a robust response of SV for a given change in venous volume (evidenced as end diastolic volume in the classic Frank Starling curve).

Figure 26:
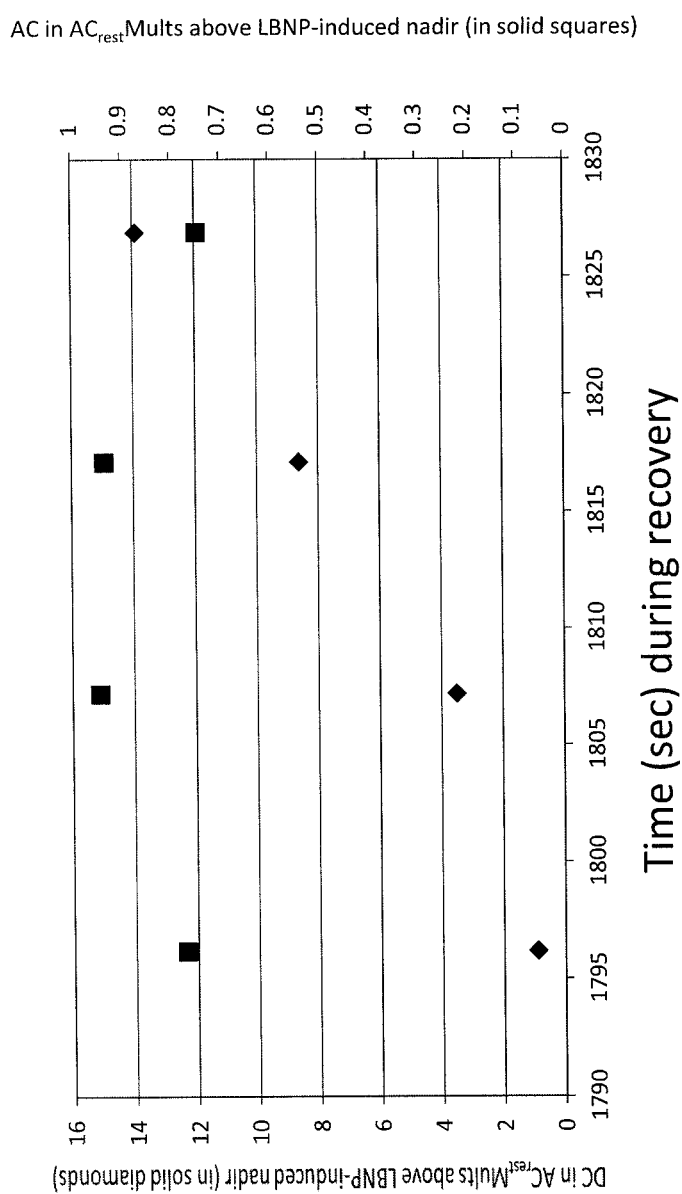
FIG. 26 shows AC and DC responses of a subject who developed light-headedness during return of blood sequestered in legs during lower body negative pressure.

In addition, the findings confirm that application of embodiments disclosed herein can provide valuable information as to the mechanisms associated with clinical signs and symptoms. FIG. 26 shows the recovery phase of a subject who became light-headed beginning at 1822 seconds. While overall systemic volume (DC, in diamonds) continued to increase, SV as measured by AC (solid squares) suddenly dropped.

Figure 27:
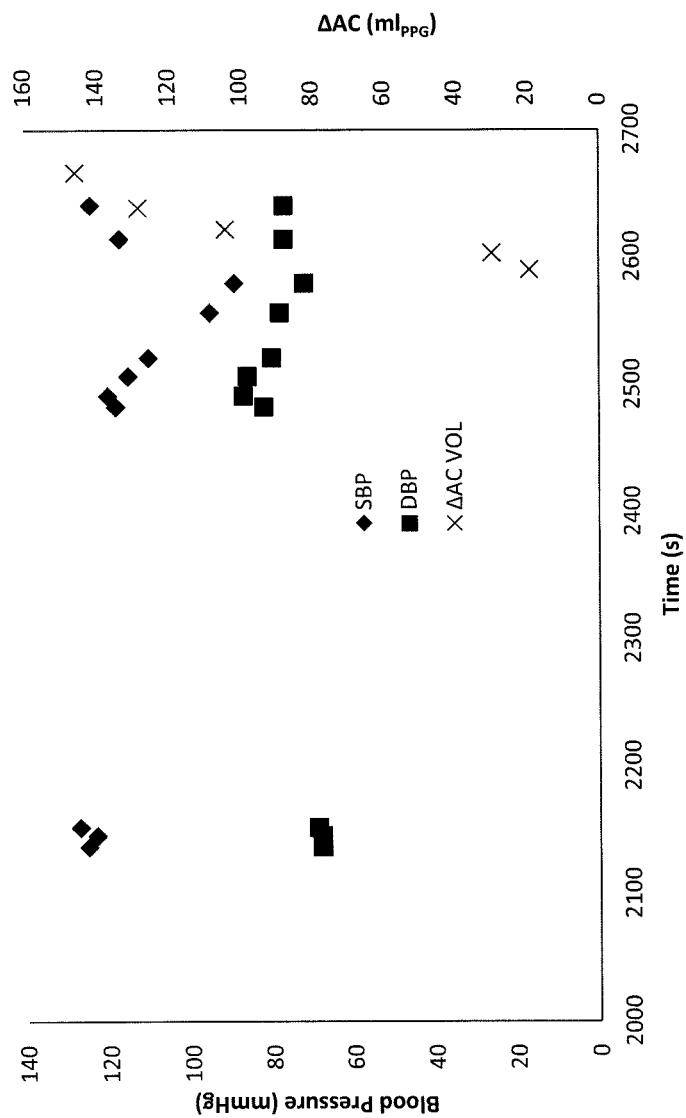
FIG. 27 shows AC changes in a subject who became hypotensive during return of blood sequestered in legs during lower body negative pressure.

FIG. 27 shows a subject in whom reinfusion was initiated at approximately 2450 seconds. After an initial rise in blood pressure, the systolic blood pressure declined from 120 mmHg to 82 mmHg. This was associated with a lack of increase in AC despite return of sequestrated blood (increase of DC). The relationship between AC and DC in this subject is also shown as the series of five star-like data points beginning at −60 ΔAC and −750 ΔDC in FIG. 22. Note that the increase in DC from −750 $ml_{PPG}$ to −500 $ml_{PPG}$ was associated with negligible increase in AC $ml_{PPG}$.

Finger Vs Ear Plethysmographic Changes During Lower Body Negative Pressure:

Application of the characterization of the AC and DC components of the plethysmographic signal in accordance with the present invention to multiple sites in a given subject (e.g., patient) offers the potential to multiply the benefits of inventive designs and methods. This is exemplified by data obtained concurrently at Ear and Finger during the aforementioned lower body negative pressure model, as summarized in FIG. 28. This shows the section of an Excel (Microsoft) spread sheet which contains data from 11 subjects who had concurrent Ear and Finger monitoring during our lower body negative pressure trial. The greater relative decline in the AC component (i.e., delivered stroke volume) of the Finger vs Ear is evidenced (in columns U and V) by their respective declines in AC height of 0.559 and 0.441 $AC_{rest}$Mults (where $AC_{rest}$ Voltage is specific for given site); the decline at the Finger averaged 1.47× that at the Ear (col W). The greater relative decline in Finger vs Ear venous volume is evidenced by their respective declines of 8.02 and 2.46 $AC_{rest}$Mults (columns Y and Z); decline at the Finger averaged 3.95 times that at the Ear. These values may allow establishment of cutoffs for degrees of arterial constriction and venous constriction indicative of activation of homeostatic reflexes by severe hypovolemia. For example 10 of the 11 subjects had ↓DC @Finger that was at least 1.4 times greater than ↓DC@Ear, providing 1.4 as a tentative cutoff for identifying hypovolemia in an individual capable of a homeostatic response. While intersubject differences may provide valuable insight in patient characteristics (e.g., as per altered plethysmographic responses during reinfusion (FIGS. 26 and 27), confounding variability may be reduced with available artifact rejection algorithms and use of reference signals (not responsive to blood movement) that can improve the consistency of probe orientation at a given site.

Hence, the application of inventive embodiments at multiple sites enables comparisons with respect to the arterial and venous components of the circulation at the these sites in a previously unattainable manner in the clinical setting. The findings tell a story: as expected, the greater amount of arterial constriction at the finger causes a greater decline in its AC height; moreover, the greater decline in the DC component illustrates venous constriction at the finger, an indication of fluid mobilization from peripheral sites to offset the systemic hypovolemia induced by blood sequestration in the lower extremities during lower body negative pressure. It is reasonable to assume that the different changes at these sites reflect changes in regions with comparable innervation that are not accessible to noninvasive photoplethysmographic monitoring (e.g., brain, splanchnic vasculature and kidney).

The data also permit additional analyses, including:
a) comparisons of the $\Delta AC/AC_{pre}$ ratios at the Ear and Finger—measuring the differences between Ear and Finger so as to enable determination of the fractions of the Finger decline that is attributable to systemic volume loss (that impacts Ear and Finger) or regional vasoconstriction (that predominantly impacts Finger), e.g., $\Delta$@Finger-$\Delta$@Ear and/or $\Delta$/pre ratio at Finger-$\Delta$/pre ratio at Ear
b) comparison of the relative ↓DC at the different sites so as to assess the relative amount of homeostatic fluid mobilization (as would be coming not only from extremities such as the Finger but also internal regions such as the splanchnic vasculature and spleen). The greater decline in DCblood in the Finger of the present series reveals mobilization that is consistent with the observation in the "responder" study above that return of the sequestrated fluid (in addition to the mobilized fluid) led to overshoot at the end of the restoration period.

As per the embodiments shown in FIGS. 4 and 6 and accompanying text, one also can normalize to the $DCblood_{pre}$ at the respective sites to obtain relative declines in DC as well as AC and to calculate changes in compliance.

Thus concurrent utilization of the AC and DC components in accordance with the present invention allows distinction, delineation and comparison of changes in the peripheral arterial and venous vasculature (vascular tone as well as volume). Resultant appreciation as to the impacts of hypovolemia per se and resultant changes in arterial and vasoconstriction can the guide therapy. For example, the greater decrease in DC@Finger reveals compensatory venous vasoconstriction that not only indicates the need for volume infusion but also can alert a health care provider that rapid replacement of all volume lost can lead to overshoot. Additionally, a disproportionate decrease in finger height reveals arterial constriction, indicating that the patient's blood pressure is being maintained by compensatory increase in vascular tone, which may be harmful to an organ such as the kidney. In the present series, application of embodiments introduced herein reveals that during lower body negative pressure most subjects evidenced decreased systemic volume, decrease stroke volume, venous constriction and arterial constriction. In more routine clinical settings, a patient's responses may be similarly assessed in the context of challenges such as the less extreme blood pooling associated with changing from a supine to upright posture as well as in the context of vasoactive medications as may be titrated to treat chronic hypertension. As per FIGS. 26 and 27, abnormal responses may be most revealing.

In addition, as noted above, @rest values may be obtained at the onset of a challenge such as lower body negative pressure or days, weeks, months . . . before one is at risk of trauma or alternative compromise or intervention. As evidenced by the consistency of AC (described above), photoplethysmographic values remain consistent for a given sensor at a given site under resting conditions. Hence, @rest values for AC (as well as DC which maintained similar consistency) of one or more sensors on one or more subjects can be stored for a given probe and given station (for emission and processing) or for a group of uniform probes and stations.

Additional Applications of Meaningful Measurements:

A major benefit of the present invention is its conversion of often meaningless voltages to meaningful measures, these including $AC_{rest}$Mults, $AC_{rest}$Mult/mmHg compliance, and $ml_{PPG}$ measures of stroke volume and overall systemic volume.

This is particularly evident when one subjects data to what has been referred to as "black box" analysis because the analysis is performed by algorithms either hidden from or beyond the appreciation of most clinicians (and investigator). Spectral domain analysis is one such technique: it determines the contribution of a series of frequencies to the variance of a signal, traditionally by Fourier transformation; i.e., it determines the degrees to which oscillations at each of the frequencies within the given range contributes to overall signal variance. This technique has been recommended by my research team [Shelley K H, Shelley A, Silverman D G, Stout R G: Method of assessing blood volume using photoelectric plethysmography (U.S. Pat. No. 8,251,912; issued August 2012] and others for assessing the degree of variation in the photoplethysmographic signal attributable to respiration (typically between 0.1 and 0.3 Hz). However, that patent relied on relative changes, e.g., comparison of changes in DC at the respiratory frequency to oscillations of the AC components at the heart rate frequency (approximately 1 Hz) to provide a meaningful assessment. (Note, that prior to the present invention, relative measures of oscillatory-induced changes, not actual AC and DC values, were applied to patient assessment)

Figure 29:
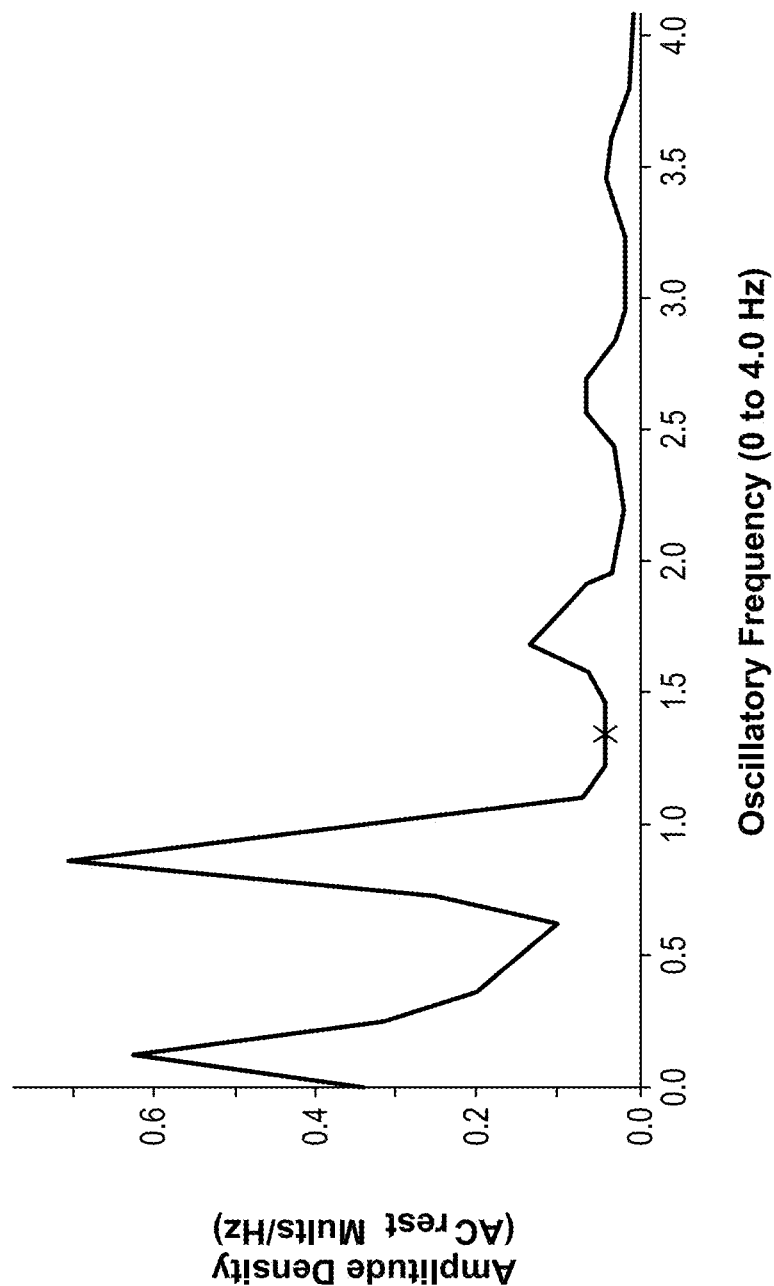
FIG. 29 shows the application of $AC_{rest}$Mults to provide heretofore unattainable clarity with respect to the delineation of data generated by spectral-domain analysis.
Figure 30:
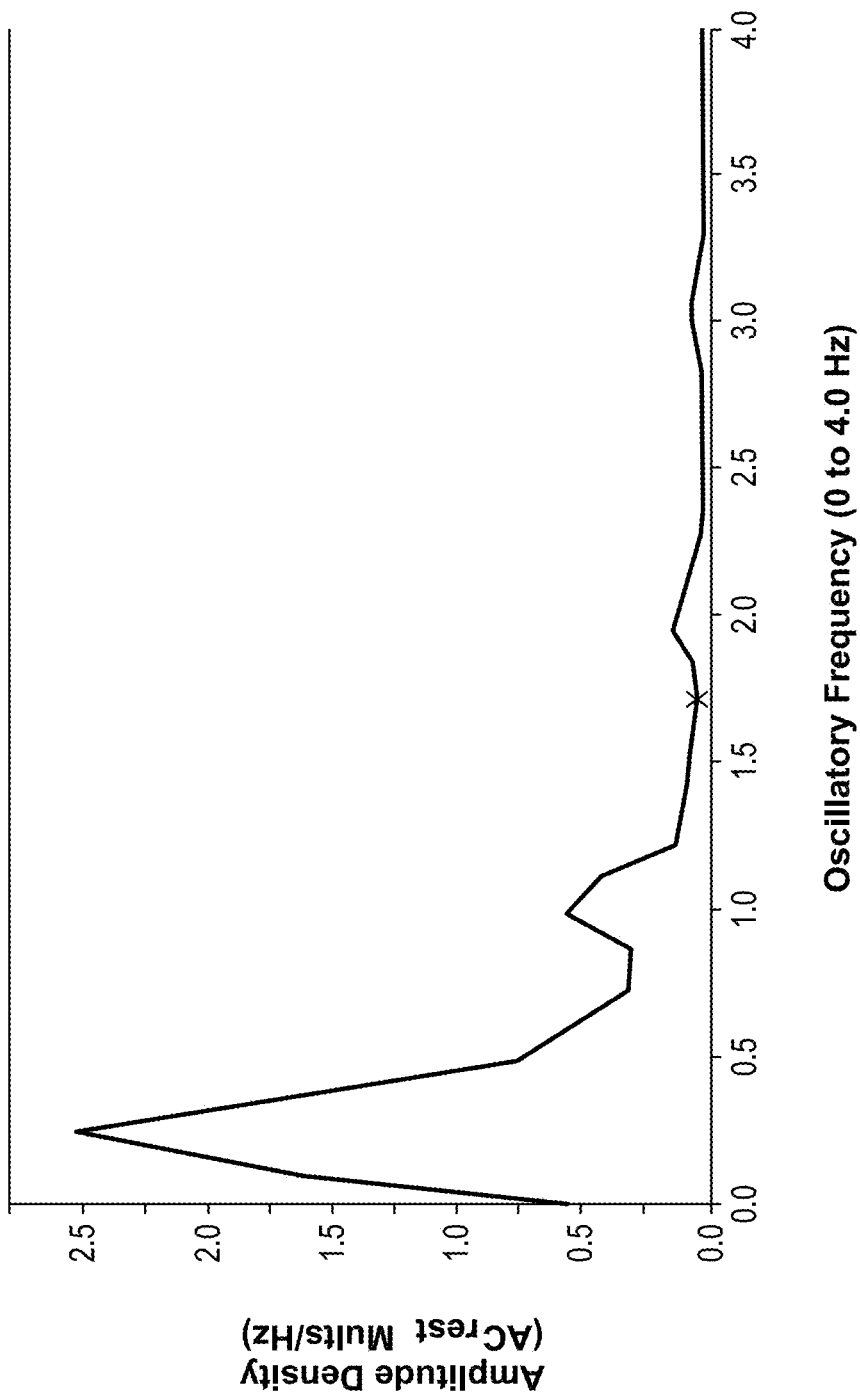
FIG. 30 shows the application of FIG. 29 to a subject breathing against a resistance so as to increase the impact of respiration on the distribution of venous blood volume.

FIGS. 29 and 30 show how conversion to $AC_{rest}$Mults provides heretofore unattainable meaning to spectral domain analysis of the plethysmographic waveform. Within the range of cardiac frequencies that are sampled at a given spectral resolution, it tells in readily appreciable units whether the stroke volume is <, =, or > than it was under resting conditions. In FIG. 29, we see that at the three frequency bands encompassing heart rate (at the given window width, sampling rate and FFT size), the heart rate oscillations (within the range of the subject's heart rate during the sampling period) have an amplitude density of 0.95 $AC_{rest}$Mults (0.10+0.70+0.075+0.075), wherein amplitude density integrates the frequencies within the frequency band in the immediate neighborhood of the given frequency. This indicates that the mean amplitude of the stroke volume (0.95 $SV_{rest}$Mults) is 95% of that obtained during @rest calibration. In addition, the data provide a measure of the volume displaced with respiration over the range of respiratory frequencies, that being ~1.17 $AC_{rest}$Mults (~0.35+0.62+0.2). This indicates that the change in central venous blood volume with each breath during spontaneous ventilation in this resting subject averaged 1.17 $AC_{rest}$Mults or 117% of the resting stroke volume.

The embodiments of the present invention facilitate comparison with data generated during breathing against a resistance so as to simulate positive pressure ventilation (as with a ventilator in an intubated patient). FIG. 30 shows that the increased pressure generated within the chest by breathing against a resistance displaced a much larger volume of blood from the chest to the periphery: ~2.9 $AC_{rest}$Mults (~0.6+1.5+0.8). This amount to 290% of $SV_{rest}$. Estimating $SV_{rest}$=125 ml, this amounts to displacement of ~360 ml, consistent with changes obtained with invasive monitoring during mechanical ventilation. FIG. 30 also shows that stroke volume increased with the increased activity of the subject, averaging ~1.4 $AC_{rest}$Mults (~0.5+0.6+0.3).

Figure 31:
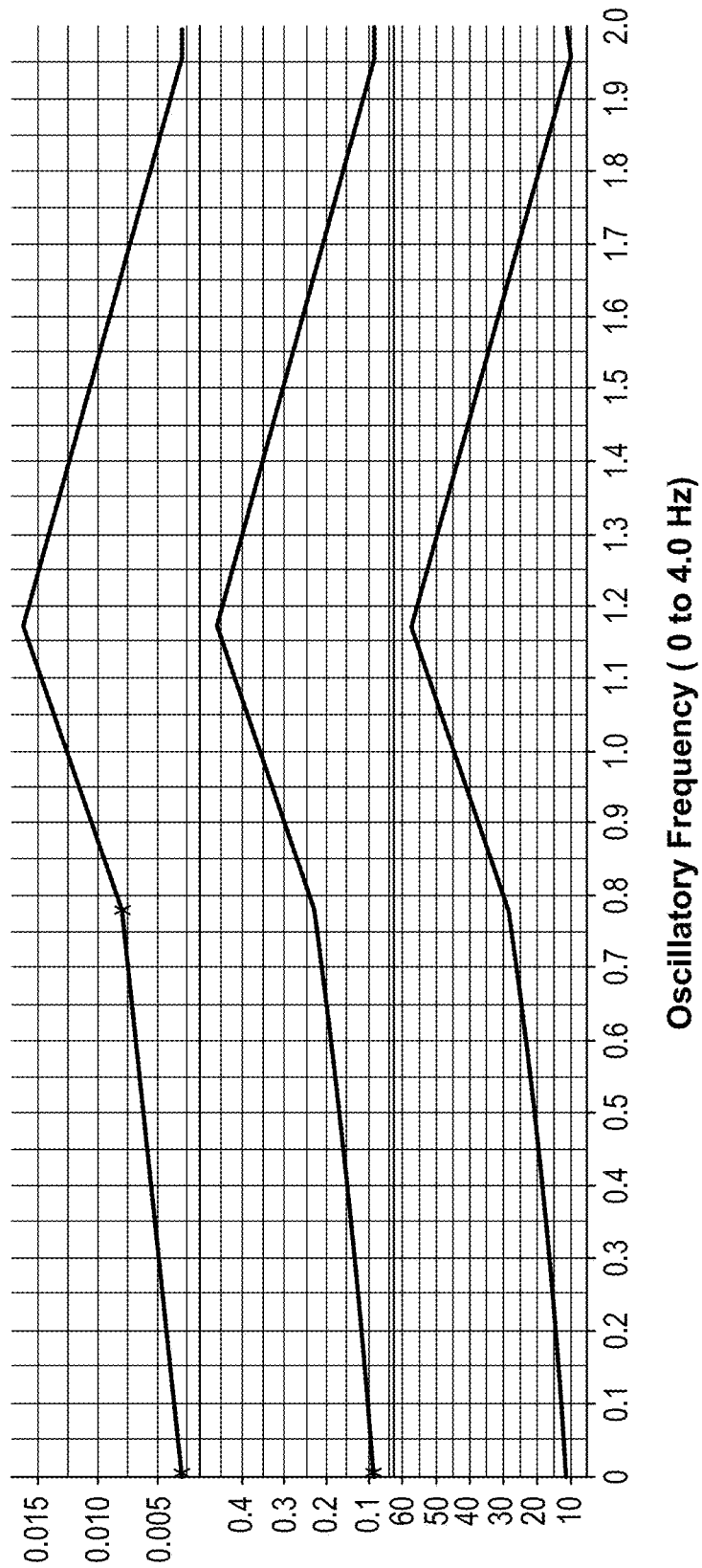
FIG. 31 is based on low frequency resolution of the spectral domain analysis display so as to illustrate the accuracy of $AC_{rest}$Mults and $ml_{ppg}$ determinations.

FIG. 31 is from a different subject a few minutes after initial titration of negative pressure at the start of lower body negative pressure. Here, the frequency resolution has been reduced so that amplitudes of the spectral domain tracing can be readily summated around the cardiac frequency of a signal that has undergoing high pass filtering (>0.5 Hz) so as to eliminate respiratory induced changes in the DC component and thereby enable isolated viewing of AC. The findings confirm the accuracy of $AC_{rest}$Mults and data converted to $ml_{PPG}$ for assessment of stroke volume. The upper channel is the typical display based upon raw voltage. The middle channel shows that the AC component was equivalent to ~0.91 $AC_{rest}$Mults (~0.24+0.46+0.25). Likewise, the bottom channel shows that stroke volume was approximately 116 $ml_{ppg}$ (28+58+30).

Although not shown here, one could determine the impact of heart rate (Rwave to Rwave intervals) on the stroke volume; dividing the amplitude density at each of the three data points by the number of beats contributing to the given value would enable determination of rate-induced differences in volume (as may result from different durations for ventricular filling, which may be of particular importance during hypovolemia). This is just of many applications that will soon become obvious to investigators and clinicians now that the vital tool(s) has been provided.

Inventive Embodiments Exemplified in Subject Undergoing Postural Changes (e.g., Leg Raise):

The aforementioned findings prompted preliminary assessment of herein proposed quantification of DC in the context of simulated volume administration, without the confounding variables posed by reinfusion after lower body negative pressure. Specifically, applicant documents a change in "active" volume in the central circulation and hence identifiable with embodiments to measure DC introduced herein (as opposed to lack of volume or sequestration of "inactive" volume in storage sites such as the spleen). Applicant reports the findings in a 67 year old volunteer (the inventor) in detail (displayed in FIGS. 32-51 and summarized in Tables 8-11), so as to clearly introduce definitions and formulae for assessment of the DC component of the PPG (including intuitive universal $AC_{rest}$Mult and $ml_{ppg}$ units).

In accordance with these findings, and as will be appreciated based upon the following detailed discussion, the present invention provides a microprocessor implemented method for photoplethysmograph measurement of volume status and changes. The methodology includes filtering oscillations at >0.5 Hz from a photoplethysmographic signal to isolate the DC component thereof. Thereafter, the DC component is measured, and changes resulting from changes in cardiac ejection of pulse as indicated by stroke volume, cardiac output, blood pressure or pulsatile component of a peripheral monitor are measured. The changes in the DC component are compared to changes resulting from changes in cardiac ejection of pulse as indicated by stroke volume, cardiac output, blood pressure or pulsatile component of a peripheral monitor to provide a ratio. The ratio is applied to noninvasively provide a measure of relative values (changes) in preload to and blood ejection by the heart. Further, the systemic cardiovascular status is monitored based upon the measure of relative values (changes) in preload to and blood ejection by the heart to identify and monitor conditions of altered volume status and guide treatment.

In accordance with this methodology, the DC component is measured in $AC_{Test}$Mults or $ml_{PPG}$. Still further, in multiple embodiments the DC component is normalized to a baseline value of the DC component, and the baseline value is determined for a given site or is estimated based upon predetermined population values.

In accordance with an alternate embodiment, the methodology includes filtering oscillations at >0.5 Hz from a photoplethysmographic signal to isolate the DC component thereof. Thereafter, the DC component is measured, and changes resulting from changes in cardiac ejection of pulse as indicated by stroke volume, cardiac output, blood pressure or pulsatile component of a peripheral monitor are measured. The oscillatory changes in the DC component are compared to changes in cardiac ejection of pulse as indicated by stroke volume, cardiac output, blood pressure or pulsatile component of a peripheral monitor to provide a ratio that noninvasively provides a measure of oscillatory changes in preload to changes in blood ejection by the heart. The systemic cardiovascular status is measured based upon the measure of oscillatory changes in preload to changes in blood ejection by the heart to identify and monitor hypovolemic conditions.

In accordance with this methodology, the oscillatory changes in the DC component are largely due to respiration. The oscillatory changes in the DC component are quantified in the time-domain and/or the spectral domain. Frequency bands within the DC component of a photoplethysmographic signal are isolated to selectively assess impact of respiration, assess impact of sympathetic activity, and/or assess impact of parasympathetic activity. This methodology may also include the step of quantifying the change in blood ejection by the heart with a measure of respiration-induced variation, wherein the measure of respiration-induced variation may be expressed as changes in the perfusion index (PI) (also referred to as the pulsatile index) or the pleth variability index.

In accordance with yet another embodiment, the methodology of the present invention includes measuring a DC component of a photoplethysmographic signal and an AC component of photoplethysmographic signal, and thereafter determining a baseline, estimated baseline or a preintervention value of the DC component and determining a baseline, estimated baseline or a preintervention value of the AC component. A difference in the DC component from the baseline, estimated baseline or preintervention value is compared to a difference in the AC component from the baseline, estimated baseline or its preintervention value. In accordance with this methodology, the measurements may be taken at multiple sites, and a difference in the AC component in association with the difference in DC component is compared to change at a different monitoring site. A change in the difference in the AC component in association with the difference in DC component is compared to change of measure of cardiac pulsatile ejection, wherein a relative decline in the AC component at a given site is an indication of local volumetric autoregulation.

In accordance with a further embodiment, the methodology of the present invention includes filtering oscillations at >0.5 Hz from a photoplethysmographic signal to isolate a DC component from the photoplethysmographic signal and filtering oscillations at <0.5 Hz from a photoplethysmographic signal to isolate a AC component from the photoplethysmographic signal. The DC component of the photoplethysmographic signal and the AC component of the photoplethysmographic signal are then measured. A baseline, estimated baseline or a preintervention value of the DC component is determined and a baseline, estimated baseline or a preintervention value of the AC component is determined. A change in respiration-induced variation of the DC component from the baseline, estimated baseline or preintervention value is determined and the change in respiration-induced variation of the DC component is compared to change in the AC component from the baseline, estimated baseline or preintervention value.

In accordance with embodiments of this methodology, the measurements are taken at multiple sites, and a difference in the AC component in association with the difference in DC component is compared to change at a different monitoring site. A change in the difference in the AC component in association with the difference in DC component is compared to change of measure of cardiac pulsatile ejection, wherein a relative decline in the AC component at a given site is an indication of local volumetric autoregulation. A change in the difference in the AC component is a change in ACpeak, ACtrough, ACheight, or ACmean, and a change in the difference in the AC component is a change in respiration-induced variation of an AC signal.

TABLE 8

|  | FLAT | HEAD UP | LEGS UP | H/U TILT | H/D TILT |
|---|---|---|---|---|---|
| SV | 130 | 70 | 160 | 80 | 150 |
| HR | 56 | 57 | 55 | 59 | 54 |
| BPsys | 118 | 105 | 122 | 115 | 128 |
| BPdias | 88 | 80 | 84 | 82 | 90 |

TABLE 9

|   |   | Flat | | LegRaise | | LegRaise-Flat | | |
|---|---|---|---|---|---|---|---|---|
| A | Time-Domain assessment during breath of PPG$^{Forehead}$ in AC$_{rest}$Mults and concurrent filtering oscillations at >0.5 Hz for isolation of the DC component and filtering oscillations at >0.5 Hz for given breath and for same beat (channels 1-3 measured on tracings); FIGS. 36-39. OVER COURSE OF BREATH | | | | | | |
|   |   | AC$_{rest}$Mults | ml$_{PPG}$ | AC$_{rest}$Mults | ml$_{PPG}$ | AC$_{rest}$Mults | ml$_{PPG}$ | % Change |
| 1 | maxACpeak | 154.25 |  | 157.9 |  | 3.65 |  |  |
| 2 | minACpeak | 153.9 |  | 157.5 |  | 3.6 |  |  |
| 3 | Max − minACpeak | 0.35 | 38.5 | 0.4 | 44.0 | .05 | 5.5 |  |
| 4 | maxACtrough | 153.25 |  | 156.75 |  | 3.5 |  |  |
| 5 | minACtrough | 153.1 |  | 156.6 |  | 3.5 |  |  |
| 6 | max − minACtrough | 0.15 |  | 0.15 |  | 0 |  |  |
| 7 | Diff max peak − min trough within resp | 1.15 |  | 1.32 |  | 0.17 |  | 14.78% |
| 11 | DC@max during breath | 153.92 |  | 157.4 |  | 3.48 | 382.8 |  |
| 12 | DC@min during breath | 153.62 |  | 157.0 |  | 3.38 | 371.8 |  |
| 13 | DC max − min during breath ("ΔrespDC") | 0.30 | 33.0 | 0.40 | 44.0 | 0.10 | 11.0 | 100 × .1/.3 = 33.3% vs 60% in AC |
| 14 | DC mean | 153.82 |  | 157.24 |  | 3.42 | 376.2 | 100 × 3.42/153.82 = 2.22%. 100 × 3.42/25.6 = 13.36% (where 25.6 is estimate of baseline) |
|   | For Specific Beat with max Height (peak-trough) during selected Breath | | | | | | | |
| 21 | ACpeak | 154.25 |  | 157.76 |  | 3.51 |  |  |
| 22 | ACtrough | 153.25 |  | 156.75 |  | 3.50 |  |  |

TABLE 9-continued

|   | | Flat | LegRaise | LegRaise-Flat | |
|---|---|---|---|---|---|
| 23 | ACpeak − ACtrough (ACheight @max) | 1.0 | 1.01 | 0.01 | +1.0% |
| 24 | PImax = ACheight/DC @max | 1.0/153.25 =0.00653 =0.653% | 1.01/156.75 =0.00644 =0.644% | −.009 | −.009% [−.009%/.653% = −.013 == 1.3%] |
| 31 | DC at beat with max ACpeak | 153.92 | 157.4 | 3.48 | |
| 32 | DC at beat with max ACtrough | 153.92 | 157.0 | 3.08 | |
| 33 | DC at beat with max ACheight | 153.92 | 157.4 | 3.48 | |
| | For Specific Beat with min Height (peak-trough) during selected breath | | | | |
| 41 | ACpeak | 153.9 | 157.5 | 3.6 | |
| 42 | ACtrough | 153.1 | 156.6 | 3.5 | |
| 43 | ACpeak − ACtrough (ACheight @min) | 0.8 | 0.9 | 0.1 | +12.5% |
| 44 | PImin = ACheight//DC@min | 0.8/153./9 =0.00520 0.520% | 0.9/157.5 =0.00571 =0.571% | .051 | .100 × 051/ .520 = 9.81% |
| 45 | PVI % based on A24 and A44 | =.653 − .520/.653 =.133/.653 =203 = 20.31% | .644 − .571/.644 =.073/.644 =.1134 = 11.34% | | −8.97% [−8.97/20.31 = −44.17] |
| 51 | Diff betw ACpeak at max vs min | 154.25 − 153.9 −153.9 =0.35 | 157.76 − 157.5 −157.5 =0.15 | −0.20 | |
| 52 | Diff betw ACtrough at max vs min | 153.25 − 153.1 =.015-153.1 =0.15 | 156.75 − 156.6 −156.6 =0.15 | 0 | |
| 53 | Diff between ACheight @at max vs min | 1.0 − 0.8 −0.8 =0.2 | 1.01 − 0.9 −0.9 =0.11 | −0.09 | |
| 61 | DC at beat with min ACpeak | 153.62 | 157.0 | 3.38 | |
| 62 | DC at beat with min ACtrough | 153.62 | 157.9 | 4.28 | |
| 63 | DC at beat with min ACheight | 153.62 | 157.9 | 4.28 | |

| B | | Spectral Domain Assessments over given 60 second interval | | | |
|---|---|---|---|---|---|
| | | Amplitude Density During Flat | Amplitude Density During L | Amplitude Density LegR - Flat | % change |
| | Raw Unfiltered (volts): | | | | |
| 101 | Max@Resp Freq. | 3.471 | 4.678 | 1.207 | 1.207/3.471 = 34.773% |
| 102 | Max@Cardiac Freq. | 15.250 | 12.738 | −2.512 | −16.472% |
| | Raw Unfiltered ($AC_{rest}$Mults/Hz) | | | | |
| 111 | Max@Resp Freq. | .247912 | .334134 | =.86222 | 100 × .86222/ .247912 == 34.778% |
| 112 | Max@Cardiac Freq. | 1.089 | .909981 | −.17992 | −16.5216% |
| | DConly: lowpass filter to eliminate AC, <0.5 Hz ($AC_{rest}$Mults): | | | | |
| 121 | Max@Resp Freq. | .2405 26.44 | .3162 34.78 | =.0757 8.344 | 100 × .0757/ .2405 = 31.48% |
| 122 | Max@Cardiac Freq. | None | | | |
| | ACbandstop .01-.5 to eliminate DC respiratory-induced oscillations ($AC_{rest}$Mults) -- time-domain data obtained with Bandstop provided in section C of this Table | | | | |
| 131 | Max@Resp Freq. | .1304 | .1383 | =.0079 =.007917 | 100 × .0079/ .1304 = 6.071% |
| 132 | Max@Cardiac Freq. | 1.061 | .888011 | −.17299 | −16.3044% |
| | AConly to eliminate all of DC ($AC_{rest}$Mults): | | | | |
| 141 | Max@Resp Freq. | None | None | | |
| 142 | Max@Cardiac Freq. | 1.04 | .8885 | −.1636 | −15.6015% |
| | Unfiltered minus DC to isolate AC: (as per AConly filter (rows 141-142) Spectrogram based on pseudocontinuous tracing of ACtrough ($AC_{rest}$Mults/Hz) | | | | |
| 151 | Max@Resp Freq. | 0.28 | .4396 | | |

TABLE 9-continued

| | | Flat | | LegRaise | | LegRaise-Flat | | |
|---|---|---|---|---|---|---|---|---|
| C | | \multicolumn{6}{c}{Max and min of AC during selected Respiration 0.01-0.5 Hz Bandstop Filter} | | % Change |
| | | $AC_{rest}$Mults | $ml_{PPG}$ | $AC_{rest}$Mults | $ml_{PPG}$ | $AC_{rest}$Mults | $ml_{PPG}$ | |
| 201 | maxACpeak | 154.175 | | 157.75 | | 3.575 | | |
| 202 | minACpeak | 154.05 | | 157.70 | | 3.65 | | |
| 203 | Max − minACpeak | .125 | 13.75 | .05 | 5.5 | −.075 | −8.25 | −.075/ .125 = −60% |
| 204 | maxACtrough | 153.40 | | 156.825 | | 3.425 | | |
| 205 | minACtrough | 153.20 | | 156.75 | | 3.55 | | |
| 206 | max − minACtrough | .2 | 22 | 0.075 | 8.25 | −.125 | −13.75 | 100 × −.125/ .2 = −62.5% |
| 207 | Max peak − Min trough w/in resp | 154.175 − 153.2 = .975 | 107.25 | 157.75 − 156.75 = 1.0 | 110 | .025 | 2.75 | 100 × .025/ .975 = 65.06% |
| | | \multicolumn{7}{c}{For Specific Beat with max Height (peak-trough) of signal treated with bandstop filter at 0.01-0.5 Hz} |
| 211 | ACpeak | 154.175 | | 157.75 | | 3.575 | | |
| 212 | ACtrough | 153.25 | | 156.75 | | 3.5 | | |
| 213 | ACpeak − ACtrough (ACheight) @max | .925 | 101.75 | 1.0 | 110 | .075 | 8.25 | 8.108% |
| 214 | PImax = ACheight/DC@max | .95/153.20 =0.6201% | | 1.0/156.825 =.6377% | | 0.0176 | | 17.6% |
| | | \multicolumn{7}{c}{For Specific Beat with min Height (peak-trough) of signal treated with bandstop filter at 0.01-0.5 Hz} |
| 221 | ACpeak | 154.05 | | 157.75 | | 3.7 | | |
| 222 | ACtrough | 153.20 | | 156.825 | | 3.625 | | |
| 223 | ACpeak − ACtrough (ACheight @min) | 0.85 | 93.5 | 0.925 | 101.2 | .075 | 8.25 | 8.824% |
| 224 | PImin = ACheight/DC @min | .85/154.05 =0.5518% | | .925/157.75 =0.5864% | | 0.0346 | | 3.46% |
| | | \multicolumn{7}{c}{For PVI: Based on pulsations (beats) with max and min heights of signal treated with bandstop filter at 0.01-0.5 Hz} |
| 231 | PImax % − PImin % | .06833 | | .05128 | | | | |
| 232 | *(PImax − PImin)/ PImax | .06831/.6201 = 0.1102 = 11.02% | | .05128/.6377 = .08042 = 8.042% | | 3.078% | | |

The following discussion shows how assessment of DC component of the PPG may be achieved with rawPPG whose output is amenable to filtering so as to:

isolate DC (e.g., <0.5 Hz low-pass digital filter),
select DC oscillations with a bandpass (e.g. 0.01-0.5 Hz) digital filter,
selectively eliminate DC oscillations (e.g., 0.01-0.50 Hz bandstop digital filter), and/or
completely eliminate DC (e.g., >0.5 Hz high-pass digital filter or "high" bandpass filter 0.5-5.0 Hz).

These allow for the following DC measurements (along with comparable measurements of AC) constituting a component of inventive embodiments:

increases or decreases of DCmean;
values of DC at its maximum (DC@max) and minimum (DC@min) within a respiratory cycle (single breath) and difference between them (ΔrespDC)
increase or decrease of these values;
amplitude density (or oscillatory power) of changes of DC at the respiratory frequency in the spectral domain (e.g., ΔrespDC in $AC_{rest}$Mults/Hz or in $ml_{PPG}$/Hz).

As in aforementioned embodiments, Applicant uses $AC_{rest}$Mults/Hz and/or $ml_{PPG}$ in order provide the basis for consistent assessment of the raw unfiltered photoplethysmograph ("rawPPG") signal and its components and overcome the lack of interoperability attributable to inconsistent definitions, data presentation and formulae.

Applicant introduces herein formulae which transform isolated measurements of stroke volume (SV) or cardiac output to provide a "preload" component of SV/preload relationships which previously required invasive monitoring (if they were obtainable at all):

Define components of rawPPG and its components and establish uniform units of measurement Assess venous volume Compare increases or decreases of DC with systemic indices of cardiac ejection, for which established clinical assessments include stroke volume, cardiac output, and blood pressure. Ratios introduced herein utilize the measurement of stroke volume (SV)—obtained with a commercially available stroke volume and cardiac output monitor described below—as the representative clinically available measure of cardiac ejection for ratios involving inventive introduction of DC.

e.g., ΔSV/↑DC

Compare ΔrespDC to systemic indices of cardiac ejection (e.g., SV)

e.g., ΔSV/↑ of ΔrespDC

Compare ΔrespDC to established means of assessing respiration-induced variation of AC component of PPG signal Compare increase or decrease DC to increase or decrease ACpeak, ACtrough and ACheight
Compare ΔrespDC to Δresp of AC parameters
Compare increase or decrease of AC as a consequence of DC to increase or decrease of systemic indices Perform said assessment(s) at multiple sites Applicant describes inventive embodiments upon accessing initially unfiltered data using a $rawPPG^{Forehead}$, $rawPPG^{Finger}$ and $rawPPG^{Ear}$. Applicant focuses primarily on $rawPPG^{Forehead}$ (since forehead is a central site that does not require a clip to maintain positioning as would $PPG^{Ear}$) during a recommended sequence of passive head raise, passive leg raise (LegR), head up/legs down tilt, and head down/legs up tilt. Applicant focuses primarily on LegR (achieved with 45° wedge under thighs) because it was the only postural challenge that did not involve changing level of the head relative to the heart and central venous vessels.

As introduced above, Applicant relied primarily on $AC_{rest}$Mults and $ml_{PPG}$. As described above, the former was based on calibration of given PPG at a given site prior to the onset of challenges, such that 1 $AC_{rest}$Mult=0.014 volts for $PPG^{Forehead}$ in the representative subject. The latter was based on stroke volume at $_{rest}$ ($SV_{rest}$) of 110 ml, obtained with concurrent application of a noninvasive cardiac output monitor (NICOM, Cheetah Medical, Cambridge Mass.) such that 1 $SV_{rest}$Mult=110 ml=1 $AC_{rest}$Mult=110 $ml_{PPG}$.

It should be noted that, in the absence of a clinically approved rawPPG, Applicant relied upon a research device which had the major limitation of containing the infrared light source at the level of the skin; this posed a risk of causing injury under a drape and thus was not utilized in anesthetized patients or in trauma settings.

Figure 32:
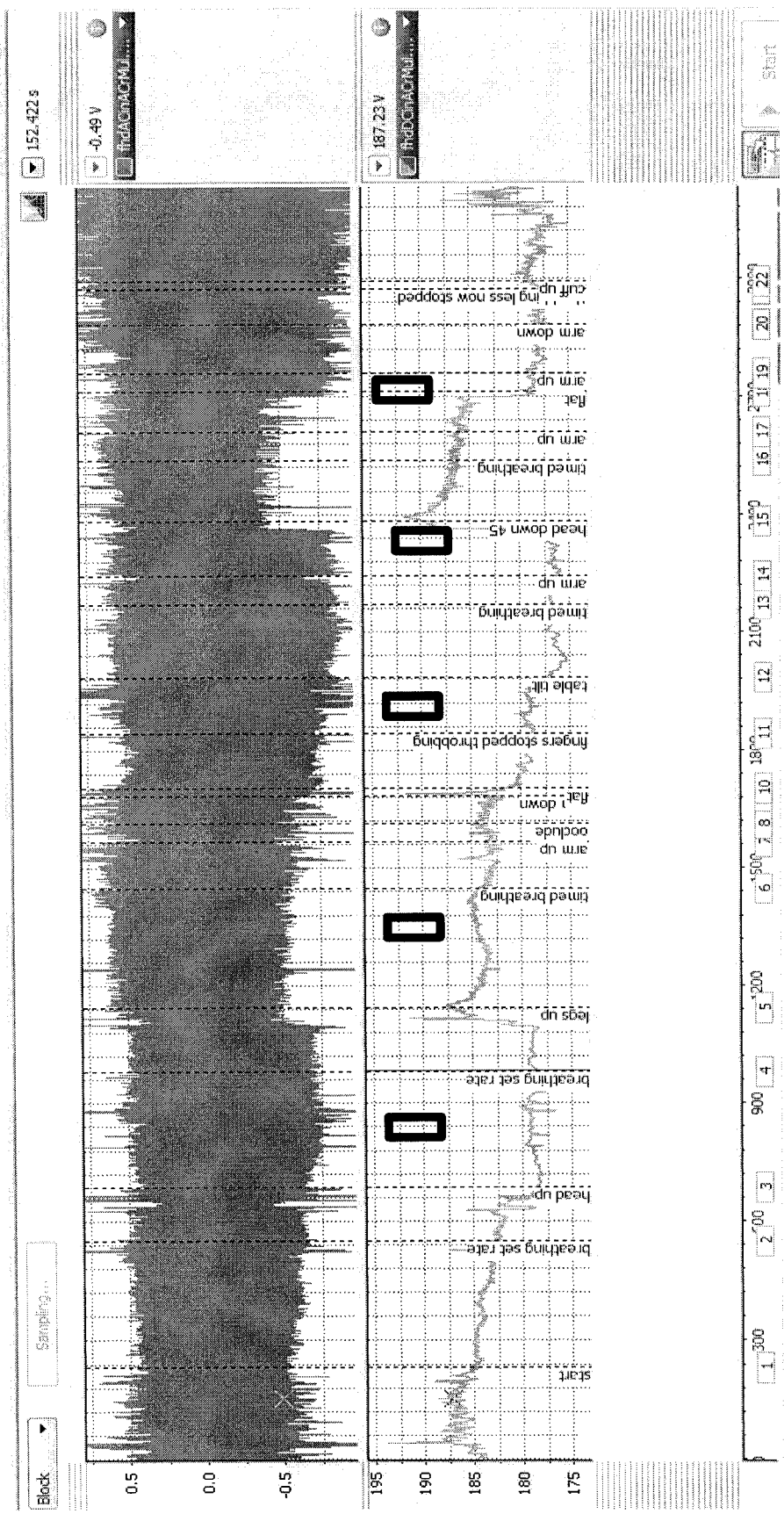
FIG. 32 is screen print of AC in $AC_{rest}$Mults and DC in $AC_{rest}$Mults of $PPG^{Forehead}$ for entire study during a series of postural changes: head up, legs raised (legR), head up/leg down tilt, head down/legs up tilt. Numbers 1-22 identify time points of interventions, also listed as vertical text (typically 10 seconds after start of a new event). Values on y-axes represent number of $AC_{rest}$Mults (based on normalizing to AC@rest calibrating voltage). Background not subtracted from DC values.
Figure 33:
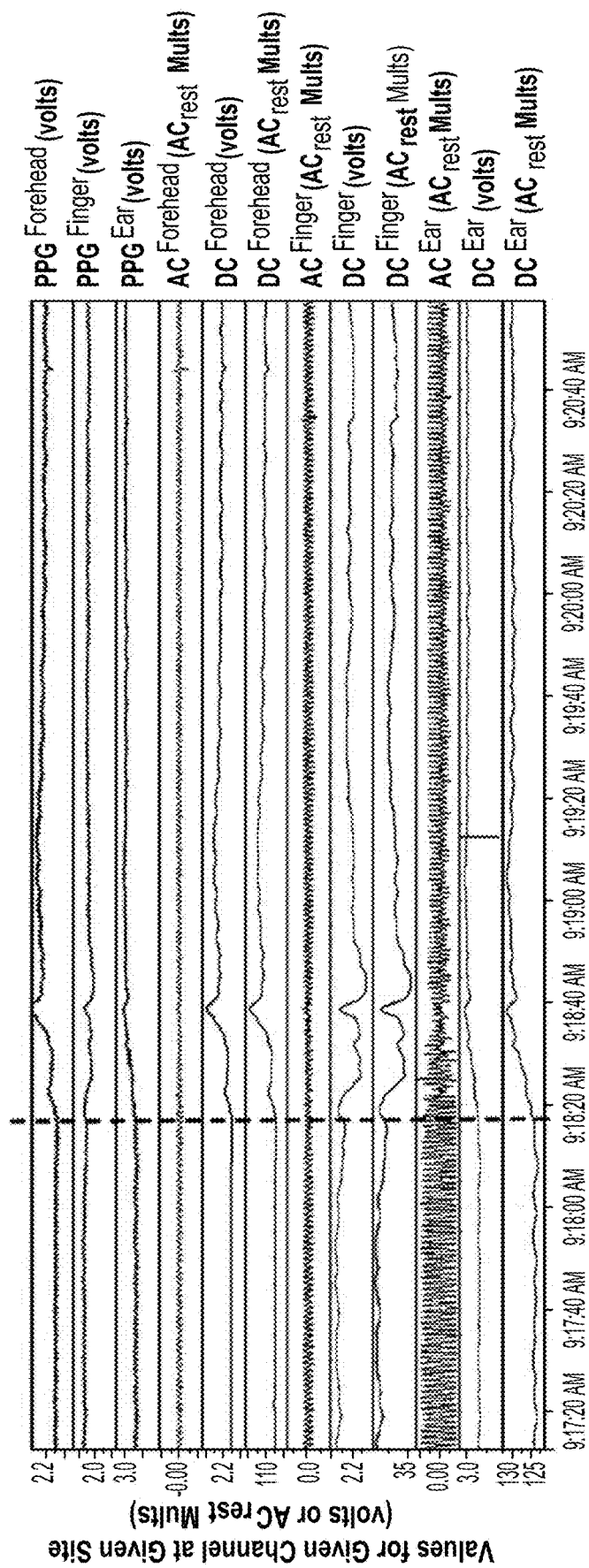
FIG. 33 is a screen print of data from three monitoring sites: forehead (a central site), ear (a central site) and finger (peripheral site) before and during leg raise (LegR). The dashed line represents onset of leg raise. The top three channels show raw values for each site. Subsequent triads show AC in $AC_{rest}$Mults, DC in volts and DC in $AC_{rest}$Mults for given PPG at forehead, finger and ear. Unless otherwise stated in this and subsequent figures:
  a. AC identified with a "high" bandpass filter between 0.5-5.0 Hz that encompasses frequency of pulse rate (rate of 60/min would correspond to 1 Hz);
  b. DC identified by low pass, <0.5 Hz filter that encompasses static blood and blood oscillating at respiratory and autonomic frequencies (typically between 0.1 and 0.3 Hz).

FIG. 32 shows screen print of PPG indices commonly assessed in the instant invention: AC in $AC_{rest}$Mults and DC in $AC_{rest}$Mults of $PPG^{Forehead}$. As can seen, they may change in opposite directions throughout the entire study, including the four major postural changes: head up (time point #3 identified at bottom of figure), legs raised (LegR) (#5), head up/leg down tilt (#12), head down/legs up tilt (#15). The physiologic relevance of changes in venous volume (representing preload) and SV or AC (representing volume ejected by the heart with each pulsation) is a major reason why the embodiments related herein are vital to clinical care. Values on y-axes represent number of $AC_{rest}$Mults (background not subtracted from DC values; as shown in above, zeroing can be attained by applying pressure to the monitoring site or adapting values established in other subjects). Consistent with findings during lower body negative pressure, the central sites (forehead and ear) responded similarly. However, as seen in FIG. 33, finger responded differently to LegR (time pt #5) and other challenges.

Figure 34:
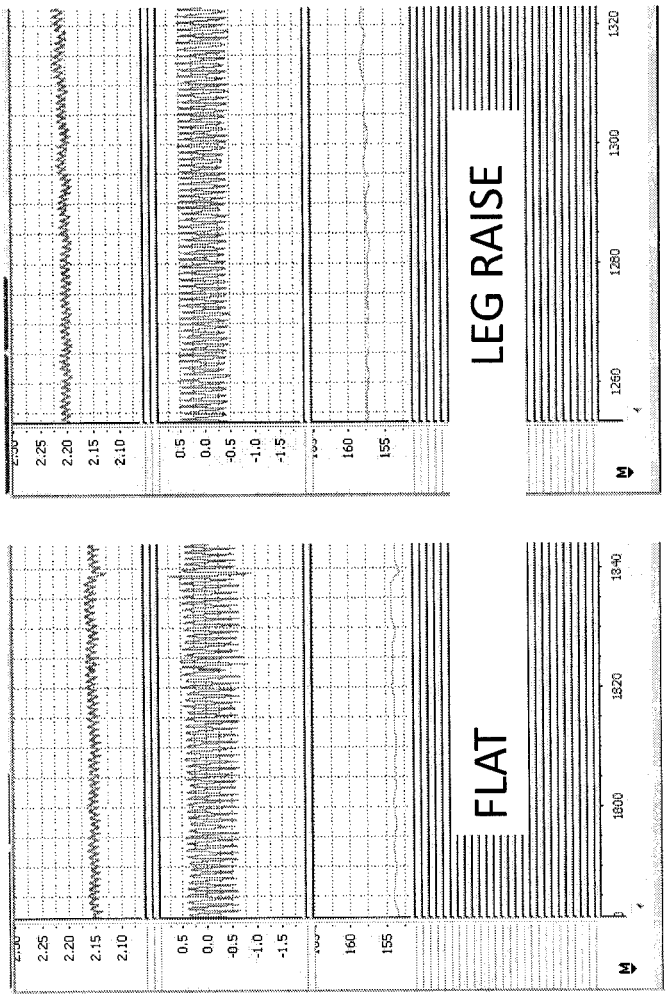
FIG. 34 are screen shots during Flat and LegR phases for the 60 seconds beginning approximately (~) 120 seconds after onset of given phase. The comparison shows increase in raw signal (in volts), minimal change in AC (in $AC_{rest}$Mults) and increase in DC (of approximately 3.4 $AC_{rest}$Mults).
Figure 35:
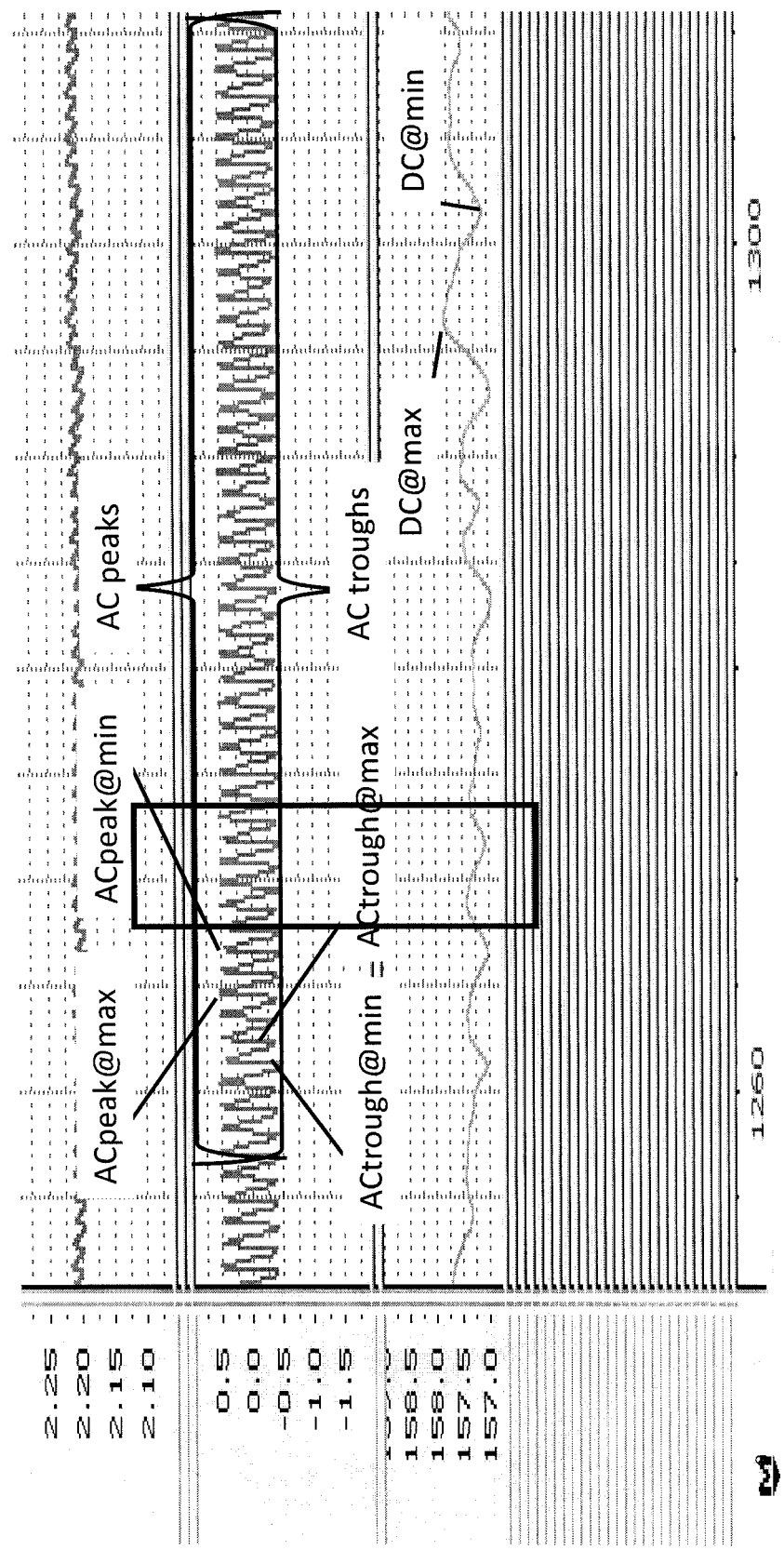
FIG. 35 is a screen shot identifying measurements as basis for prior art and inventive formulae during 60 second intervals during LegR (as well as during Flat). Channels relate unfiltered raw photoplethysmograph ("rawPPG") in volts, AC in $AC_{rest}$Mults, and DC in $AC_{rest}$Mults. Rectangle delineates breath selected for detailed analysis.

Table 8 lists corresponding values obtained by clinically available noninvasive cardiac output monitor (NICOM) and continuous blood pressure monitoring for the entire study. Prior art indices (without benefit of comparison to DC) include SV, BPsystolic and BPdiastolic (blood pressure). As would be expected during transfer of blood from legs to the central circulation (e.g., LegR and head-down tilt), BPsys (systolic blood pressure) and SV all increased; heart rate, which increases as compensation for hypovolemia and decreases during volume replacement, decreased in response to increased volume due to LegR Consistent with Applicant's arguments as to the importance of DC, FIG. 34 shows that the greatest changes are seen in DC in the real-time data obtained for the segments between 90 and 150 seconds after start of Flat and LegR phases for rawPPG in volts, AC in $AC_{rest}$Mults, and DC in $AC_{rest}$Mults. The points on the tracing of greatest relevance to the instant invention are named in FIG. 35 over the course of a 60-second segment.

Figure 37:
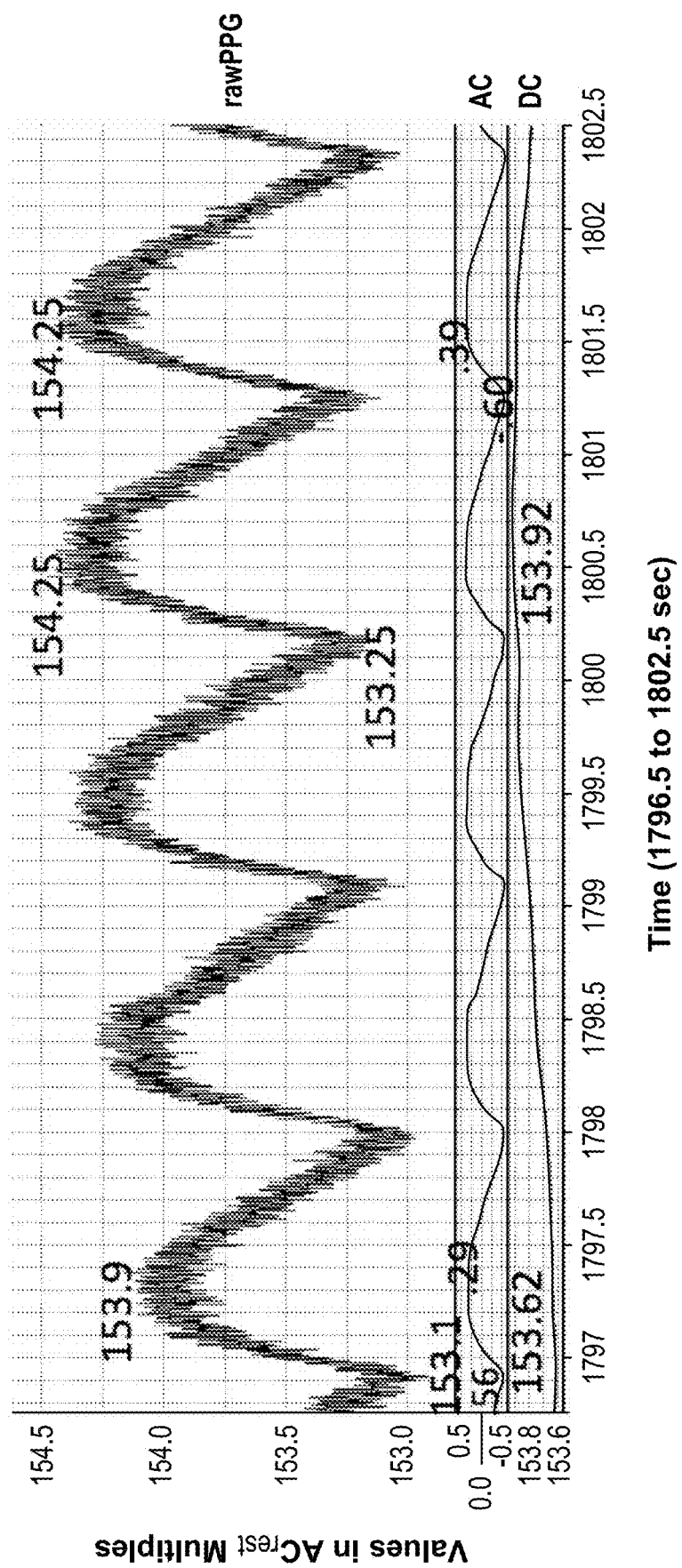
FIG. 37 is a screen shot showing single breath selected for analysis during Flat for rawPPG in $AC_{rest}$Mults, AC in $AC_{rest}$Mults, and DC in $AC_{rest}$Mults. Values in the top channel correspond to peak and trough of raw signal in ($AC_{rest}$Mults) during their maximum and minimum during given breath. Values in the middle channel relate ACpeak (that is, the peak of the AC component of the PPG signal) and ACtrough (that is, the low point of the AC component of the PPG signal) in AC only signal. Values in bottom channel show maximum and minimum of DC during the breath.

The tracing obtained during Flat is shown for 60 seconds in FIG. 36 and for a representative breath in FIG. 37. Values used for exemplary analyses in accordance with the present invention are summarized in Table 9 for:

Rows 1-7: AC over course of a breath:
Rows 11-14: DC over course of a breath;
Rows 21-24: AC for Specific Beat with max Height (peak-trough) during selected breath
Rows 31-33: DC for Specific Beat with max AC values during selected breath
Rows 41-44: AC for Specific Beat with min Height (peak-trough during selected breath
Rows 51-53: Differences in AC between max and min during breath Rows 61-63: DC for Specific Beat with min AC values during selected breath Likewise, the tracings obtained during LegR are shown for 60 seconds in FIG. 38 and for a representative breath in FIG. 39. In order to delineate selected embodiments, the increases, decreases, and % changes are provided in right-sided columns of Table 9.

DC increased from 153.82 $AC_{rest}$Mults during the Flat segment to 157.24 $AC_{rest}$Mults during LegR (row A14 of Table 9). The increased DC of 3.42 $AC_{rest}$Mults, which converted to 376.2 $ml_{PPG}$ and thus was consistent with increases of venous volume (250-500 mil) reported by investigators using noncontinuous and invasive monitoring (as opposed to inventive continuous noninvasive technique) during LegsR, was approximately 13.36% of presumed systemic capillovenous volume of ~25.6 $AC_{rest}$Mults shown above (~3200 $ml_{PPG}$). Such normalizing to a value for DCblood was introduced earlier in this disclosure.

Embodiments Related to DC Component of Preload/Stroke Volume Relationship

Such quantification of increases in DC provided a heretofore unavailable noninvasive foundation by which to assess challenge—or intervention—induced change (e.g., LegR-induced increase) of stroke volume (SV). As summarized in Table 8, SV, as measured by clinically established commercial cardiac output monitor (NICOM), increased from 130 ml at Flat to 160 ml during LegR (wherein the 30 ml increase corresponds to a 21% increase above Flat and an increase of 0.273 $SV_{rest}$Mults (based on $SV_{rest}$=110 ml, wherein $SV_{rest}$Mult is defined by ratio of given SV value to SV at rest). Heretofore, in the absence of invasive monitoring, this typically constituted a stand-alone measurement such that clinician and investigator could not noninvasively relate a change in the volume ejected by the heart with an assessment of overall volume and hence preload to the heart (or change thereof). Comparative noninvasive cardiac ejection/preload ratios generated herein using comparable units for SV and DC include:

↑SV of 30 $_{ml}$/↑DC of 376.2 mlPPG (row A14);
↑SV of 0.273 $SV_{rest}$Mults/↑DC of 3.42 $AC_{rest}$Mults (row A14); and
↑SV of 21%/↑DC of 13.3% (row A14, based upon assumed value of 25.6 $AC_{rest}$Mults for capillovenous blood at $PPG^{Forehead}$ at rest or one may perform zeroing of specific PPG (as described above).

These changes would place the subject in the right upper quadrant of an SV/DC (or physiologically related variation thereof) quadrant map as shown during recovery after lower body negative pressure (see FIG. 22); efficient placement therein and certainly precision of placement therein previously was precluded in the absence of the assessment of venous (DC) volume.

A given quadrant can be subdivided into sectors based upon cutoffs for normal, as discussed below. As shown herein, a normal response is not necessarily a 1:1 relationship. Quadrant assignment and breakdown within quadrant can guide therapy; e.g., add/remove fluid, increase contractility, vasodilation or vasoconstriction, change ventilator-delivered volume and pressure; inventive embodiment-enabled assessment of venous volume is critical to these determinations.

It is also apparent that the use of inventive conversions ($ml_{PPG}$ and $AC_{rest}$Mults) provides intuitive, interoperable units for these ratios and that inventive establishment of 25.6 $AC_{rest}$Mults as baseline for DC (along with 1 $AC_{rest}$Mult as baseline for AC) enables heretofore unavailable measurements of relative change.

The values also provide bases for displaying on other axes, e.g., where readings or Δreadings (besides change from baseline) are displayed for one time or serial assessment as well as cumulation of data for multiple subjects. The values also provide bases for determining whether a given subject's response is above, or below a cutoff established to identify favorable (or unfavorable) response to intervention based on cumulation of data using inventive embodiments with clinically suitable PPGs; pending that, for purposes of illustration the response of the healthy volunteer are used herein as surrogate cutoffs. For example, based on above data, a "cutoff" for a positive response to fluid would be:

$SVml/DCml_{PPG} \geq 0.0797$ or $\geq 8.0\%$;

$SV_{rest}Mults/AC_{rest}Mults \geq 0.0798 \geq 8.0\%$;

%↑SV/%↑DC=1.579 or ≥160%

Determination of cutoffs enables division of quadrants of quadrant map into above and below cutoff sectors for more precise assignment of a given patient at given time as well as to group serial or multipatient assessments.

Clearly, one need not rely on SV for a systemic measurement. For example, it was noted that systolic blood pressure (BP) increased by from 118 during Flat to 122 mmHg during LegR (Table 8), providing a ratio of %↑BP/%↑DC of 3.4%/13.3%. (Table 8, row A14 of Table 9). Likewise one could use cardiac output (which is SV×heart rate). Throughout the following descriptions, it should be appreciated that, except when measurements of SV are provided, relationships of SV/DC and ΔSV/DC refer to the relationship of SV as well as other measures of cardiac ejection to DC.

One similarly can compare measurements of compensation (such as change in heart rate (HR), HR variability, or peripheral vascular resistance) in response to a change in venous volume that in the absence of present invention of DC measurement would not be quantifiable by noninvasive monitoring.

For example, a user can also compare HR and DC, wherein increased HR is an indication of increased sympathetic activity to maintain SV and/or blood pressure. In the volunteer discussed above with reference to Tables 8 and 9, HR decreased by 1.8% during to LegR, providing a %ΔHR/%ΔDC ratio of −1.8%/+13.3%. Conversely, in the context of blood loss, increased HR is a marker of the amount of sympathetic activation that has maintained SV and blood pressure. During head up tilt (which pools otherwise active blood into the legs, thereby simulating blood loss) in the present example, HR increase by 5.6%. Viewing the change in HR in the context of the change in DC (shown for head up tilt later in this disclosure) has an added benefit in awake patients who have suffered trauma: a disproportionate increase in HR without a decline in DC would indicate pain and anxiety as opposed to volume loss.

In that responder studies (and related measures of active volume status and "response" to fluid administration) commonly rely on changes in respiration-induced variation of cardiovascular waveforms (due to changes in lung volumes and pressures within the chest), Applicant herein introduces comparison of ΔrespSV/↑ or ↓DC, and subsequently introduces and documents respiration-induced changes in DC (introducing herein ΔrespDC, for comparison to oscillating as well as persistent changes in DC) in the interoperable units introduced herein and thereby provide a foundation for what Applicant believes were seriously flawed prior art assessments of mean variations of AC, BP or SV as may be induced by respiration (or, if desired, another inducer of change such as autonomic activity)(see U.S. Pat. No. 7,367,941 to Silverman DG & Stout R G, entitled "Detection And Characterization Of Cholinergic Oscillatory Control In Peripheral Microvasculature," which is incorporated by reference). Consistent with spontaneous ventilation in a normovolemic subject, changes were relatively small compared to those seen with positive pressure ventilation in the context of actual blood loss (not appropriate in a healthy volunteer who was not sedated or anesthetized). As was the case for isolated measures of SV above, except when inventive monitoring was employed to estimate end diastolic volume (consistent with venous volume), to the best of Applicant's knowledge, no one has used the PPG let alone noninvasive monitoring to provide a venous component and thereby convert an isolated reading of SV variation (or cardiac output, BP or AC variation) to a ratio with DC as denominator.

In the present example, the cardiac output monitor documented a decrease in SV variability during the respiratory cycle (ΔrespSV, expressed by NICOM as SVV %) from 16% to 12% (25% decline). The inverse relationship of changes in SVV % as a consequence of increases in DC were based on comparison of SVV % and DCmean, including:

↓SVV % of 25%/↑DC of 13.3% (based upon row A14 of Table 9).

As per the above description of quadrant placement, this would in the right lower quadrant of map akin to FIG. 22, wherein tentative cutoff for a responder would be a ratio≥−188%. Alternative axes may be employed; e.g., to show that ↓SVV % is a positive response to volume administration.

Ideally, assessment SV variability would be on a beat by beat basis but this was not enabled by the eight beat sampling window of the cardiac output monitor. This is just exemplary. Other measures of variability (e.g Δ systolic blood pressure, —A cardiac output) and components of the DC tracing during the respiratory cycle (e.g., maximum and/or minimum as per rows A11-14 of Table 9) can be used.

Embodiments Related to ΔrespDC and SV

Figure 38:
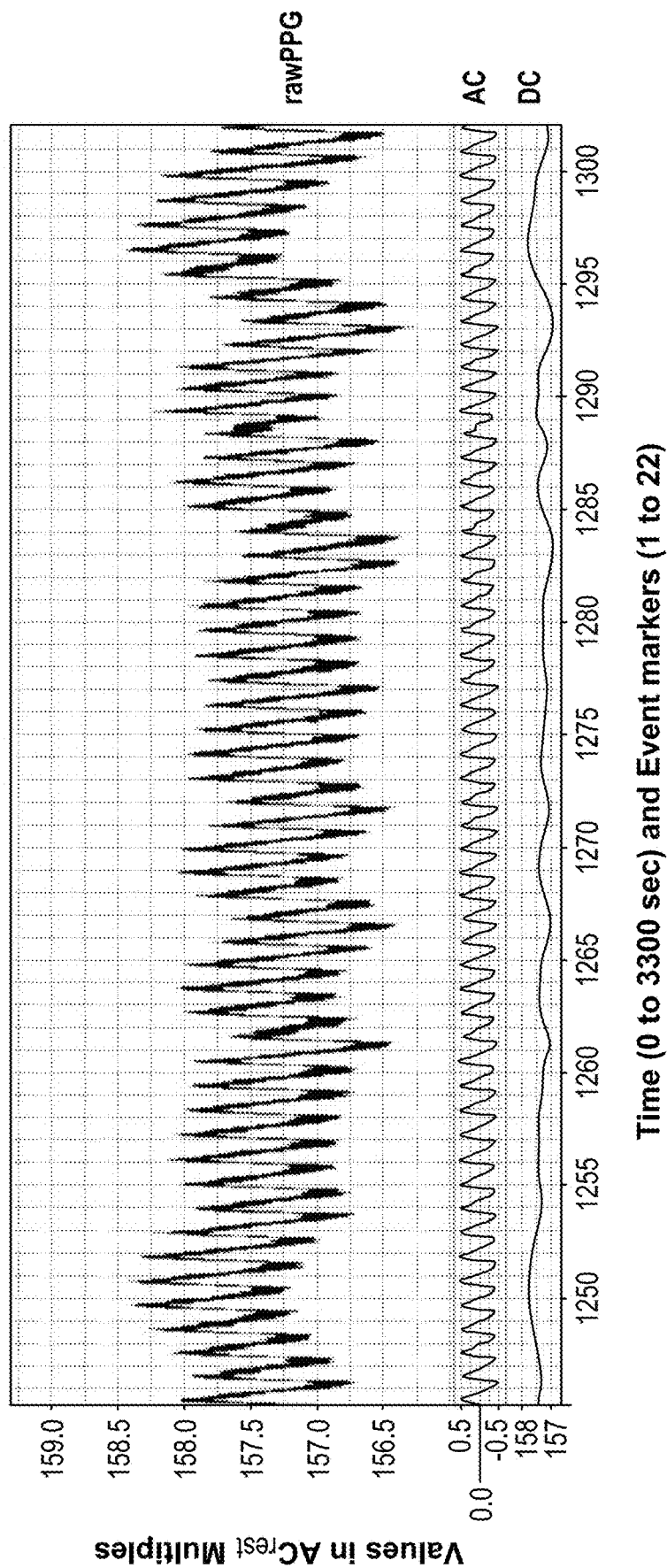
FIG. 38 is a screen shot showing 60 seconds selected for analysis during LegR for rawPPG in $AC_{rest}$Mults, AC in $AC_{rest}$Mults, and DC in $AC_{rest}$Mults.
Figure 39:
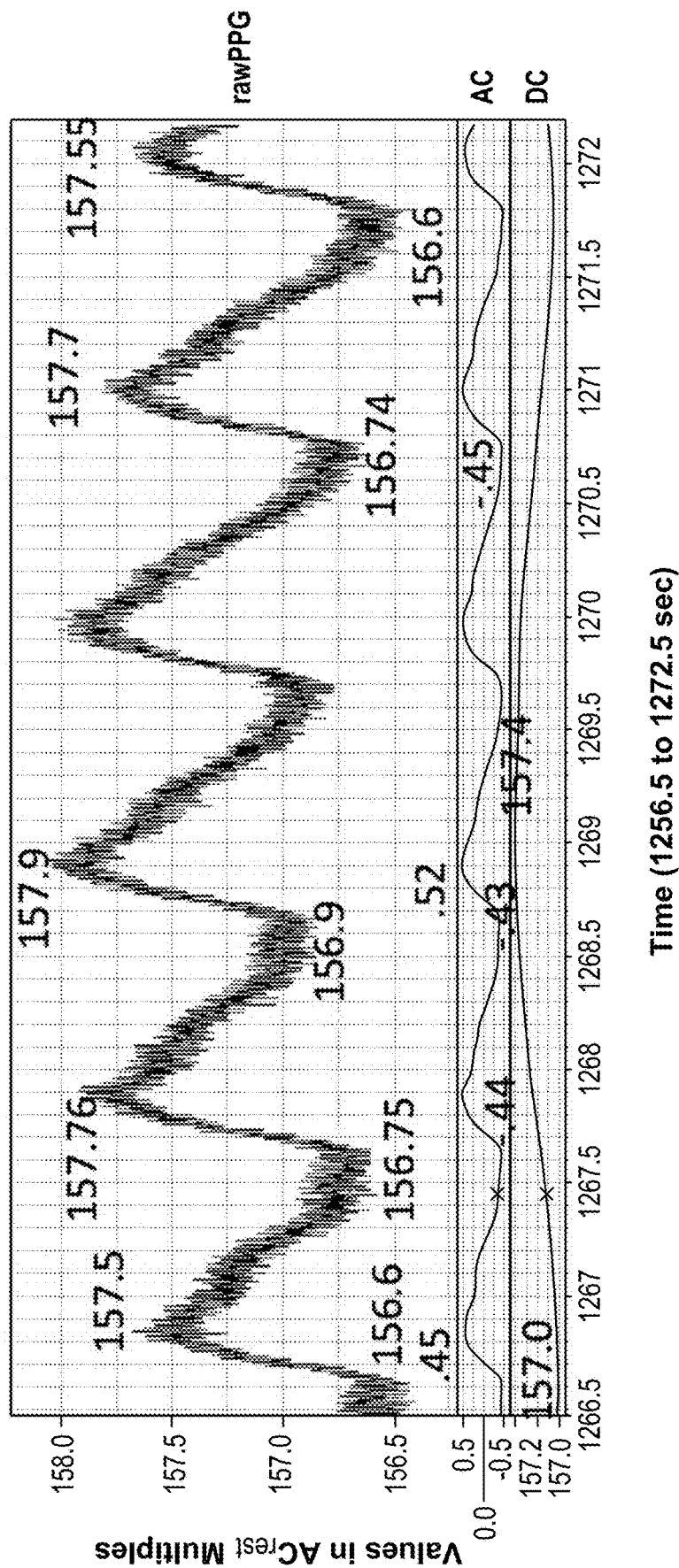
FIG. 39 is a screen shot showing single breath selected for analysis during LegR for rawPPG in $AC_{rest}$Mults, AC in $AC_{rest}$Mults, and DC in $AC_{rest}$Mults. Values in the top channel correspond to peak and trough of raw signal in ($AC_{rest}$Mults) during their maximum and minimum during given breath. Values in the middle channel relate ACpeak and ACtrough in AC only signal. Values in bottom the channel show maximum and minimum of DC during the breath.

In addition to causing an increase of mean DC, LegR also caused an increase in the difference between the maximum and minimum values for DC (DC@max and DC@min) during each respiratory cycle (breath) (rows A11-14 of Table 9) as well for the specific beats with maximum and minimum values during a given breath (rows A31-33 and A61-63 of Table 9, respectively). ΔrespDC increased by 0.10 $AC_{rest}$Mults (from 0.30 during Flat to 0.40 during LegR) in the selected respiratory cycle (bottom channels showing DC in FIGS. 36 and 37 respectively showing full 60 seconds and single breath during Flat and in bottom channel showing DC in FIGS. 38 and 39 respectively showing full 60 seconds and single breath during LegR.

Figure 40:
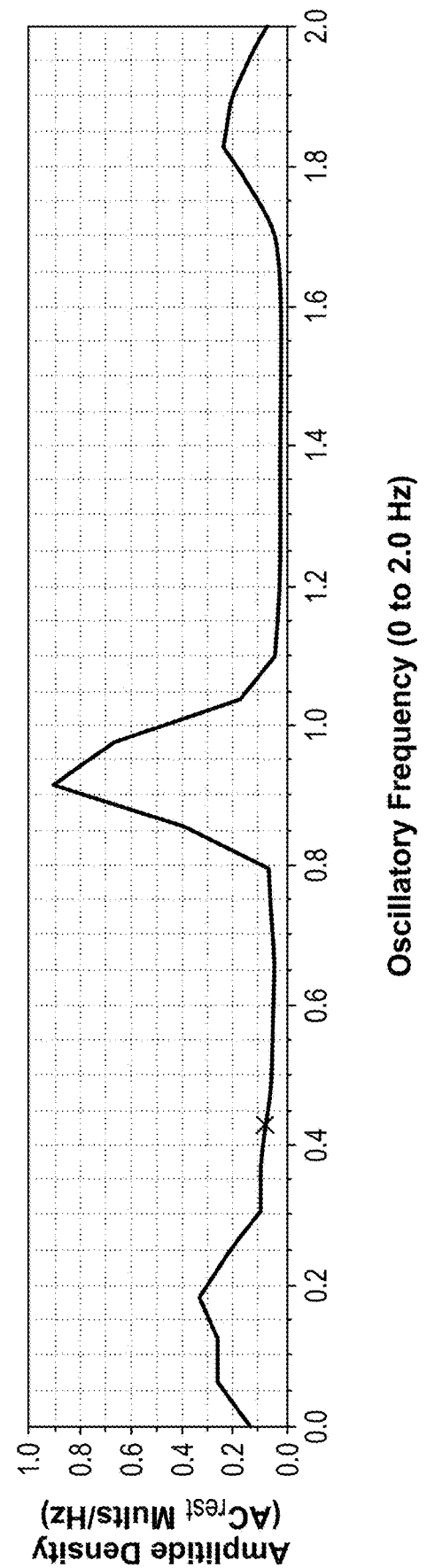
FIG. 40 is a screen shot of spectral domain analysis of 60 second interval during LegR of rawPPG signal in $AC_{rest}$Mults: amplitude density at 0.916 Hz represents cardiac pulsations (at approximately 55 beats/minute), and amplitude density at low frequencies represents impacts of respiration and autonomic activity on AC and DC signals.
Figure 41:
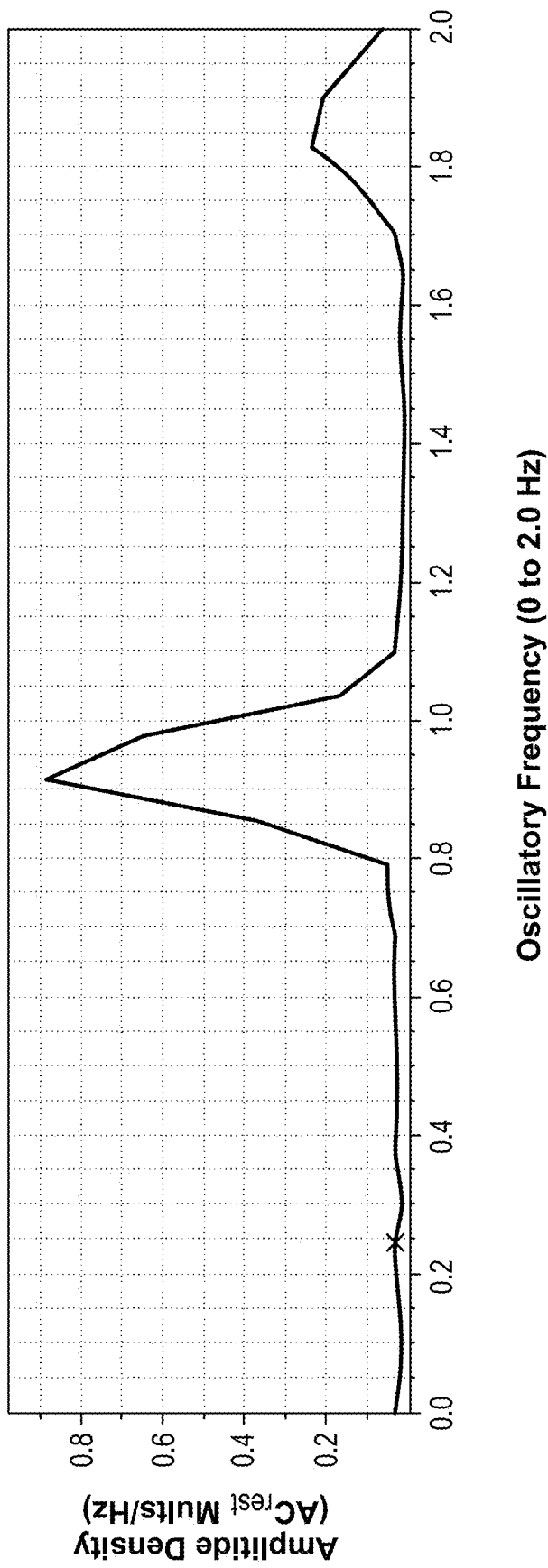
FIG. 41 is a screen shot of spectral domain analysis of 60 second interval during LegR of AC channel showing exclusive peak at cardiac pulsatile frequency (0.916 Hz) and harmonic.
Figure 42:
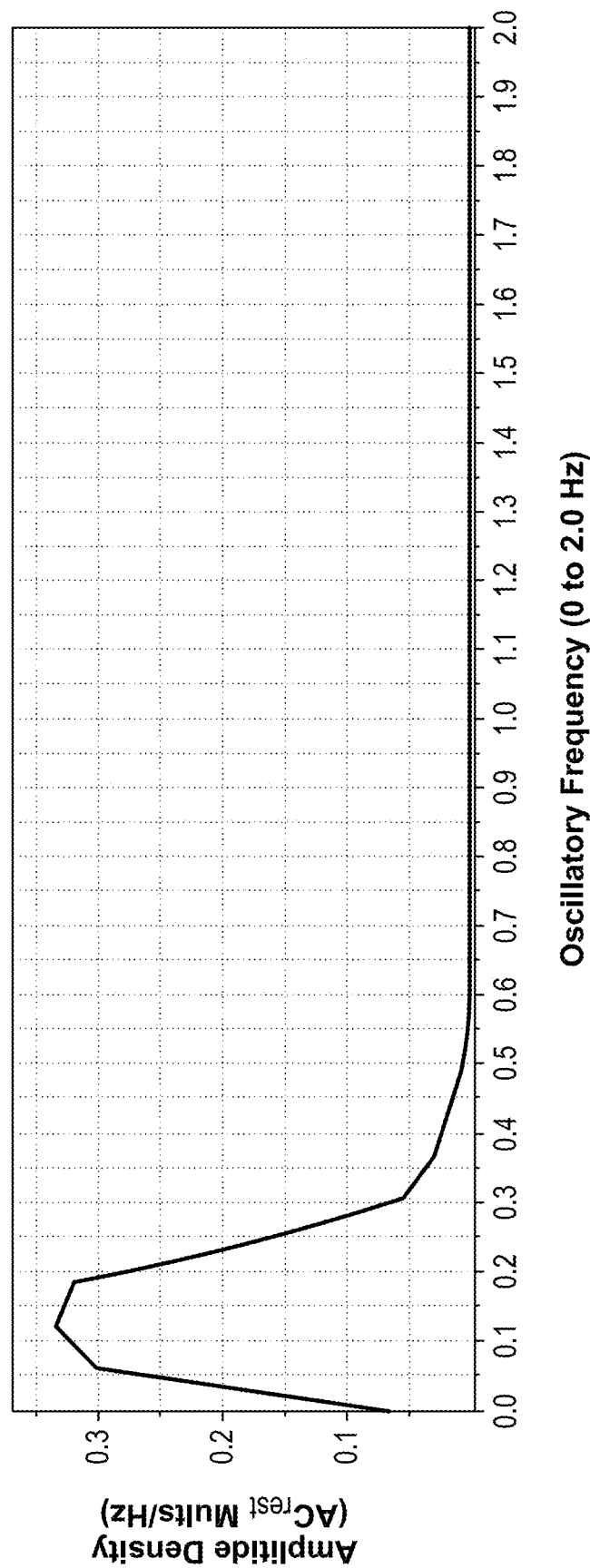
FIG. 42 is a screen shot of spectral domain analysis of DC channel of 60 second interval during LegR showing virtually exclusive peak(s) in low frequency range due to impact of respiration and autonomic activity. As noted in the display, the zero frequency component has been removed for the spectral domain displays so as to note compromise display of oscillatory frequencies. However, it can provide a mean value with which to normalize amplitude densities (even if not shown). Use of $AC_{rest}$Mults provides clear appreciation of the magnitude of oscillations (0.33 $AC^{rest}$Mults).

As noted above with reference to FIGS. 29 to 31, use of $AC_{rest}$Mults and $ml_{PPG}$ allows for transparent conversion from time domain to spectral domain of oscillatory amplitudes at frequency of interest, e.g., respiration-induced variation as shown in FIGS. 40, 41, and 42. As shown during LegR, integration by spectral domain analysis of the DConly channel (FIG. 42) generated similar findings (rows B121-122 of Table 9) to the time-domain measures, identifying an LegR-induced ΔrespDC increase of 0.0757 $AC_{rest}$Mults/Hz (from 0.241 to 0.316) at the respiratory frequency over the 60 second segment; this corresponded to a ΔrespDC increase of 8.344 $ml_{PPG}$/Hz as a consequence of LegR (from 26.44 to 34.78). The 31.48% increase of respiratory-induced amplitude density (over 60 second interval) (row B121 of Table 9) was remarkably similar to the 33.3% increase in max-min DC calculated for single breath with time domain analysis (row A13 of Table 9). Of note, again it was recognized that, while maintaining relative amplitude densities among frequencies and between Flat and LegR phases, conversion to $AC_{rest}$Mults (and/or $ml_{PPG}$) transformed obscure voltages of traditional spectral displays to interoperable physiologically meaningful measures. The (small) difference between row B121 and A13 values is attributable to the former incorporating the entire 60 second study interval as opposed to a single breath.

Thus, in addition to assessing the (inverse) relationship between the increases in DC and ΔrespSV (recorded by NICOM as SVV %) during LegR, Applicant also has documented the (inverse) relationship between ΔrespDC and ΔrespSV. Exemplary embodiments of the multiple potential ratios are provided (using $AC_{rest}$Mults for these examples), in anticipation that, after assessing them in clinical settings, clinical authorities will determine which is/are most applicable:

ΔrespSV % during Flat/ΔrespDC during Flat=16%/0.30 $AC_{rest}$Mults (row A13 of Table 9)—assuming this would be maintained in a large population, the ratio suggests that a ratio of 53.33% constitutes a normal ΔrespSV %/ΔrespDC relationship during a resting state ΔrespSV % during LegR/ΔrespDC during LegR=12%/0.40 $AC_{rest}$Mults (row A13 of Table 9)

Δ of ΔrespSV % LegR-Flat/Δ of ΔrespDC LegR-Flat=–4%/0.10 $AC_{rest}$Mults (row A13 of Table 9). An inverse relationship, e.g., ↓ of ΔrespSV % and ↑ of Δresp DC, would place ΔrespDC would place patient in right lower quadrant. Conversely ↑ of ΔrespSV % would place patient in left upper quadrant. A tentative cutoff for adherence to the inverse relationship would be = –40%

%Δ of ΔrespSV % LegR-Flat/%Δ of ΔrespDC % LegR-Flat=–25%/+33% (row A13 of Table 9). A tentative cutoff for adherence to the inverse relationship would be –75.8%.

Clearly, respiration-induced changes in amplitude density could be intuitively applied if $AC_{rest}$Mults and $ml_{PPG}$ are used instead of raw voltages. Exemplary ratios using amplitude densities include:

ΔrespSV % during Flat/ΔrespDC during Flat=16%/0.241 $AC_{rest}$Mults/Hz (row B121 of spectral domain display as shown in Table 9)

ΔrespSV % during LegR/ΔrespDC during LegR=12%/0.316 $AC_{rest}$Mults/Hz (row B121 of Table 9)

Δ of ΔrespSV % LegR-Flat/Δ of ΔrespDC LegR-Flat=–4%/0.076 $AC_{rest}$Mults/Hz (row B121 of Table 9) (=–52.6%)

%Δ of ΔrespSV % LegR-Flat/%Δ of ΔrespDC % LegR-Flat=–25%/+31.48% (row B121 of Table 9) (=–0.794=–79.4%)

It is evident that assessment of the impact of a volume challenge on preload may also be appreciated by integrating the % increase or decrease of nonoscillating (respiration-independent) DC with the %Δresp of oscillatory (respiration-dependent) DC e.g. combined impact=%↑DC+%↑ΔDC.

One similarly can measure impact of an increase or decrease in DC on an increase or decrease of ΔrespDC.

In addition, Applicant shows below that respiration-induced changes not only directly impact DC but also may directly impact ACtrough; however, for purposes of clarity, Applicant has not addressed this distinction in the aforementioned ratios (but does so below).

Returning to the limitations of AC and DC as summarized in Table 1:

AC is impacted by attenuation but not background;

DC is impacted by attenuation as well as background.

Conversion to $AC_{rest}$Mults and/or $SV_{rest}$Mults (in $ml_{PPG}$) eliminates impact of attenuation on DC and AC as does use of an alternative voltage/voltage ratio such as ↑AC/ACpre, ↑DC/DCpre, or %↑DC. However, impact of background on DC persists unless one distinguishes DCblood from DCbackground for the given PPG at the given site (e.g., zeroing) or one measures the difference between two DC values. In light of these limitations, voltages may be used in only some of the above formulae, most notably when % change is determined.

Within a single subject one can compare inventive ratios based upon DC values in volts; however, this is of negligible usefulness for a single measurement especially if background is not subtracted; and it lacks interoperability and ready translation to clinical utility. Regardless, the introduction of AC/DC ratio in accordance with the present invention is novel even if voltage is used.

As noted above, calculation of %↑DC or %↓DC requires that the denominator ($DC_{pre}$) be DCblood not DC (which is DCblood+DCbackground). The value for DCpre can be based upon measured voltages at given PPG for DCblood and DCbackground during zeroing such that one can obtain DCblood@rest and DCbackground; DCbackground can be subtracted from each DC reading (since it remains constant).

Zeroing provides DC@rest and enables conversion of subsequent DCblood values at the given PPG not only in $AC_{rest}$Mults as utilized throughout this application but also to multiples of DC@rest wherein DCblood of the new reading may be measured as differences between DC readings and/or by subtracting DCbackground from a given DC reading (as per FIG. 5). As stated in FIG. 6 as discussed above, because it is independent of background, ΔDC=ΔDCblood.

As stated above, to determine DCbackground for subsequent subtraction for DC readings requires the same maneuver (zeroing) as shown above to determine DCblood@rest. In the example of zeroing shown in FIG. 4, drop corresponding to DCblood is approximately 0.7 volts and DCbackground is ~2.0 volts (with a realization that the range of PPG commonly is from –10 to +10 volts); hence, while DCbackground in volts can be subtracted from all values as shown in FIG. 5, DCbackground or "DC" should not be used as a numerator or denominator in ratios—only DCblood is applicable).

Consistent with disclosure above, capillovenous blood likely is ~3200 ml at rest, such that DCblood@rest can be set to be equivalent to 3200 mlPPG (unless otherwise calibrated). This is akin to AC@rest=1 $AC_{rest}$Multiple which corresponds to distribution of SV@rest. This offers the added advantage that DCblood@rest can be estimated as 25.6 times AC@rest under baseline conditions.

Alternative calibration can be achieved by establishing change in DC in response to a given challenge, e.g., the voltage decline upon withdrawal of 100 ml of blood from a healthy subject. For the given PPG at given site in given subject, one would appreciate that subsequent readings can be compared in accordance with the established volts/ml relationship.

In order to express ΔrespDC as a relative change at the level of the right atrium and thus introduce embodiment(s) more related to preload within the heart (not previously available noninvasively), Applicant expressed ΔrespDC at each segment as a % of estimated right atrial (RA) volume (70 ml in accordance with invasive monitoring in the literature): 31.4% during Flat (100×22 $ml_{PPG}$/70 ml) and 50.3% during LegR (100×35.2 $ml_{PPG}$/70 ml). This delineated the following relationships:

$\Delta$ of SVLeg$R$-Flat/$\Delta$respRA Leg$R$-Flat=30 $_{ml}$/13.2 $ml_{PPG}$=30$_{ml}$/+18.9%

%$\Delta$ of SVLeg$R$-Flat/%$\Delta$ of $\Delta$respRA % Leg$R$-Flat=21%/+60.2%

SVV % during Flat/$\Delta$respRA % during Flat=16%/31.4%

SVV % during LegR/$\Delta$respRA % during Leg$R$=12%/50.3%

$\Delta$ of SVV % Leg$R$-Flat/$\Delta$ of $\Delta$respRA % Leg$R$-Flat=−4%/+18.9%

%$\Delta$ of SVV % Leg$R$-Flat/%$\Delta$ of $\Delta$respRA % Leg$R$-Flat=−25%/+60.2%

As above, values can be graphed in quadrant map (above and below theoretical cutoff line).

DC vs AC

DC vs ACtrough:

Before addressing the impact of DC on AC, Applicant first shows comparison of DC to ACtrough. Values of DC and ACtrough are shown throughout Section A of Table 9.

Table 10 summarizes the time-domain data for DC (based upon DConly signal) and ACtrough (based on AConly and Bandstop 0.01-0.5 Hz signals).

TABLE 10

Comparison of DC of DConly Filter with DC surrogates of Bandstop and AConly Filters

|  | Flat (in $AC_{rest}$Mults) | LegRaise (in $AC_{rest}$Mults) | LegRaise − Flat (in $AC_{rest}$Mults) |
|---|---|---|---|
| DConly Filter | | | |
| DC max | 153.92 | 157.4 | 3.48 |
| DC min | 153.62 | 157.0 | 3.38 |
| DC @max − @min | .3 | .4 | .1 |
| Bandstop 0.01-0.5 to eliminate DC oscillations at respiratory frequency | | | |
| ACtrough at max | 153.25 | 156.9 | 3.65 |
| ACtrough at min | 153.1 | 156.6 | 3.5 |
| ACtrough @max − @min | .15 | .3 | .15 |
| AConly Filter | | | |
| ACtrough at max | −.56 | −.43 | .13 |
| ACtrough at min | −.60 | −.45 | .15 |
| ACtrough @max − @min | .04 | .02 | −.02 |

The data show that, although they differ slightly, ACtrough of bandstop and DC of DConly filters are similar, with LegR-Flat increases of 3.5 $AC_{rest}$Mults and 3.38 $AC_{rest}$Mults, respectively. The similarity is due to the elimination of the pulsatile component from the ACtrough tracing. However, there are minor differences, which are attributable to multiple factors. First, ACtrough is a single time point that is recorded as the lowest reading within a pulsatile signal; conversely, being sampled at <0.5 Hz, DC may not capture the single time point. Second, ACtrough at its minimum of respiratory cycle and DC at its minimum of respiratory cycle are not in phase with each other and may not be in synch with each other since ACtrough is dependent on the cardiac ejection for which the impact is delayed compared to the change in DC (preload returning to the heart) and also the timing of ACtrough is also influenced by variations in heart rate.

In addition, an embodiment that entails multiplying the trough of the AConly tracing by the ratio of AC/DC under resting conditions (shown to average approximately 25.6 in preceding embodiments), allows LegR-Flat values of AConly tracing to be converted to equivalents of the trough of AC bandstop and the minimum of DConly tracing even though DC has been eliminated from the tracing. With the exemplary data in Table 10, it is seen that the LegR-Flat difference for AC bandstop tracing (0.350 A $AC_{rest}$Mults) is 23.3 times LegR-Flat in AConly tracing (0.15 ACrestMults); DConly (3.38 $AC_{rest}$Mults) is 22.5 times AConly. The values generated by these embodiments approximate the 25.6/1 ratio of DC/AC shown above and thereby allow unprecedented use of the AConly signal as a mechanism to approximate changes in DC. Discrepancies may alert the clinician to altered DC and AC relationships.

Consistent with the above, the Applicant introduces the following sequence of conversion:

An increase of 0.1 $AC_{rest}$Mults in ACtrough represents ~10% increase in the pulsatile component of the $PPG^{Forehead}$, which is equivalent to ~10 $ml_{PPG}$ (if SV@rest=100 ml).

The corresponding 10% in nonpulsatile volume converts to ~2.56 $AC_{rest}$Mult (or 256 $ml_{PPG}$) increase in DC.

Figure 43:
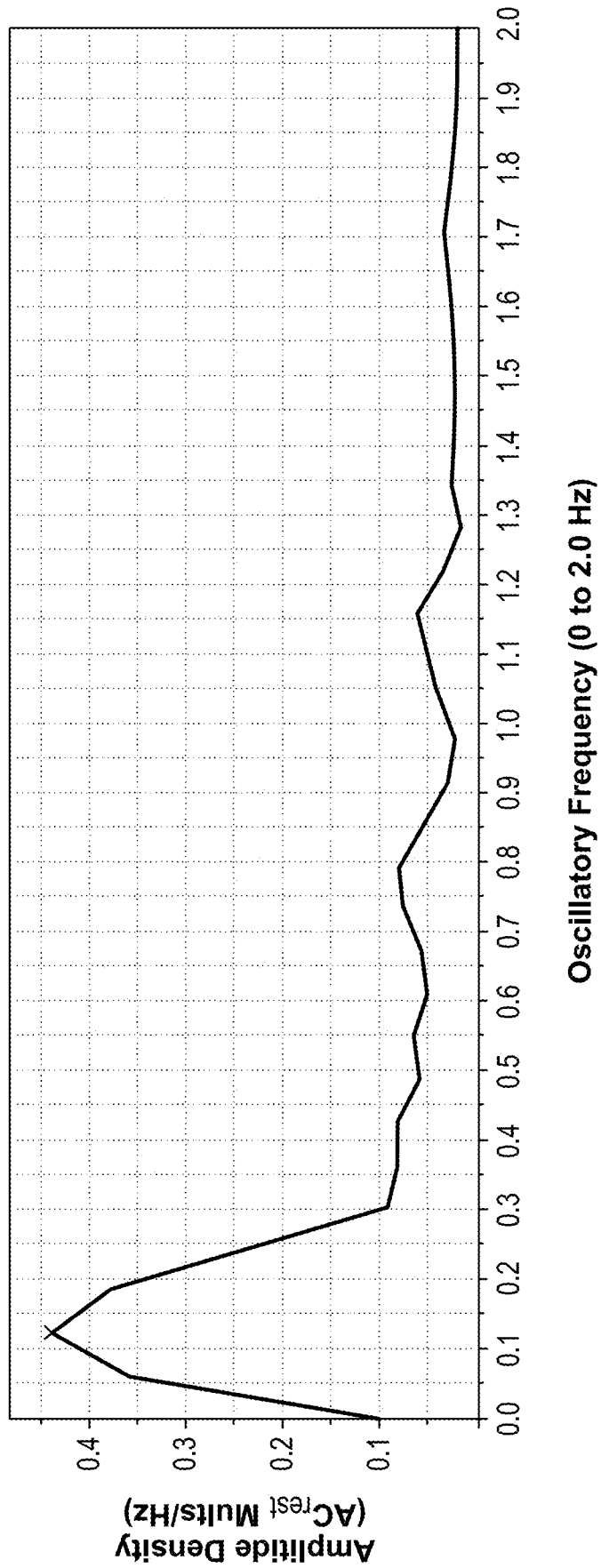
FIG. 43 is a screen shot of spectral domain analysis based upon pseudocontinuous signal generated from successive ACtrough values (in $AC_{rest}$Mults) as may be generated by cyclic and/or peak analysis of PPG waveform. Predominant impact is on low frequency oscillations (0.10-0.20 Hz) since ACtrough is measured before arrival of next cardiac pulsation (at 0.916 Hz and surrounding sidebands). However, ACtrough is relatively more affected than DC by cardiac pulsations as indicated by osillatory power around the cardiac frequency (compared to absence of all oscillatory power above 0.5 Hz in DC only signal).
Figure 44:
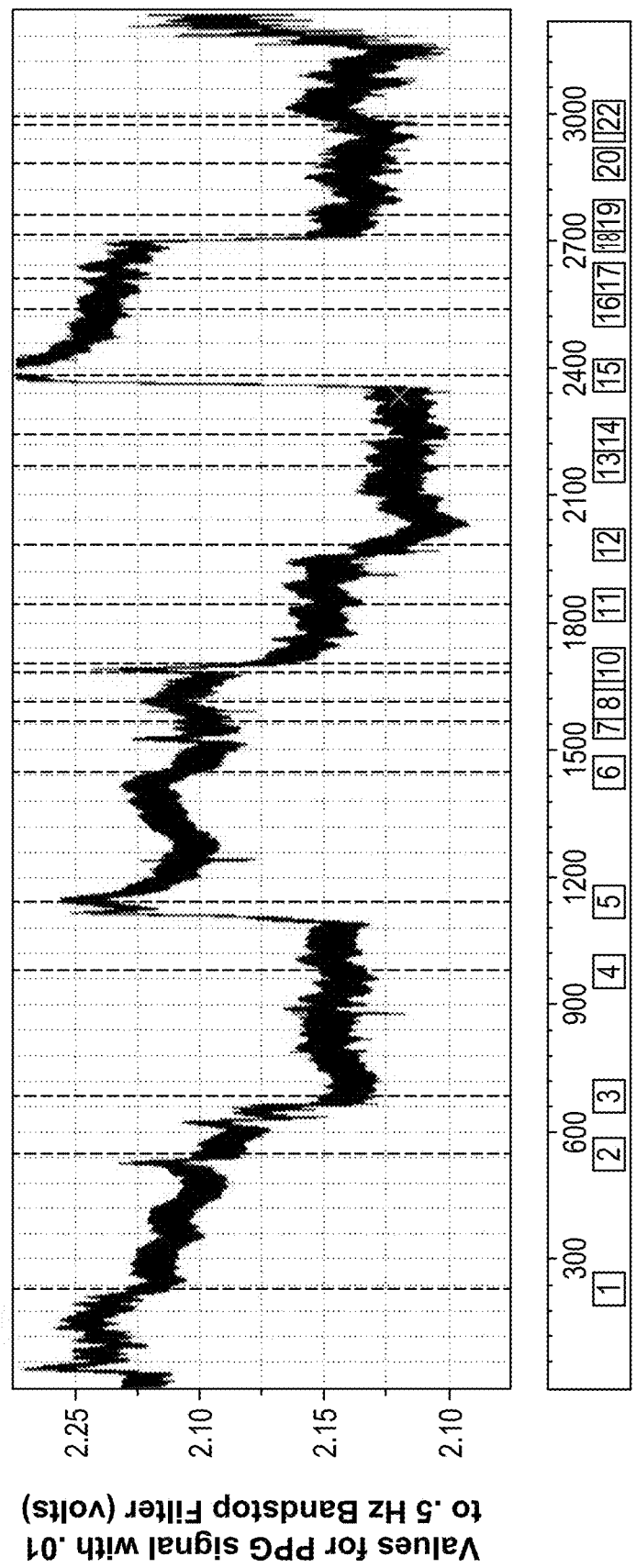
FIG. 44 is a screen shot of a PPG signal after bandstop filter (that eliminates oscillations between 0.01 and 0.5 Hz) to show AC values (including AC pulsations and oscillations) atop DC signal whose oscillations (respiration-induced, autonomic) have been removed by filter.

The distinctions between ACtrough and DC values generated by different filters may be most readily appreciated in the spectral domain (shown in rows B 101, 111, 121, 131 141 and 151 of Table 9). The corresponding spectral displays are shown in FIGS. 40-43 and 45. FIG. 43, the spectral display based on the pseudocontinuous ACtrough tracing during LegR, shows amplitude density of ACtrough at the respiratory frequency of 0.45 $AC_{rest}$Mults/Hz; this is, greater than the corresponding value of DC, 0.32 $AC_{rest}$Mults/Hz in the DConly display during LegR. The differences provide heretofore unattainable delineation of impact of respiration of variations of the AC and DC signal components in the spectral domain.

No respiratory-induced oscillations are seen in the AConly display since oscillations at the respiratory frequency are eliminated by filtering that only captures signals at >0.5 Hz. With the bandstop filter, since DC oscillations are eliminated, only oscillations of the AC component are captured. With the DConly filter, only the DC oscillations are captured. Comparison shows that the AC (representing arterial pulsatile) oscillations are only 53% of the amplitude of DC oscillations in the exemplary subject during Flat and 43% during LegR. The reduction during LegR is consistent with the increase in DC oscillations and the reduction in AC oscillations when volume is increased.

As per preceding embodiments, this can lead to creation of cutoffs with respect to the relationship of $\Delta$respDC and $\Delta$respAC or $\Delta$resp of alternative measures of cardiac ejection such as $\Delta$respSV. As seen with ACtrough and rawPPG values of Section B of Table 9, the impacts are not additive, since the AC and DC oscillations are not in phase.

Exemplary embodiments include:

$\Delta$respAC/$\Delta$respDC $\Delta$respSV/$\Delta$respDC (wherein $\Delta$resp values of one (DC) or both indices can be generated in the frequency domain).

ΔrespAC vs ΔrespDC in Time Domain

Figure 45:
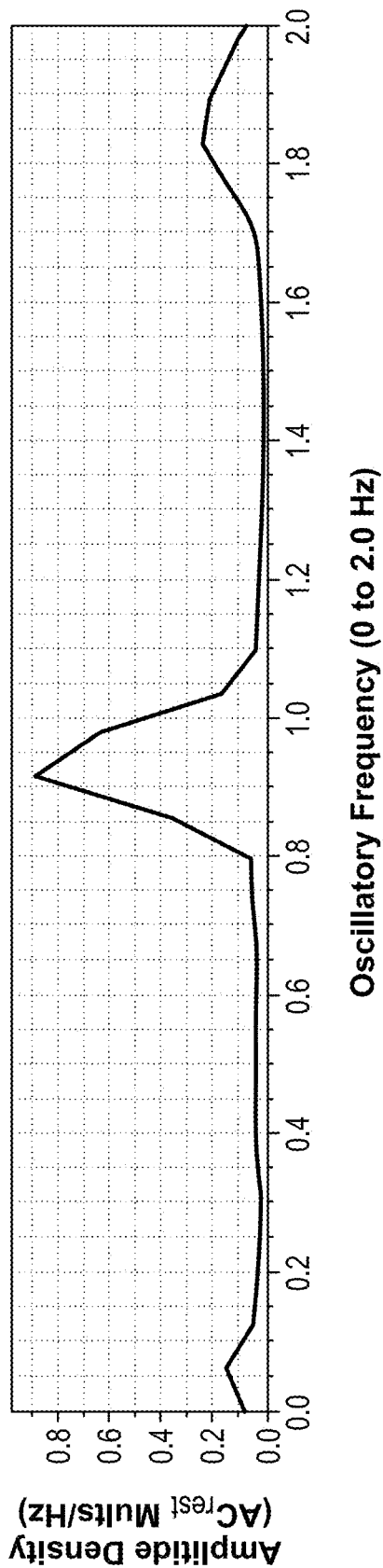
FIG. 45 is a screen shot of spectral domain analysis of AC component (in $AC_{rest}$Mults) generated with 0.01-0.5 bandstop filter of 60 sec interval during LegR. AC pulsations of the PPG signal are maintained atop the DC value, from which all oscillatory activity has been removed. Hence oscillatory activity at low frequencies (respiratory and autonomic) is attributable to variations in the AC signal.
Figure 46:
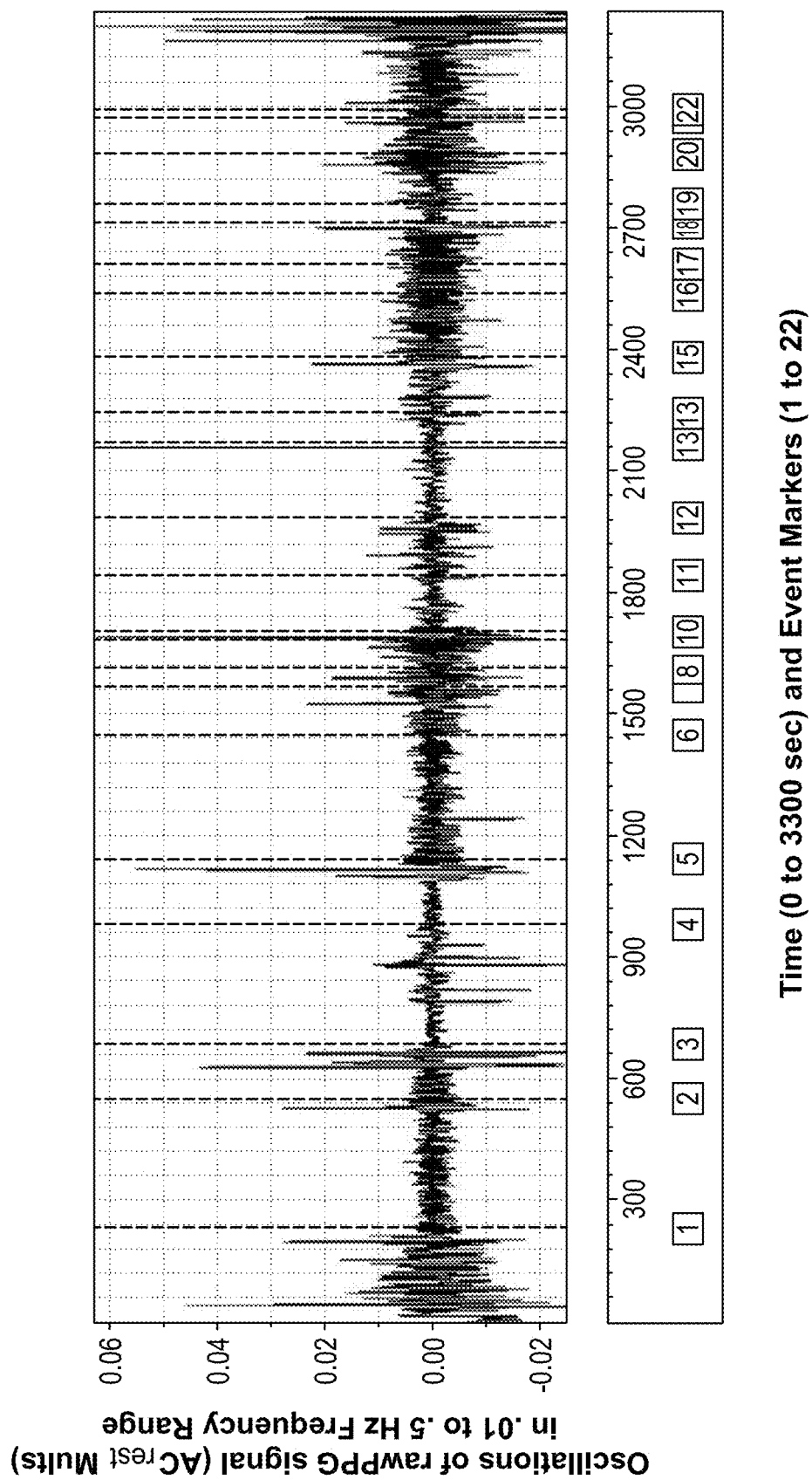
FIG. 46 is a screen shot of a channel showing oscillatory activity between 0.01 and 0.5 Hz (band pass filter). This shows oscillatory activity of DC without underlying static component, thereby facilitating comparisons with an oscillatory signal such as AC only which lacks static DC as well oscillatory DC components. This constitutes a continuous display as opposed to integrating measurements of amplitude density over the time interval (with spectal domain analysis). Note that FIGS. 46-49 show values in volts so as to not confuse a reader who is not familiar with $AC_{rest}$Mults in this initial demonstration of such filtered data. The advantages of $AC_{rest}$Mults and $ml_{PPG}$ are described in text.
Figure 47:
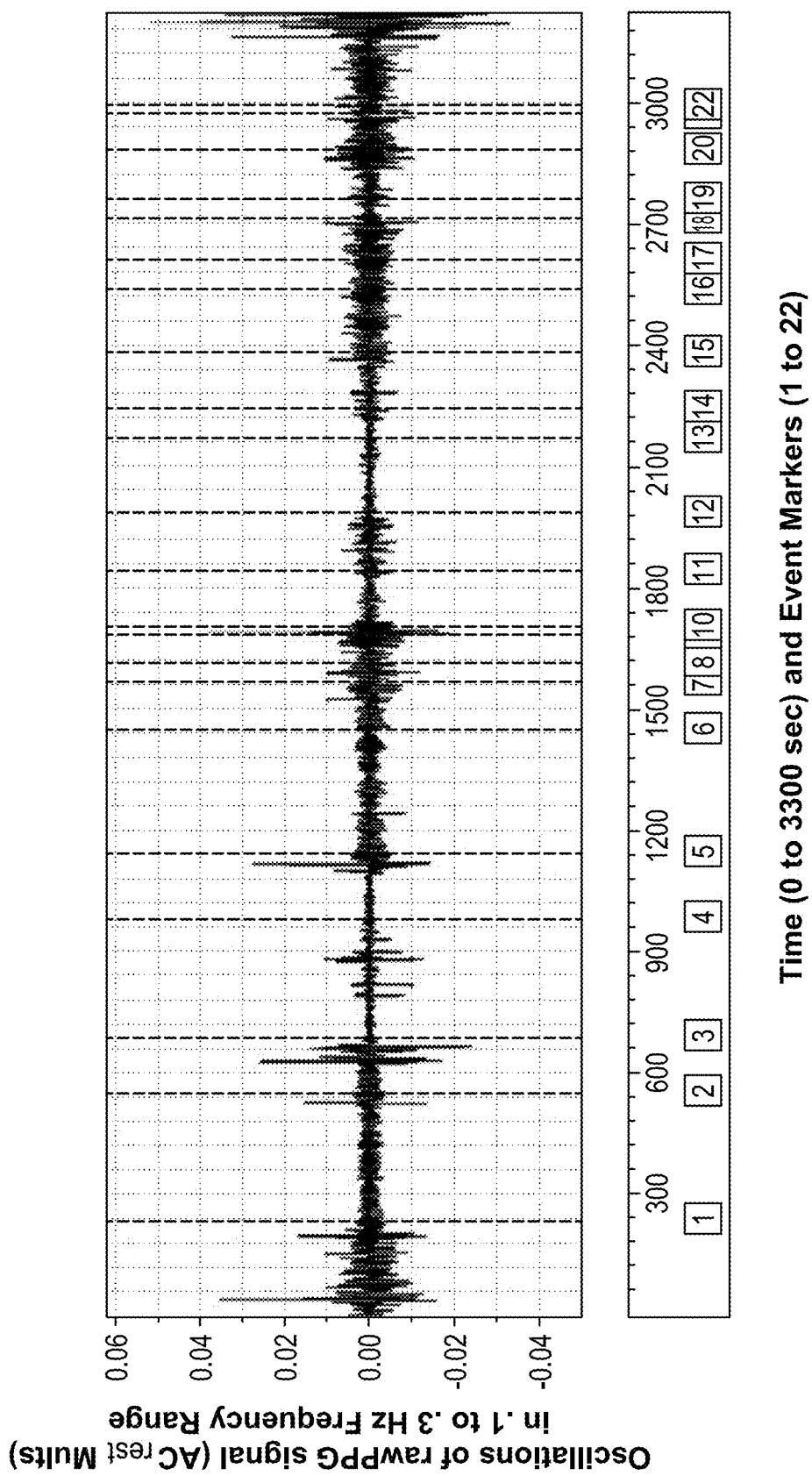
FIG. 47 is a screen shot of channel showing oscillations of raw signal between 0.1 and 0.3 Hz (band pass filter). This shows oscillatory activity of DC in a narrower range than 0.01-0.5 (again, without underlying static component).
Figure 48:
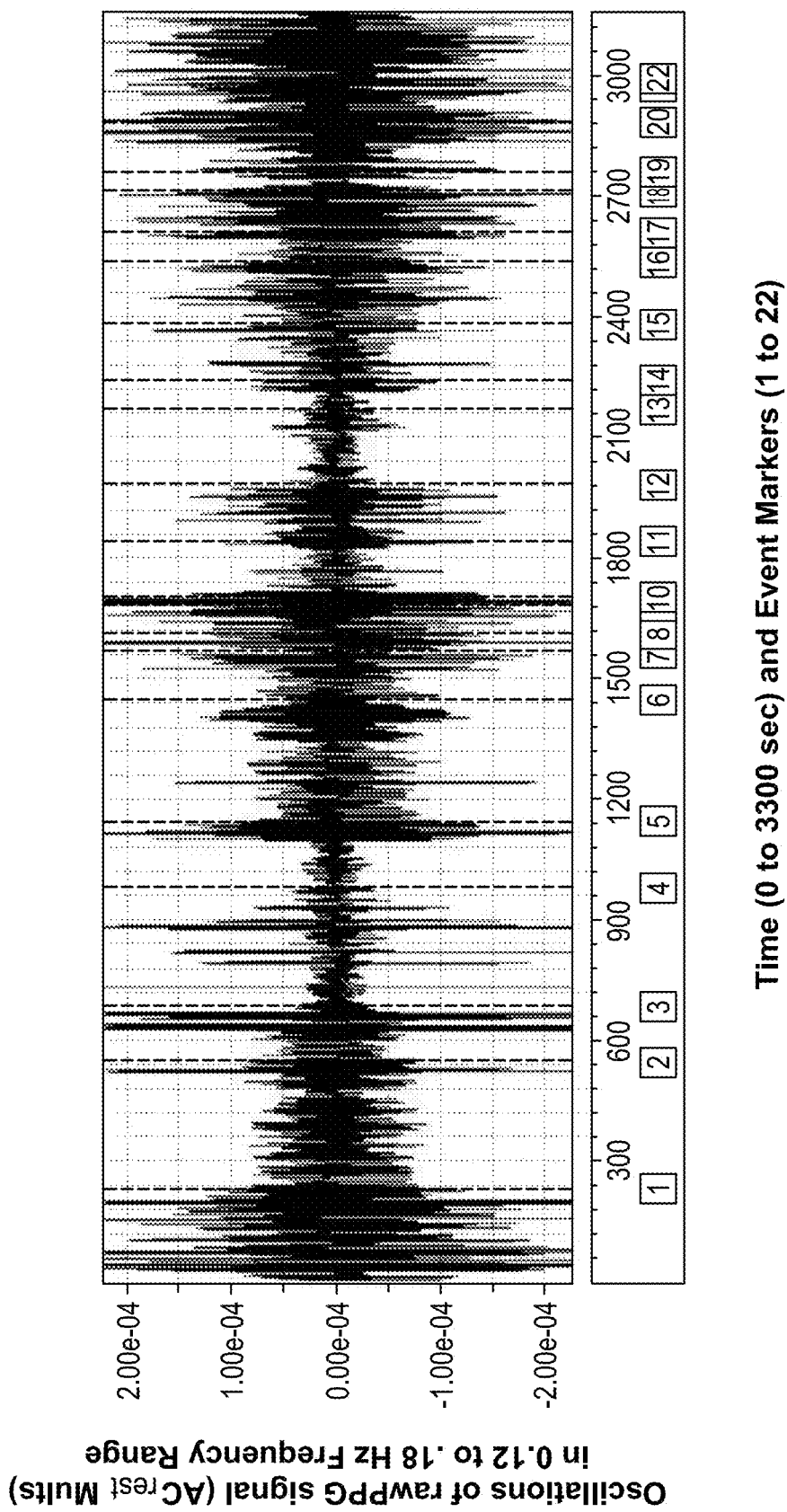
FIG. 48 is a screen shot of channel showing oscillations of AC signal between 0.12 and 0.18 Hz (band pass filter). This is most sensitive to parasympathetic autonomic activity and respiration. This can be compared to other frequencies within same AC signal and/or to frequency bands of other signals (e.g., of DC). Comparison of y-axis to that of FIGS. 46 and 47 shows that oscillatory amplitude of AC signal at this frequency range is far below that for oscillations in frequency ranges shown in FIGS. 46 and 47.
Figure 49:
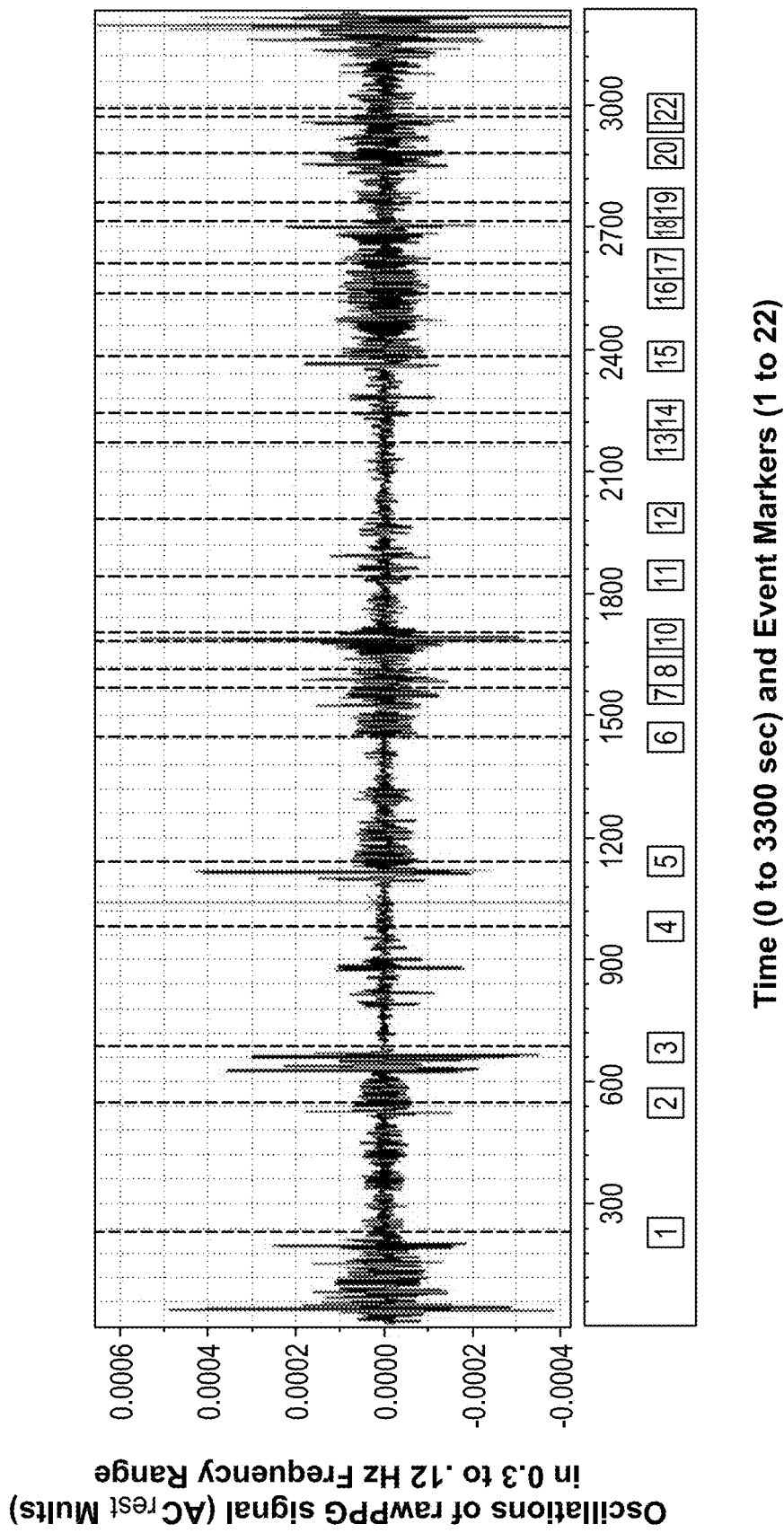
FIG. 49 is a screen shot of channel showing oscillations of AC signal between 0.03 and 0.12 Hz (band pass filter). This is most sensitive to sympathetic activity (again, without underlying static component).

Applicant's objective to integrate venous with arterial changes on a single monitor (i.e., DC with AC of the PPG$^{Forehead}$) prompted delineation of the beat-by-beat impact of LegR on AC. Selective AC assessment was facilitated by:

measuring AC values of the raw signal (shown in AC$_{rest}$Mults): rows A1-7, A21-24, A41-43, 51-53, 61-63 of Table 9; or elimination of signal variation caused by ΔrespDC with a bandstop filter such as that customized by the Applicant to eliminate variations at frequencies between 0.01 and 0.5 Hz while retaining mean DC value. This is shown for raw voltages in FIG. 44 and its time-domain data are summarized in Section C of Table 9. The associated spectrogram is shown in FIG. 45; or use of a highpass "AConly" filter (e.g., >0.5 Hz or 0.5-5.0 Hz bandpass) which totally eliminated the DC signal (as discussed above and shown in spectral display of FIG. 41 and its data are summarized in Table 11 below. (These data were not included in Table 9 because they lack a DC component).

TABLE 11

Data Generated with AConly Filter (as shown in FIGS. 37 and 39)

| AConly Filter | Flat (in AC$_{rest}$Mults) | LegRaise (in AC$_{rest}$Mults) | LegRaise – Flat (in AC$_{rest}$Mults and/or %) |
|---|---|---|---|
| ACpeak at max | .39 | .52 | .13 |
| ACtrough at max | −.6 | −.43 | .17 |
| ACheight at max | .99 | .95 | −.04 |
| ACpeak at min | .29 | .45 | .16 |
| ACtrough at min | −.56 | −.45 | .11 |
| ACheight at min | .85 | .90 | .05 |

In each of these signals, Applicant recorded ACpeak, ACtrough and ACheight (ACpeak-ACtrough) at their max and min for the selected respiratory cycle. The first two options (rawPPG, bandstop filter) enabled calculation of prior art indices of volume assessment based on respiration-induced modulation of the AC signal:

perfusion (pulsatility) index (PI %=100×'ACheight/ACtrough')

wherein ACheight=ACpeak minus ACtrough);
this in and of itself has little intuitive meaning—values expressed in volts, denominator includes background so that % is misleadingly low pleth variability index (PVI %=100×'PI@max−PI@min'/PI@max)

wherein max and min refer to max and min within a given breath

Applicant first examined the bandstop tracing (FIG. 44) which retains the DC value as ~ACtrough but excludes oscillations of DC such as ΔrespDC. The component values are detailed in section C of Table 9.

As summarized in row C232 of Table 9, PVI % was 11.12% and 8.042% during Flat and LegR, respectively. The LegR-induced 27.7% decline in PVI % was consistent with the 25% decline from 16% to 12% for SVV % by NICOM. Because this entailed ratios and differences, PVI % was the same when raw voltage or AC$_{rest}$Mults were used. As noted above in other contexts, AC$_{rest}$Mults made it easier to appreciate the individual components; e.g. the heights used for calculations of PI (Perfusion Index) max and PImin were approximately 1 AC$_{rest}$Mult (as opposed to arbitrary voltages).

Applicant again introduces exemplary ratios of potential interest wherein Applicant introduces a DC component to PVI % assessments and documents that increased DC and ΔrespDC would provide a preload-related foundation for assessing PVI % decreases herein (or conversely PVI % increases during volume loss, high ventilator pressures and tidal volumes, and/or declining cardiac efficiency):

PVI % during Flat/DC during Flat as a % of 25.6=11.12%/*%

PVI % during LegR/DC during LegR as a % of 25.6=8.042/*%

(*=obtainable if background subtracted so as to isolate DCblood as described above)

↓PVI % due to LegR/%↑DC due to LegR=−3.158%/+13.36% where, as per above, %↑DC is determined as increase in:
AC$_{rest}$Mults/presumed 25.6 AC$_{rest}$Mults at rest; or
in ml$_{PPG}$/presumed 3200 ml$_{PPG}$ at rest.

Applicant also proposes embodiments that do not include DCpre as denominator and hence do not require determination or estimation of DCblood:

↓PVI % due to LegR/↑DC due to LegR=−3.158%/+3.42AC$_{rest}$Mults;

↓PVI % due to LegR/↑DC due to LegR=−3.158%/+13.36%,

↓PVI % due to LegR/↑DC due to LegR=−3.158%/+376 ml$_{PPG}$.

Applicant also proposes embodiments that include ΔrespDC, which do not include DCpre as denominator or determination or estimation of DCblood:

PVI % during Flat/ΔrespDC in AC$_{rest}$Mults during Flat=11.12%/1.15AC$_{rest}$Mults (row A7)

PVI % during LegR/ΔrespDC in AC$_{rest}$Mults during LegR=8.042%/1.32 AC$_{rest}$Mults (row A7)

↓PVI % due to LegR/↑ΔrespDC % due to LegR=−3.158%/+0.17 AC$_{rest}$Mults (row A7)

%↓PVI % due to LegR/%↑ΔrespDC % due to LegR=−32.19%/+14.8% (row A7)

Although not shown herein, it is readily apparent that respiratory-induced changes in ACheight also can be viewed in the spectral domain, for which we showed oscillatory changes in signal magnitude and demonstrated the use of a pseudocontinuous signal based on a specific measurement (ACtrough) in the preceding section of this disclosure.

One also could apply relative changes in right atrium (RA), introduced above:

PVI % during Flat/ΔrespRA % during Flat=11.12%/31.4%

PVI % during LegR/ΔrespRA % during LegR=8.042%/50.3%

↓PVI % due to LegR/↑ΔrespRA % due to LegR=−3.158%/+18.9%

%↓PVI % due to LegR/%↑ΔrespRA % due to LegR=−32.19%/+60.19%

Applicant also notes that, consistent with descriptions above for other assessments of SV and SV variation, numerator and denominator of ratios involving variations of PVI/DC can be used to graph on quadrant map and to determine cutoffs by which to assess degree of hypovolemia and response to therapy. A favorable response to administration of volume would be in the right lower quadrant The above formulae show that the PVI % decreased by 3.158% in response to a +0.17 $AC_{rest}$Mults (1.32-1.15) increase ΔrespDC; (respective relative changes were −32.19% and +14.8%). If ΔrespDC were +0.34 and PVI again decreased by 3.158%, this would indicate that the heart was only half as responsive to the increase in volume attributable to ΔrespDC (unless there was volumetric auto-regulation of the AC signal as discussed below). This may be vital not only to assessing the magnitude of an anticipated response but help to identify the all-too-common clinical conundrum (referred to as "gray zone") of a PVI "nonresponder" to what was anticipated to be a therapeutic addition of fluid. The DC component will tell you if the attempted therapy (or alternatively blood loss) had an impact on the active venous circulation. The PVI/ΔrespDC ratio and variants thereof will provide a virtual response/dose relationship and thereby provide insight into stroke volume/venous volume status and changes thereof. Once established in clinical trials, this ratio will provide cutoffs and aforementioned quadrant assignments with respect to changes in venous and stroke volumes and surrogates thereof akin to the Frank-Starling relationship of end diastolic volume vs stroke volume.

In addition, embodiments shown above reveal how the use of a meaningful DC measurement in the denominator may not only improve the usefulness of PVI as well as other assessments of increasing or decreasing of SV or ΔrespSV but actually may obviate the need for PVI calculation when these measurement are numerator and DC or ΔrespDC is the denominator.

Applicant has shown volume replacement and posture (LegR) above and provides further details about posture below. In the absence of an asleep subject receiving positive pressure ventilation, the impact of ventilator settings cannot be shown. However, Applicant already delineated with spectral domain displays the impact of positive pressure on amplitude densities in FIGS. 29-31. It is anticipated that aforementioned embodiments will guide potential use of smaller tidal volumes and lower ventilator pressures in the presence of hypovolemia so as not to cause pronounced changes in preload to a heart in need of volume.

AC Vs DC as an Indicator of Volumetric Autoregulation:

Applicant appreciated that measurement of DC in the context of LegR not only would enhance assessment of SV and SVV % at the level of the heart (as above) but that it would explain peculiarities of the AC component at the $PPG^{Forehead}$ observed by the Applicant, and attributable herein by the Applicant to his introduction of "volumetric autoregulation."

Data from Table 8 shows that LegR caused a 25% increase of SV. If the LegsR-induced increase in SV were fully transferred to the AC signal, then the LegR-induced rise in ACpeak should exceed that of ACtrough by ~0.25 $AC_{rest}$Mults (which would correspond to the 25% increase of SV). However, as shown by data in Table 9 the LegsR-induced increase of ACpeak was only 0.075 $AC_{rest}$Mults greater than for ACtrough. This suggests suppression of the increase in ACheight to 28% (100×0.075/0.25) of the 25% increase of SV.

Even more dramatic, Applicant quantifies blunting in AConly signal of Table 11: LegR actually caused a decrease in ACheight (peak minus trough) at its maximum during respiratory cycle from 0.99 $AC_{rest}$Mults during Flat to 0.95 $AC_{rest}$Mults during LegR (4% decline).

Applicant also quantifies this decline with amplitude densities at the cardiac frequency of spectral display of Section B of Table 9:
 rawPPG in volts: decreased by 2.51 volts (−16.472%)
 rawPPG in $AC_{rest}$Mults: decreased by 0.18 $AC_{rest}$Mults s (−16.52%)
 (note the intuitive clarity of the $AC_{rest}$Mults when compared to AC@rest=1 $AC_{rest}$Mult)
 Bandstop in $AC_{rest}$Mults: decreased by 0.17 $AC_{rest}$Mults (−16.3%)
 AConly (not shown in Table 9): decreased by $AC_{rest}$Mults (−15.3%)

These declines were noted despite the 25% increase recorded for SV.

The influence of venous volume (DC) at the monitoring site was evidenced by increase in ACtrough (before arrival of pulsatile signal) even in the AConly tracing, such that, instead of causing an increase, LegR caused a 4.88% decline of ACheight @max and a 3.54% decline of ACheight @min (since ACheight=ACpeak−ACtrough) (Table 11). The comparison provides a mechanism for assessing volumetric autoregulation wherein, because it has a greater volume than ACtrough, ACpeak is more likely to approach the autoregulatory volumetric threshold and thus is blunted to a greater degree by increased venous blood (DC) at the monitoring site.

It is appreciated that blunting of the ACheight alone is not definitive for local autoregulation since it is possible that a patient with compromised cardiac function could have decreased efficiency in the context of an increased volume load. Hence the need for the exemplary relationships introduced below and variations thereof (in time- and/or spectral-domains), which are summarized as follows:

↑ACpeak/↑ACtrough; and/or

↑ACpeak/↑SV

As shown below, Applicant introduces mechanism to quantify impact of increase in DC on the blunting of the AC peak and AC height; i.e., Applicant introduces mechanisms to quantify the degree of volumetric autoregulation of the local microvascular bed in the context of an increase of DC (local capillovenous volume). As shown below, the differing impact on raw and bandstop signals vs AC signal is attributable to the varying impact on DC on the cumulative peak. Progressive introduction of DC components in the time-domain showed the impact of DC on ACheight and enables introduction of embodiments for comparison.

In the bandstop tracing, the increased volume of venous blood also contributed to the magnitude of the ACheight; both ACpeak and ACtrough reflected the addition of change in DC to the volume delivered with the cardiac pulsation, such that LegR caused an 8.108% increase in ACheight @max and a 8.824% increase in ACheight@min. In the raw signal, (wherein the voltage changes associated with ΔrespDC are also incorporated in readings at the given time point), the tracing indicated a 1% increase in ACheight @max and 12.5% @min. The limited cumulation is attributable to Applicant's description above that AC and DC, when not in synch, can be additive or counteractive Hence, none of the AC measurements indicated the 25% increase in SV detected by NICOM and spectral domain of all filtering methods as well as time-domain analysis of the AConly signal documented a decline in ACheight during LegR. This is consistent with the observations that, despite causing an increase in SV, LegR caused a greater increase in ACtrough (reflective of ↑DC) than of ACpeak (reflective of DC plus increase in SV).

Impact of DC may be quantified by comparing impact on different tracings of increase of DC on ACpeak and/or ACtrough. Exemplary embodiments for assessing the impact of DC on the AC at a given site also include dividing above ratios by DC or ΔDC:

'Δ of AC/SV'/'ΔDC'

'↑ACpeak/↑ACtrough'/ΔDC within and among filtered signals wherein the different filters define the degree to which DC will impact the AC value and hence the degree of change in the relationship of AC to SV (wherein calculations are included in Tables 9-11).

Applicant determines this relationship as a unique mechanism to assess regulation of local volume at a critical region such as the brain (which shares vasculature and autonomic innervation with the forehead as suggested by the Applicant using different devices and different methodology in U.S. Pat. No. 7,367,941 (Silverman D G, Stout R G) entitled "Detection and characterization of cholinergic oscillatory control in peripheral microvasculature," which is incorporated herein by reference). Loss of autoregulaton would be an indicator of compromised regional (e.g., cerebral) perfusion and regulation thereof. Applicant anticipates that this may constitute a much-needed mechanism to assess not only the magnitude of autoregulation but its impact at the microvascular level.

Autoregulation During Other Postural Changes:

The remaining segments of the series of postural challenges enable assessment of the impact of local changes in DC on local changes in AC.

Although not the focus of the present assessment, the more extreme postural changes in exemplary volunteer subject supported the assessments noted above. 45° HeadDown/LegsUP tilt caused the greatest increase in DC (to 187 $AC_{rest}$Mults) (time point 15 on FIG. 32). This was accompanied by an increase in SV (to 150 ml) (Table 8) but AC height decreased to 0.875 $AC_{rest}$Mults in AConly channel; hence the increase in venous volume caused an increase in SV but its impact on AC was impeded at the $PPG^{Forehead}$.

FIGS. 46 to 49 show tracings that have been subjected to filtering that enables comparison of the magnitude of autonomic responses and thereby provide ratios indicative of autoregulation. While this is also apparent (and more definitively quantified by spectral displays), FIGS. 46-49 provide readily discernible changes within a given frequency band for the entire study. Alternatively, one could integrate the signals with joint time frequency analysis.

An exemplary autonomic assessment consists of comparing values of and changes within the frequency ranges of 0.03-0.12 Hz (sympathetic) and 0.12-0.18 Hz (parasympathetic activity during extremes of posture in the volunteer subject.

| | Sympathetic/Parasysmpathetic |
|---|---|
| During Head Up/Legs Down tilt | 0.00001/0.000002 |
| During Head Down/Legs Up tilt: | 0.00008/0.000010 |

Comparing head up/leg down tilt to head down/legs up tilt, Applicant shows that sympathetic vasoconstrictive activity was 8× higher when there was increased DC volume (head down). This increase in sympathetic activity was accompanied by a lesser increase in parasympathetic activity.

The change in the sympathetic/parasympathetic ratio can be compared to DC:

Δ amplitude density at parasympathetic frequencies/ΔDC

Δ amplitude density at sympathetic frequencies/ΔDC

Figure 50:
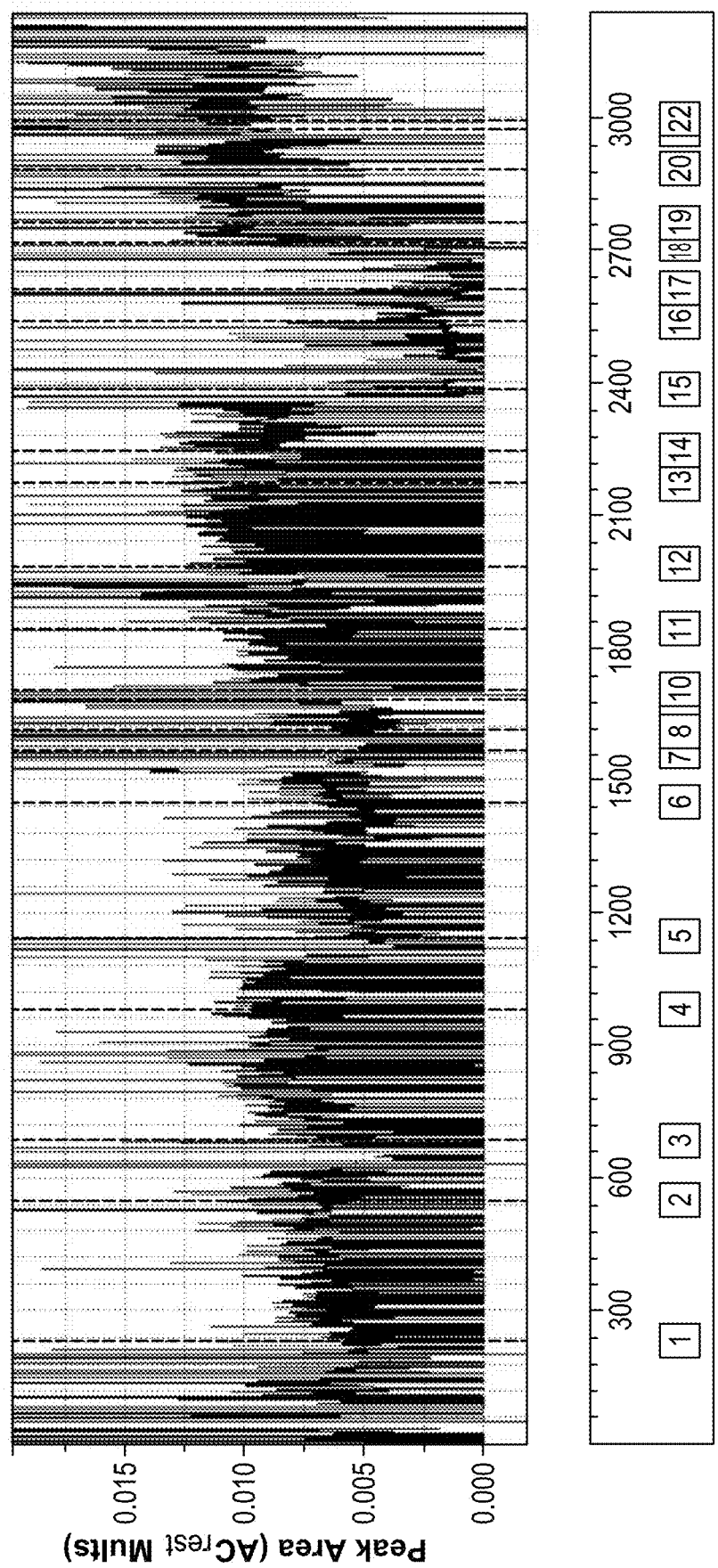
FIG. 50 is a screen shot showing that there are alternatives to AC height (also referred to in prior art as AC amplitude) and ACpeak. Here is shown peak area (area between baseline and signal peak) in $AC_{rest}$Mults. Using the measure of area is helpful for confirming changes in AC associated with a challenge. Also it may be more reflective of herein termed "distribution" phase for each beat pulsatile waveform (as opposed to herein termed "propulsive" phase via artery at onset of pulse or herein termed "drainage" phase via veins to heart at end of pulse).
Figure 51:
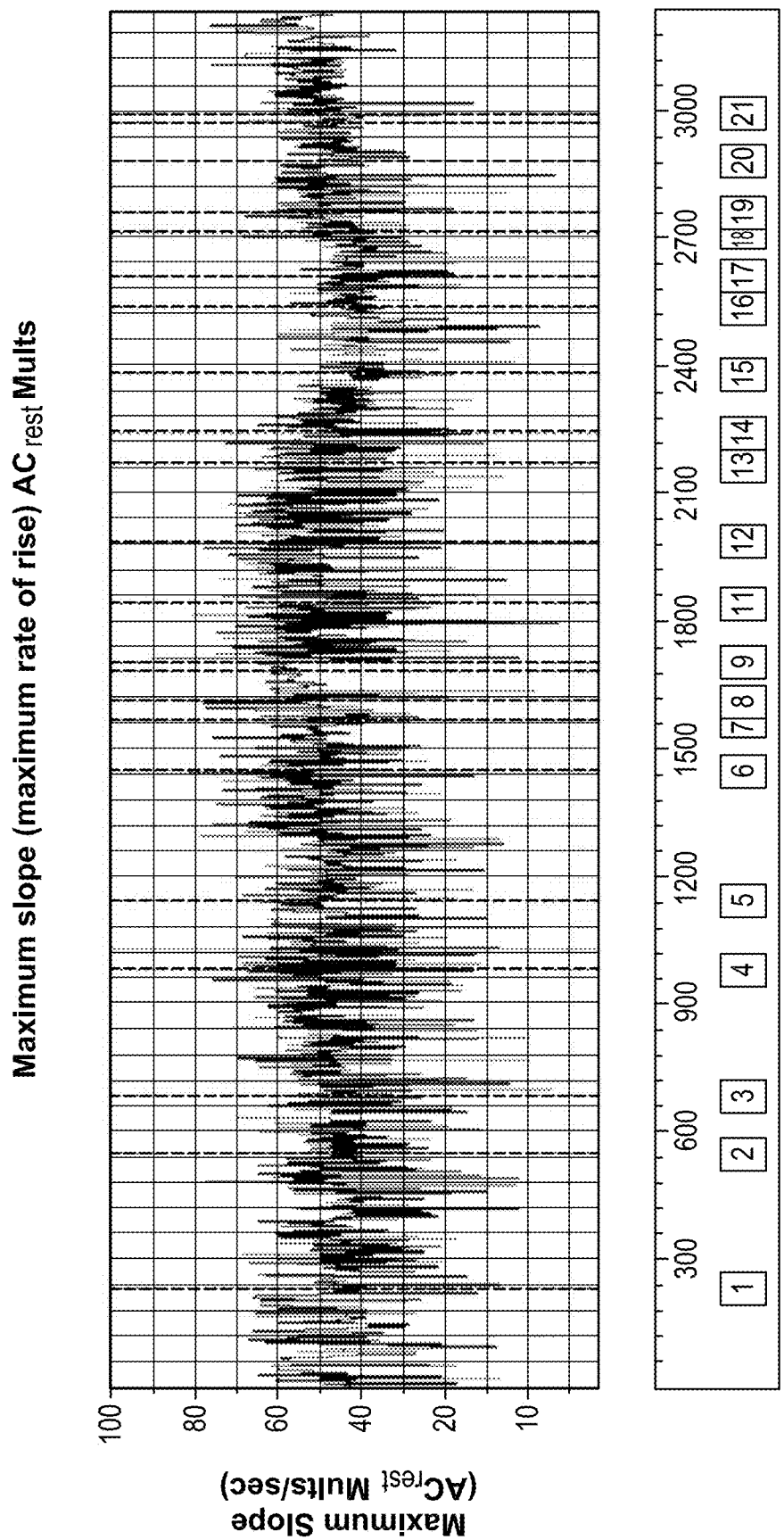
FIG. 51 is another screen shot showing that there are alternatives to AC height and ACpeak. Here is shown maximum slope (maximum rate of rise) in $AC_{rest}$Mults. It is helpful to confirm direction of changes in AC in response to a challenge. This is reflective of propulsive phase for each beat of pulsatile waveform; alternatively, peak area reflects distributive phase and minimum slope reflects the drainage phase (not shown). This also can be reflected by looking at times within the pulse (e.g. time to peak)

This impedance of arterial inflow during HeadDown/LegsUP was further evidenced by the decline in area of the AC signal (ACarea); this decreased to 50% of its value during Flat (FIG. 50). Viewing the pulsatile waveform as a composite of propulsive, distributive and drainage segments, the embodiments introduced herein illustrate that the what is herein called the early "propulsive phase" of the pulse (as indicated by max slope of FIG. 51) was normal (indicating unimpeded delivery of the SV to the monitoring site) but that the subsequent herein termed "distributive phase" was compromised such that the delivery and arteriolar-capillary distribution of the delivered blood was impeded, consistent with impedance due to capillovenous blood already present upon arrival of the pulse.

In contrast, the greatest decline in DC was seen during HeadUp/LegsDown tilt. DC decreased to 177 $AC_{rest}$Mults (FIG. 32) and SV declined to 80 ml (Table 8), but AC height increased to 1.35 $AC_{rest}$Mults (FIG. 32). Hence, although the decrease in DC caused a decline in SV by decreasing venous return to the central circulation and heart, impedance of AC delivery was mitigated such that AC height was increased by approximately 35% and peak area increased by approximately 75% ((FIG. 50)

Despite a less dramatic decline in DC at $PPG^{Forehead}$ (to 178.5 $AC_{rest}$Mults), head raise caused changes similar to those of HeadUp/LegsDown tilt: ACpeak=0.6, ACtrough=-0.55 such that ACheight=1.15 $AC_{rest}$Mults (FIG. 32) (while SV declined to 70 ml, Table 8).

Hence, the findings suggest that, in the presence of an increased DC, the increased capillovenous blood constitutes an increase in local afterload to the incoming pulse and/or initiates a vasoconstrictive response to avoid local hyperemia (e.g., stretch reflex). Conversely, lowering DC, facilitates delivery of the pulsatile volume. Clinical and investigative implications encompass determination of optimum level of volume replacement and optimum head positioning relative to the heart as well as assessment of regional autoregulation in the context of varied physiological, pharmacological (e.g., general anesthesia) and pathophysiological states (e.g., autonomic neuropathy and endothelial dysfunction of diabetes and perhaps states of altered cognition).

Repeat of a portion of the challenge with PPG on different sites showed that, in contrast to the forehead and ear, DC as well as AC at the finger decreased during LegsR (FIG. 33). This apparently vasoconstrictive response at the finger was not seen when the hand was elevated from resting on the stretcher to midthoracic height of the chest wall. The slightly elevated arm behaved more akin to forehead and ear: LegsR caused ~3 $AC_{rest}$Mult rise in DC; AC height decreased to a greater degree than the other sites (ACpeak to 0.4 and ACtrough to -0.35 $AC_{rest}$Mults from 0.5 and -0.5 $AC_{rest}$Mults). This is worth exploring further not only from a physiologic standpoint but also because of the widespread use of $PPG^{Finger}$ (as shown for comparison of ear and finger with respect to lower body negative pressure (above).

To determine if the decline in PPG height seen as the forehead (and ear) during LegR was specific to the cranial vessels, Applicant repeated this particular postural challenge while monitoring PPG at another relatively central site that was outside the region of the carotid artery and cranial microvasculature. The rawPPG signal at the lateral surface of the upper arm, albeit of relatively low magnitude, showed a pronounced rise in DC which, in contrast to the $PPG^{Forehead}$ and $PPG^{Ear}$ had a slight increase in AC height. This suggests that it may be more reflective of the change in SV and serve as a reference for assessment of the impedance of AC at the forehead. Moreover, it suggests that the DC-associated impedance of AC delivery at the forehead is due to local vasoconstrictive response since comparable impedance was not seen despite increased DC at the upper arm. This argues in favor of volumetric autoregulation of the cranial vessels.

While the preferred embodiments have been shown and described, it will be understood that there is no intent to limit the invention by such disclosure, but rather, it is intended to cover all modifications and alternate constructions falling within the spirit and scope of the invention.

The invention claimed is:

1. A microprocessor implemented method for photoplethysmograph measurement of volume status and changes, comprising:
    measuring, at a monitoring site, a DC component of a photoplethysmographic signal;
    measuring, at a monitoring site, changes resulting from changes in cardiac ejection of pulse as indicated by stroke volume, cardiac output, blood pressure or pulsatile component of a peripheral monitor;
    comparing changes in the DC component to changes resulting from changes in cardiac ejection of pulse as indicated by stroke volume, cardiac output, blood pressure or pulsatile component of a peripheral monitor to provide a ratio;
    applying the ratio to noninvasively provide a measure of relative values and changes thereof in preload to and blood ejection by the heart to quantify changes in pulsatile and non-pulsatile volume status of a local microcirculation to assess changes in local volume;
    establishing cutoffs for clinically meaningful positive and negative responses to a challenge or intervention based upon SV assessment/DC measurement ratio and ΔSV assessment/ΔDC measurement ratio;
    assigning values to quadrant of one of a series of SV assessment/DC measurement and ΔSV assessment/ΔDC measurement quadrant maps; and
    monitoring systemic vessel physiology, pharmacology, cardiac function, and blood volume based upon the measure of relative values and changes thereof in preload to and blood ejection by the heart to identify and monitor conditions of altered volume and guide treatment of vessel physiology cardiac function, or blood volume.

2. The method according to claim 1, wherein the DC component is measured in $AC_{rest}$Mults.

3. The method according to claim 1, wherein the DC component is measured in $ml_{PPG}$.

4. The method according to claim 1, wherein the DC component is normalized to a baseline value of the DC component.

5. The method according to claim 1, further including the step of quantifying a change in blood ejection by the heart with a measure of respiration-induced variation.

6. The method according to claim 5, wherein the measure of respiration-induced variation is the perfusion index.

7. The method according to claim 5, wherein the measure of respiration-induced variation is the pleth variability index.

8. The method according to claim 1, further including the step of eliminating AC component of the photoplethysmographic signal which includes filtering oscillations at >0.5 Hz from the photoplethysmographic signal.

9. A microprocessor implemented method for photoplethysmograph measurement of volume status and changes, comprising:
    measuring, at a monitoring site, oscillatory changes in a DC component of a photoplethysmographic signal;
    measuring, at a monitoring site, changes resulting from changes in cardiac ejection of pulse as indicated by stroke volume, cardiac output, blood pressure or pulsatile component of a peripheral monitor;
    comparing oscillations in the DC component to changes in cardiac ejection of pulse as indicated by stroke volume, cardiac output, blood pressure or pulsatile component of a peripheral monitor to provide a ratio that noninvasively provides a measure of oscillations in preload to changes in blood ejection by the heart;
    establishing cutoffs for clinically meaningful positive and negative responses to a challenge or intervention based upon SV assessment/DC measurement ratio and ΔSV assessment/ΔDC measurement ratio;
    assigning values to quadrant of one of a series of SV assessment/DC measurement and ΔSV assessment/ΔDC measurement quadrant maps; and
    monitoring systemic vessel physiology, pharmacology, cardiac function, and blood volume based upon the measure of oscillations in preload to changes in blood ejection by the heart to identify and monitor hypovolemic conditions.

10. The method according to claim 9, wherein the oscillations in the DC component are due to respiration.

11. The method according to claim 9, wherein the oscillations in the DC component are quantified in time-domain.

12. The method according to claim 9, wherein the oscillations in the DC component are quantified in spectral domain.

13. The method according to claim 9, wherein frequency bands within the DC component of a photoplethysmographic signal are isolated to selectively assess impact of respiration.

14. The method according to claim 9, wherein frequency bands within the DC component of a photoplethysmographic signal are isolated to selectively assess impact of autonomic activity.

15. The method according to claim 9, further including the step of quantifying the change in blood ejection by the heart with a measure of respiration-induced variation.

16. The method according to claim 15, wherein the measure of respiration-induced variation is the pleth variability index.

17. The method according to claim 9, further including the step of eliminating AC component of the photoplethysmographic signal which includes filtering oscillations at >0.5 Hz from the photoplethysmographic signal.

18. A microprocessor implemented method for photoplethysmograph measurement of volume status and changes, comprising:
    measuring, at a monitoring site, a DC component of a photoplethysmographic signal and a AC component of photoplethysmographic signal;
    determining a baseline, estimated baseline or a preintervention value of the DC component;
    determining a baseline, estimated baseline or a preintervention value of the AC component;

establishing cutoffs for clinically meaningful positive and negative responses to a challenge or intervention based upon SV assessment/DC measurement ratio and ΔSV assessment/ΔDC measurement ratio;

assigning values to quadrant of one of a series of SV assessment/DC measurement and ΔSV assessment/ΔDC measurement quadrant maps; and wherein conditions of altered volume and guide treatment of vessel physiology, cardiac function, or blood volume are identified and monitored by comparing a difference in the DC component from the baseline, estimated baseline or preintervention value to a difference in the AC component from the baseline, estimated baseline or its preintervention value to identify and monitor conditions of altered volume and guide treatment of vessel physiology, cardiac function, or blood volume.

19. The method according to claim 18, wherein measurements are taken at multiple sites.

20. The method according to claim 19, wherein a change in the difference in the AC component in association with the difference in DC component is compared to change at a different monitoring site.

21. The method according to claim 18, wherein a change in the difference in the AC component in association with the difference in DC component is compared to change of measure of cardiac pulsatile ejection.

22. The method according to claim 21, wherein a relative decline in the AC component at a given site is an indication of local volumetric autoregulation.

* * * * *